US012310737B2

United States Patent
Bennett et al.

(10) Patent No.: US 12,310,737 B2
(45) Date of Patent: May 27, 2025

(54) INTERACTIVE 2D SCATTER PLOT OF EGM CHARACTERISTIC METRICS

(71) Applicant: Boston Scientific Scimed Inc., Maple Grove, MN (US)

(72) Inventors: Nathan H. Bennett, Cambridge, MA (US); Brian Stewart, North Reading, MA (US); Nicholas Herlambang, Quincy, MA (US); Suzhou Li, Cleveland Heights, OH (US); Mordechai Perlman, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 650 days.

(21) Appl. No.: 17/489,036

(22) Filed: Sep. 29, 2021

(65) Prior Publication Data

US 2022/0095986 A1 Mar. 31, 2022

Related U.S. Application Data

(60) Provisional application No. 63/085,659, filed on Sep. 30, 2020.

(51) Int. Cl.
*A61B 5/367* (2021.01)
*A61B 5/00* (2006.01)

(52) U.S. Cl.
CPC ............ *A61B 5/367* (2021.01); *A61B 5/7246* (2013.01); *A61B 5/7264* (2013.01); *A61B 5/743* (2013.01)

(58) Field of Classification Search
CPC ......... A61B 5/72; A61B 5/7264; A61B 5/367; A61B 5/7246

(Continued)

(56) References Cited

U.S. PATENT DOCUMENTS

| 4,721,114 A | 1/1988 | DuFault et al. |
| 5,058,599 A | 10/1991 | Andersen |

(Continued)

FOREIGN PATENT DOCUMENTS

| EP | 2563473 B1 | 7/2014 |
| EP | 2371280 B1 | 8/2014 |

(Continued)

OTHER PUBLICATIONS

Daoud et al, Identification of Repetitive Activation Patterns Using Novel Computational Analysis of Multielectrode Recordings During Atrial Fibrillation and Flutter in Humans, JACC: Clinical Electrophysiology, vol. 3, No. 3, 2017.

(Continued)

*Primary Examiner* — Nadia A Mahmood
(74) *Attorney, Agent, or Firm* — Nelson Mullins Riley & Scarborough LLP

(57) ABSTRACT

At least some embodiments of the present disclosure is directed to a system for processing cardiac information. The system comprises a processing unit configured to: receive an activation waveform comprising a set of activation waveform data of a plurality of signal sections collected at a plurality of locations; receive a range of window size. For each of the plurality of signal sections, the processing unit is further configured to: determine a set of confidence values, by iterating through a plurality of window sizes in the range of window size. For each of the plurality of signal sections, the processing unit is further configured to determine one of a plurality of local cycle lengths for the each of the plurality of signal sections based on the selected window size. And generate a representation of the plurality of local cycle lengths.

20 Claims, 28 Drawing Sheets

(58) Field of Classification Search
USPC .................................................. 600/509
See application file for complete search history.

(56) References Cited

U.S. PATENT DOCUMENTS

| | | |
|---|---|---|
| 5,584,295 A | 12/1996 | Muller et al. |
| 6,070,094 A | 5/2000 | Swanson et al. |
| 6,233,491 B1 | 5/2001 | Kordis et al. |
| 6,236,883 B1 | 5/2001 | Ciaccio et al. |
| 8,170,654 B1 | 5/2012 | Zhang et al. |
| 8,301,235 B2 | 10/2012 | Zhang et al. |
| 8,306,614 B2 | 11/2012 | Stadler et al. |
| 8,315,699 B2 | 11/2012 | Stadler et al. |
| 8,340,766 B2 | 12/2012 | Ryu et al. |
| 8,401,629 B2 | 3/2013 | Stadler et al. |
| 8,406,872 B2 | 3/2013 | Stadler et al. |
| 8,437,840 B2 | 5/2013 | Patel et al. |
| 8,437,842 B2 | 5/2013 | Zhang et al. |
| 8,437,851 B2 | 5/2013 | Corbucci et al. |
| 8,457,728 B2 | 6/2013 | Schneider et al. |
| 8,483,813 B2 | 7/2013 | Zhang et al. |
| 8,509,902 B2 | 8/2013 | Cho et al. |
| 8,521,269 B1 | 8/2013 | Gunderson et al. |
| 8,521,275 B2 | 8/2013 | Stadler et al. |
| 8,543,198 B2 | 9/2013 | Zhang et al. |
| 8,594,775 B2 | 11/2013 | Ghosh et al. |
| 8,615,298 B2 | 12/2013 | Ghosh et al. |
| 8,620,433 B2 | 12/2013 | Ghosh et al. |
| 8,639,316 B2 | 1/2014 | Sarkar |
| 8,676,305 B2 | 3/2014 | Hayam et al. |
| 8,738,120 B2 | 5/2014 | Bjrling et al. |
| 8,744,560 B2 | 6/2014 | Gunderson et al. |
| 8,755,889 B2 | 6/2014 | Scheiner |
| 8,768,465 B2 | 7/2014 | Ghosh et al. |
| 8,774,909 B2 | 7/2014 | Patel et al. |
| 8,812,107 B2 | 8/2014 | Virag et al. |
| 8,827,913 B2 | 9/2014 | Havel et al. |
| 8,845,631 B2 | 9/2014 | Werneth et al. |
| 8,886,173 B2 | 11/2014 | Davies et al. |
| 8,886,307 B2 | 11/2014 | Sambelashvili et al. |
| 8,886,314 B2 | 11/2014 | Crutchfield et al. |
| 8,929,984 B2 | 1/2015 | Ghosh et al. |
| 8,948,869 B2 | 2/2015 | Ghosh et al. |
| 8,965,489 B2 | 2/2015 | Ghosh |
| 8,972,005 B2 | 3/2015 | Rasmussen et al. |
| 8,977,350 B2 | 3/2015 | Sarkar et al. |
| 8,983,585 B2 | 3/2015 | Zhang et al. |
| 8,983,586 B2 | 3/2015 | Zhang |
| 9,002,089 B2 | 4/2015 | Grass et al. |
| 9,031,642 B2 | 5/2015 | Ghosh |
| 9,061,155 B2 | 6/2015 | Gillberg et al. |
| 9,087,369 B2 | 7/2015 | Zuo et al. |
| 9,095,264 B2 | 8/2015 | Ryu et al. |
| 9,095,715 B2 | 8/2015 | Gillberg et al. |
| 9,101,333 B2 | 8/2015 | Schwartz |
| 9,119,545 B2 | 9/2015 | Bjorling et al. |
| 9,144,685 B2 | 9/2015 | Xiao et al. |
| 9,155,897 B2 | 10/2015 | Ghosh et al. |
| 9,168,380 B1 | 10/2015 | Greenhut et al. |
| 9,186,081 B2 | 11/2015 | Afonso et al. |
| 9,241,640 B2 | 1/2016 | Greenhut et al. |
| 9,254,091 B2 | 2/2016 | Greenhut et al. |
| 9,278,229 B1 | 3/2016 | Reinke et al. |
| 9,314,205 B2 | 4/2016 | Greenhut |
| 9,352,165 B2 | 5/2016 | Zhang |
| 9,403,019 B2 | 8/2016 | Sambelashvili et al. |
| 9,408,062 B2 | 8/2016 | Davies et al. |
| 9,474,491 B2 | 10/2016 | Li et al. |
| 9,511,234 B2 | 12/2016 | Ghosh et al. |
| 9,526,435 B2 | 12/2016 | Ghosh |
| 9,526,908 B2 | 12/2016 | Zhang et al. |
| 9,538,929 B2 | 1/2017 | Yang et al. |
| 9,554,718 B2 | 1/2017 | Bar-Tal et al. |
| 9,603,651 B2 | 3/2017 | Ghosh |
| 9,604,064 B2 | 3/2017 | Ghosh et al. |
| 9,610,025 B2 | 4/2017 | Zhang |
| 9,615,764 B2 | 4/2017 | Zino et al. |
| 9,621,051 B2 | 4/2017 | Wagner |
| 9,642,674 B2 | 5/2017 | Chmiel et al. |
| 9,643,024 B2 | 5/2017 | Reinke et al. |
| 9,649,046 B2 | 5/2017 | Bar-Tal et al. |
| 9,656,087 B2 | 5/2017 | Ghosh |
| 9,662,033 B2 | 5/2017 | Severino |
| 9,668,668 B2 | 6/2017 | Gunderson et al. |
| 9,669,224 B2 | 6/2017 | Carney et al. |
| 9,675,261 B2 | 6/2017 | Cao et al. |
| 9,675,266 B2 | 6/2017 | Afonso et al. |
| 9,682,238 B2 | 6/2017 | Zhang et al. |
| 9,682,244 B2 | 6/2017 | Stadler et al. |
| 9,699,691 B2 | 7/2017 | Wang |
| 9,700,729 B2 | 7/2017 | Ghosh et al. |
| 9,717,437 B2 | 8/2017 | Cao et al. |
| 9,744,364 B2 | 8/2017 | Gordon et al. |
| 9,788,751 B2 | 10/2017 | Li et al. |
| 9,808,637 B2 | 11/2017 | Sharma et al. |
| 9,808,640 B2 | 11/2017 | Zhang |
| 9,844,675 B2 | 12/2017 | Hareland et al. |
| 9,861,817 B2 | 1/2018 | Cho et al. |
| 9,861,828 B2 | 1/2018 | Norton et al. |
| 9,867,661 B2 | 1/2018 | Werneth et al. |
| 9,872,653 B2 | 1/2018 | Li et al. |
| 9,883,918 B2 | 2/2018 | Chmiel et al. |
| 9,888,860 B2 | 2/2018 | Han et al. |
| 9,895,117 B2 | 2/2018 | Grass et al. |
| 9,943,242 B2 | 4/2018 | Yang et al. |
| 9,981,136 B2 | 5/2018 | Stadler et al. |
| 9,990,470 B2 | 6/2018 | Yang et al. |
| 9,999,775 B2 | 6/2018 | Ghosh |
| 10,015,700 B2 | 7/2018 | Wang |
| 10,039,469 B2 | 8/2018 | Higgins et al. |
| 10,045,710 B2 | 8/2018 | Higgins et al. |
| 10,045,908 B2 | 8/2018 | Aelen et al. |
| 10,046,168 B2 | 8/2018 | Nikolski et al. |
| 10,052,494 B2 | 8/2018 | Sheldon et al. |
| 10,064,586 B2 | 9/2018 | Koehler et al. |
| 10,065,045 B2 | 9/2018 | Zhang |
| 10,105,074 B2 | 10/2018 | Severino |
| 10,136,828 B2 | 11/2018 | Houben et al. |
| 10,143,424 B2 | 12/2018 | Gunderson et al. |
| 10,154,794 B2 | 12/2018 | Stadler et al. |
| 10,165,959 B2 | 1/2019 | Colbaugh et al. |
| 10,201,710 B2 | 2/2019 | Jackson et al. |
| 10,207,116 B2 | 2/2019 | Sheldon et al. |
| 10,219,718 B2 | 3/2019 | Cao et al. |
| 10,226,197 B2 | 3/2019 | Reinke et al. |
| 10,226,630 B2 | 3/2019 | Greenhut et al. |
| 10,226,639 B2 | 3/2019 | Zhang |
| 10,231,694 B2 | 3/2019 | Vajinepalli et al. |
| 10,232,182 B2 | 3/2019 | Hareland et al. |
| 10,238,309 B2 | 3/2019 | Bar-Tal et al. |
| 10,238,350 B2 | 3/2019 | Erdemir et al. |
| 10,272,248 B2 | 4/2019 | Engels et al. |
| 10,286,221 B2 | 5/2019 | Sawchuk |
| 10,314,542 B2 | 6/2019 | Bar-Tal et al. |
| 10,349,856 B2 | 7/2019 | Relan et al. |
| 10,350,425 B2 | 7/2019 | Nikolski et al. |
| 10,350,426 B2 | 7/2019 | Sheldon et al. |
| 10,362,946 B2 | 7/2019 | Greenhut |
| 10,368,769 B2 | 8/2019 | Cao et al. |
| 10,369,372 B2 | 8/2019 | Stadler et al. |
| 10,376,159 B2 | 8/2019 | Morris et al. |
| 10,376,705 B2 | 8/2019 | Zhang et al. |
| 10,433,746 B2 | 10/2019 | Ghosh et al. |
| 10,433,749 B2 | 10/2019 | Nakar et al. |
| 10,441,187 B2 | 10/2019 | Afonso et al. |
| 10,448,855 B2 | 10/2019 | Reinke et al. |
| 10,449,368 B2 | 10/2019 | Sambelashvili et al. |
| 10,500,406 B2 | 12/2019 | Zhang |
| 10,512,435 B2 | 12/2019 | Li et al. |
| 10,512,781 B2 | 12/2019 | Stadler et al. |
| 10,517,496 B2 | 12/2019 | Urman et al. |
| 10,531,914 B2 | 1/2020 | Stewart et al. |
| 10,532,212 B2 | 1/2020 | Splett et al. |
| 10,573,415 B2 | 2/2020 | Patel et al. |

(56) References Cited

U.S. PATENT DOCUMENTS

| | | |
|---|---|---|
| 10,575,748 B2 | 3/2020 | Higgins et al. |
| 10,576,263 B2 | 3/2020 | Botzer et al. |
| 10,582,872 B2 | 3/2020 | Severino |
| 10,582,894 B2 | 3/2020 | Ben et al. |
| 10,583,306 B2 | 3/2020 | Zhang et al. |
| 10,595,813 B2 | 3/2020 | Song et al. |
| 10,596,383 B2 | 3/2020 | Ghosh |
| 10,624,554 B2 | 4/2020 | Zeidan et al. |
| 10,624,557 B2 | 4/2020 | Li et al. |
| 10,674,929 B2 | 6/2020 | Houben et al. |
| 10,687,721 B2 | 6/2020 | Han et al. |
| 10,694,967 B2 | 6/2020 | Hemming et al. |
| 10,707,692 B2 | 7/2020 | Schmidt et al. |
| 10,722,320 B2 | 7/2020 | Bzostek et al. |
| 10,722,717 B2 | 7/2020 | Hareland et al. |
| 10,737,099 B2 | 8/2020 | Wasson et al. |
| 10,750,970 B2 | 8/2020 | Stadler et al. |
| 10,758,137 B2 | 9/2020 | Deno et al. |
| 10,758,147 B2 | 9/2020 | Relan et al. |
| 10,765,359 B2 | 9/2020 | Cho et al. |
| 10,765,876 B2 | 9/2020 | Nikolski |
| 10,788,595 B2 | 9/2020 | Alving et al. |
| 10,799,188 B2 | 10/2020 | Erdemir et al. |
| 10,821,292 B2 | 11/2020 | Iyer et al. |
| 10,828,494 B2 | 11/2020 | Hareland et al. |
| 10,842,400 B2 | 11/2020 | Bar-Tal et al. |
| 10,856,759 B2 | 12/2020 | Bar-Tal et al. |
| 10,857,270 B2 | 12/2020 | Pan |
| 10,864,377 B2 | 12/2020 | Sheldon et al. |
| 10,874,790 B2 | 12/2020 | Gerber et al. |
| 2011/0270107 A1 | 11/2011 | Zhang et al. |
| 2011/0270108 A1 | 11/2011 | Stadler et al. |
| 2011/0270333 A1 | 11/2011 | Stadler et al. |
| 2012/0089038 A1 | 4/2012 | Ryu et al. |
| 2012/0238892 A1 | 9/2012 | Sarkar |
| 2012/0277600 A1 | 11/2012 | Greenhut |
| 2012/0283580 A1 | 11/2012 | Havel et al. |
| 2013/0039559 A1 | 2/2013 | Grass et al. |
| 2013/0085406 A1 | 4/2013 | Gunderson et al. |
| 2013/0123773 A1 | 5/2013 | Schwartz |
| 2013/0218223 A1 | 8/2013 | Ghosh et al. |
| 2013/0218227 A1 | 8/2013 | Ghosh et al. |
| 2013/0230226 A1 | 9/2013 | Zuo et al. |
| 2013/0253349 A1 | 9/2013 | Hayam et al. |
| 2013/0289401 A1 | 10/2013 | Colbaugh et al. |
| 2014/0073876 A1 | 3/2014 | Rodriguez-Llorente et al. |
| 2014/0276158 A1 | 9/2014 | Zhang |
| 2014/0307852 A1 | 10/2014 | Grass et al. |
| 2014/0343431 A1 | 11/2014 | Vajinepalli et al. |
| 2014/0358000 A1 | 12/2014 | Gupta et al. |
| 2015/0057507 A1 | 2/2015 | Koyrakh et al. |
| 2015/0065118 A1 | 3/2015 | Davies et al. |
| 2015/0073721 A1* | 3/2015 | Briggs .................. A61B 5/349 702/19 |
| 2015/0155788 A1 | 6/2015 | Wagner |
| 2015/0223863 A1 | 8/2015 | Ghosh |
| 2015/0297907 A1 | 10/2015 | Zhang |
| 2015/0305640 A1 | 10/2015 | Reinke et al. |
| 2015/0315644 A1 | 11/2015 | Soykan et al. |
| 2015/0321011 A1 | 11/2015 | Carney et al. |
| 2015/0374579 A1 | 12/2015 | Aelen et al. |
| 2016/0045123 A1 | 2/2016 | Bar-Tal et al. |
| 2016/0051324 A1 | 2/2016 | Stewart et al. |
| 2016/0058307 A1 | 3/2016 | Svanerudh |
| 2016/0100770 A1 | 4/2016 | Afonso et al. |
| 2016/0106336 A1 | 4/2016 | Li et al. |
| 2016/0106989 A1 | 4/2016 | Stadler et al. |
| 2016/0120427 A1 | 5/2016 | Zino et al. |
| 2016/0157785 A1 | 6/2016 | Merritt et al. |
| 2016/0175603 A1 | 6/2016 | Sheldon et al. |
| 2016/0213270 A1 | 7/2016 | Cao et al. |
| 2016/0287191 A1 | 10/2016 | Koehler et al. |
| 2016/0287349 A1 | 10/2016 | Bzostek et al. |
| 2016/0324485 A1 | 11/2016 | Erdemir et al. |
| 2017/0014086 A1 | 1/2017 | Li et al. |
| 2017/0071493 A1 | 3/2017 | Yang et al. |
| 2017/0079539 A1 | 3/2017 | Chauhan et al. |
| 2017/0095173 A1 | 4/2017 | Bar-Tal et al. |
| 2017/0189134 A1 | 7/2017 | Chmiel et al. |
| 2017/0202470 A1 | 7/2017 | Urman et al. |
| 2017/0202471 A1 | 7/2017 | Urman et al. |
| 2017/0202472 A1 | 7/2017 | Zeidan et al. |
| 2017/0202515 A1 | 7/2017 | Zrihem et al. |
| 2017/0202516 A1 | 7/2017 | Bar-Tal et al. |
| 2017/0202521 A1 | 7/2017 | Urman et al. |
| 2017/0203114 A1 | 7/2017 | Zhang |
| 2017/0209108 A1 | 7/2017 | Grass et al. |
| 2017/0231517 A1 | 8/2017 | Severino |
| 2017/0266442 A1 | 9/2017 | Jackson |
| 2017/0272982 A1 | 9/2017 | Wang |
| 2017/0281031 A1 | 10/2017 | Houben et al. |
| 2017/0281033 A1 | 10/2017 | Higgins et al. |
| 2017/0312514 A1 | 11/2017 | Hareland et al. |
| 2017/0312516 A1 | 11/2017 | Jackson et al. |
| 2017/0312531 A1 | 11/2017 | Sawchuk |
| 2017/0340887 A1 | 11/2017 | Engels et al. |
| 2018/0028814 A1 | 2/2018 | Ghosh |
| 2018/0042510 A1 | 2/2018 | Nakar et al. |
| 2018/0085589 A1 | 3/2018 | Splett et al. |
| 2018/0098810 A1 | 4/2018 | Werneth et al. |
| 2018/0154154 A1 | 6/2018 | Sheldon et al. |
| 2018/0168463 A1 | 6/2018 | Morris et al. |
| 2018/0168502 A1 | 6/2018 | Cho et al. |
| 2018/0185640 A1 | 7/2018 | Hareland et al. |
| 2018/0206750 A1 | 7/2018 | Pappone et al. |
| 2018/0206920 A1 | 7/2018 | Pappone et al. |
| 2018/0206921 A1 | 7/2018 | Pappone et al. |
| 2018/0207437 A1 | 7/2018 | Zhang et al. |
| 2018/0214695 A1 | 8/2018 | Grenz et al. |
| 2018/0221078 A1 | 8/2018 | Howard et al. |
| 2018/0264258 A1 | 9/2018 | Cheng et al. |
| 2018/0279895 A1 | 10/2018 | Relan et al. |
| 2018/0280683 A1 | 10/2018 | Botzer et al. |
| 2018/0289276 A1 | 10/2018 | Relan et al. |
| 2018/0303985 A1 | 10/2018 | Pan |
| 2018/0333586 A1 | 11/2018 | Wasson et al. |
| 2018/0350469 A1 | 12/2018 | Yang et al. |
| 2019/0015003 A1 | 1/2019 | Auerbach et al. |
| 2019/0017120 A1 | 1/2019 | Soykan et al. |
| 2019/0038165 A1 | 2/2019 | Relan et al. |
| 2019/0056517 A1 | 2/2019 | Alving et al. |
| 2019/0108650 A1 | 4/2019 | De et al. |
| 2019/0117104 A1 | 4/2019 | Stadler et al. |
| 2019/0160290 A1 | 5/2019 | Roberts et al. |
| 2019/0160291 A1 | 5/2019 | Peichel et al. |
| 2019/0160292 A1 | 5/2019 | Peichel et al. |
| 2019/0160293 A1 | 5/2019 | Reinke et al. |
| 2019/0167137 A1 | 6/2019 | Bar-Tal et al. |
| 2019/0167994 A1 | 6/2019 | Jackson et al. |
| 2019/0175918 A1 | 6/2019 | Grenz et al. |
| 2019/0183374 A1 | 6/2019 | Reinke et al. |
| 2019/0184181 A1 | 6/2019 | Zhao et al. |
| 2019/0188909 A1 | 6/2019 | Yellin et al. |
| 2019/0192020 A1 | 6/2019 | Cao et al. |
| 2019/0209845 A1 | 7/2019 | Stadler et al. |
| 2019/0209846 A1 | 7/2019 | Stadler et al. |
| 2019/0223808 A1 | 7/2019 | Rubinstein et al. |
| 2019/0247669 A1 | 8/2019 | Nielsen et al. |
| 2019/0262624 A1 | 8/2019 | Sawchuk |
| 2019/0307344 A1 | 10/2019 | Markovitz et al. |
| 2019/0336767 A1 | 11/2019 | Klepfer et al. |
| 2019/0336780 A1 | 11/2019 | Sheldon et al. |
| 2019/0350467 A1 | 11/2019 | Greenhut |
| 2019/0350477 A1 | 11/2019 | Han et al. |
| 2019/0351246 A1 | 11/2019 | Stadler et al. |
| 2019/0357791 A1 | 11/2019 | Zeidan et al. |
| 2019/0357795 A1 | 11/2019 | Cao et al. |
| 2019/0365262 A1 | 12/2019 | Honicker |
| 2019/0374125 A1 | 12/2019 | Nakar et al. |
| 2019/0374783 A1 | 12/2019 | Zhang et al. |
| 2020/0001095 A1 | 1/2020 | Iyer et al. |
| 2020/0005988 A1 | 1/2020 | Iyer et al. |
| 2020/0046984 A1 | 2/2020 | Sambelashvili et al. |
| 2020/0060567 A1 | 2/2020 | Zeidan et al. |

(56) References Cited

U.S. PATENT DOCUMENTS

| | | |
|---|---|---|
| 2020/0060568 A1 | 2/2020 | Katz et al. |
| 2020/0077908 A1 | 3/2020 | Hagfors et al. |
| 2020/0094015 A1 | 3/2020 | Colbaugh et al. |
| 2020/0107879 A1 | 4/2020 | Stewart et al. |
| 2020/0108243 A1 | 4/2020 | Botzer et al. |
| 2020/0114157 A1 | 4/2020 | Zhang |
| 2020/0121261 A1 | 4/2020 | Li et al. |
| 2020/0121932 A1 | 4/2020 | Splett et al. |
| 2020/0146572 A1 | 5/2020 | Bar-Tal et al. |
| 2020/0146579 A1 | 5/2020 | Bar-Tal et al. |
| 2020/0146580 A1 | 5/2020 | Sarkar et al. |
| 2020/0155742 A1 | 5/2020 | Stadler |
| 2020/0163582 A1 | 5/2020 | Hayam et al. |
| 2020/0178831 A1 | 6/2020 | Ziv-Ari et al. |
| 2020/0179701 A1 | 6/2020 | Pronovici et al. |
| 2020/0179707 A1 | 6/2020 | Splett et al. |
| 2020/0179708 A1 | 6/2020 | Splett et al. |
| 2020/0196889 A1 | 6/2020 | Govari |
| 2020/0196899 A1 | 6/2020 | Higgins et al. |
| 2020/0205686 A1 | 7/2020 | Severino |
| 2020/0214588 A1 | 7/2020 | Li et al. |
| 2020/0230420 A1 | 7/2020 | Warman |
| 2020/0237245 A1 | 7/2020 | Han et al. |
| 2020/0245888 A1 | 8/2020 | Zeidan et al. |
| 2020/0254262 A1 | 8/2020 | Demmer et al. |
| 2020/0281491 A1 | 9/2020 | Han et al. |
| 2020/0281493 A1 | 9/2020 | Nguyen et al. |
| 2020/0286224 A1 | 9/2020 | Grass et al. |
| 2020/0297234 A1 | 9/2020 | Houben et al. |
| 2020/0297281 A1 | 9/2020 | Basu et al. |
| 2020/0297418 A1 | 9/2020 | Stewart et al. |
| 2020/0315481 A1 | 10/2020 | Hemming et al. |
| 2020/0315484 A1 | 10/2020 | Deno et al. |
| 2020/0323456 A1 | 10/2020 | Nguyen et al. |
| 2020/0324118 A1 | 10/2020 | Garner et al. |
| 2020/0328615 A1 | 10/2020 | Schmidt et al. |
| 2020/0352652 A1 | 11/2020 | Amit et al. |
| 2020/0352677 A1 | 11/2020 | Bzostek et al. |
| 2020/0359959 A1 | 11/2020 | Cho et al. |
| 2020/0367778 A1 | 11/2020 | Zar et al. |
| 2020/0383596 A1 | 12/2020 | Stadler et al. |
| 2020/0398067 A1 | 12/2020 | Nikolski |
| 2021/0001031 A1 | 1/2021 | Gerber et al. |
| 2021/0068790 A1 | 3/2021 | Dufour et al. |
| 2021/0077075 A1 | 3/2021 | Kolen et al. |
| 2021/0128245 A1 | 5/2021 | Pappone et al. |
| 2021/0137440 A1 | 5/2021 | Mangual-Soto |
| 2021/0194284 A1 | 6/2021 | Van et al. |
| 2021/0225523 A1 | 7/2021 | Yang et al. |
| 2021/0228138 A1 | 7/2021 | Urman et al. |
| 2021/0316149 A1 | 10/2021 | Peichel et al. |
| 2022/0095984 A1 | 3/2022 | Bennett et al. |
| 2022/0133389 A1 | 5/2022 | Howard et al. |
| 2022/0249030 A1 | 8/2022 | Rubinstein et al. |
| 2022/0257127 A1 | 8/2022 | Svanerudh |

FOREIGN PATENT DOCUMENTS

| | | |
|---|---|---|
| EP | 2567359 B1 | 10/2014 |
| EP | 2790585 A1 | 10/2014 |
| EP | 2591722 B1 | 12/2014 |
| EP | 2809394 A2 | 12/2014 |
| EP | 2704795 B1 | 1/2015 |
| EP | 2621336 B1 | 7/2015 |
| EP | 2701582 B1 | 7/2015 |
| EP | 2967384 A1 | 1/2016 |
| EP | 2958484 B1 | 8/2016 |
| EP | 3048952 A1 | 8/2016 |
| EP | 2563467 B1 | 9/2016 |
| EP | 2563468 B1 | 10/2016 |
| EP | 3085303 A1 | 10/2016 |
| EP | 2629661 B1 | 12/2016 |
| EP | 2862265 B1 | 2/2017 |
| EP | 3125996 A1 | 2/2017 |
| EP | 3128907 A1 | 2/2017 |
| EP | 2567585 B1 | 3/2017 |
| EP | 3134181 A1 | 3/2017 |
| EP | 2563216 B1 | 4/2017 |
| EP | 2685886 B1 | 5/2017 |
| EP | 2775924 B1 | 5/2017 |
| EP | 3192441 A1 | 7/2017 |
| EP | 3192442 A1 | 7/2017 |
| EP | 3192444 A1 | 7/2017 |
| EP | 3192445 A1 | 7/2017 |
| EP | 2641534 B1 | 8/2017 |
| EP | 3209196 A1 | 8/2017 |
| EP | 3209378 A1 | 8/2017 |
| EP | 3229658 A1 | 10/2017 |
| EP | 3082606 B1 | 11/2017 |
| EP | 3133999 B1 | 12/2017 |
| EP | 2598202 B1 | 1/2018 |
| EP | 3021746 B1 | 1/2018 |
| EP | 3277194 A1 | 2/2018 |
| EP | 3281579 A1 | 2/2018 |
| EP | 3133989 B1 | 4/2018 |
| EP | 2958535 B1 | 5/2018 |
| EP | 3015060 B1 | 5/2018 |
| EP | 3331604 A1 | 6/2018 |
| EP | 3334494 A1 | 6/2018 |
| EP | 3166483 B1 | 8/2018 |
| EP | 3354192 A1 | 8/2018 |
| EP | 3355310 A1 | 8/2018 |
| EP | 2984986 B1 | 10/2018 |
| EP | 3383488 A1 | 10/2018 |
| EP | 3384835 A1 | 10/2018 |
| EP | 3236837 B1 | 11/2018 |
| EP | 2986206 B1 | 12/2018 |
| EP | 3171936 B1 | 12/2018 |
| EP | 3420722 A1 | 1/2019 |
| EP | 3427643 A1 | 1/2019 |
| EP | 3435856 A1 | 2/2019 |
| EP | 3435857 A1 | 2/2019 |
| EP | 3440660 A1 | 2/2019 |
| EP | 3164189 B1 | 3/2019 |
| EP | 3185764 B1 | 3/2019 |
| EP | 3448509 A1 | 3/2019 |
| EP | 3448511 A1 | 3/2019 |
| EP | 3021745 B1 | 4/2019 |
| EP | 3370796 B1 | 4/2019 |
| EP | 3420629 B1 | 6/2019 |
| EP | 3490448 A1 | 6/2019 |
| EP | 3490665 A1 | 6/2019 |
| EP | 3501387 A1 | 6/2019 |
| EP | 3192443 B1 | 7/2019 |
| EP | 3225161 B1 | 7/2019 |
| EP | 3192438 B1 | 8/2019 |
| EP | 3519041 A1 | 8/2019 |
| EP | 3526798 A1 | 8/2019 |
| EP | 3206576 B1 | 9/2019 |
| EP | 3536230 A1 | 9/2019 |
| EP | 2594099 B1 | 10/2019 |
| EP | 2760333 B1 | 10/2019 |
| EP | 2848191 B1 | 10/2019 |
| EP | 3548141 A1 | 10/2019 |
| EP | 3551064 A1 | 10/2019 |
| EP | 3551065 A1 | 10/2019 |
| EP | 3554340 A1 | 10/2019 |
| EP | 3559952 A1 | 10/2019 |
| EP | 2790588 B1 | 11/2019 |
| EP | 3571985 A1 | 11/2019 |
| EP | 3344124 B1 | 12/2019 |
| EP | 3344135 B1 | 12/2019 |
| EP | 3429686 B1 | 12/2019 |
| EP | 3573704 A1 | 12/2019 |
| EP | 3573711 A1 | 12/2019 |
| EP | 3573712 A1 | 12/2019 |
| EP | 3579775 A1 | 12/2019 |
| EP | 2627243 B1 | 1/2020 |
| EP | 3140429 B1 | 2/2020 |
| EP | 3448506 B1 | 2/2020 |
| EP | 3609388 A1 | 2/2020 |
| EP | 3613342 A1 | 2/2020 |
| EP | 3383257 B1 | 3/2020 |
| EP | 3616610 A1 | 3/2020 |

(56) References Cited

FOREIGN PATENT DOCUMENTS

| | | |
|---|---|---|
| EP | 3624892 A1 | 3/2020 |
| EP | 3626164 A1 | 3/2020 |
| EP | 2814566 B1 | 4/2020 |
| EP | 2901953 B1 | 4/2020 |
| EP | 3639736 A1 | 4/2020 |
| EP | 3131626 B1 | 5/2020 |
| EP | 3134175 B1 | 5/2020 |
| EP | 3209201 B1 | 5/2020 |
| EP | 3649930 A1 | 5/2020 |
| EP | 3649931 A1 | 5/2020 |
| EP | 3656290 A1 | 5/2020 |
| EP | 3656329 A1 | 5/2020 |
| EP | 3140001 B1 | 6/2020 |
| EP | 3209373 B1 | 6/2020 |
| EP | 3666181 A1 | 6/2020 |
| EP | 3669767 A1 | 6/2020 |
| EP | 2640272 B1 | 7/2020 |
| EP | 3344136 B1 | 7/2020 |
| EP | 3681403 A1 | 7/2020 |
| EP | 3684256 A1 | 7/2020 |
| EP | 3125997 B1 | 8/2020 |
| EP | 3261531 B1 | 8/2020 |
| EP | 3697496 A1 | 8/2020 |
| EP | 3698747 A2 | 8/2020 |
| EP | 3281657 B1 | 9/2020 |
| EP | 3463563 B1 | 9/2020 |
| EP | 3703555 A1 | 9/2020 |
| EP | 3448499 B1 | 10/2020 |
| EP | 3717061 A1 | 10/2020 |
| EP | 3717062 A1 | 10/2020 |
| EP | 3717065 A1 | 10/2020 |
| EP | 3720355 A1 | 10/2020 |
| EP | 3723098 A1 | 10/2020 |
| EP | 3723848 A1 | 10/2020 |
| EP | 3725220 A1 | 10/2020 |
| EP | 3247453 B1 | 11/2020 |
| EP | 3513710 B1 | 11/2020 |
| EP | 3735180 A1 | 11/2020 |
| EP | 3737460 A1 | 11/2020 |
| EP | 3737461 A1 | 11/2020 |
| EP | 3576618 B1 | 12/2020 |
| EP | 3744240 A1 | 12/2020 |
| EP | 3744282 A2 | 12/2020 |
| EP | 3749412 A1 | 12/2020 |
| JP | 2014-502556 A | 2/2014 |
| JP | 2016-530053 A | 9/2016 |
| NO | 2020/118039 A1 | 6/2020 |
| WO | 2011/136949 A1 | 11/2011 |
| WO | 2013/116145 A2 | 8/2013 |
| WO | 2014/158840 A1 | 10/2014 |
| WO | 2015/047548 A1 | 4/2015 |
| WO | 2015/149153 A1 | 10/2015 |
| WO | 2015/153456 A1 | 10/2015 |
| WO | 2015/153459 A1 | 10/2015 |
| WO | 2015/157537 A1 | 10/2015 |
| WO | 2015/164172 A1 | 10/2015 |
| WO | 2016/064577 A1 | 4/2016 |
| WO | 2016/064963 A1 | 4/2016 |
| WO | 2016/064964 A1 | 4/2016 |
| WO | 2017/027272 A1 | 2/2017 |
| WO | 2017/096136 A1 | 6/2017 |
| WO | 2017/144387 A1 | 8/2017 |
| WO | 2017/144474 A1 | 8/2017 |
| WO | 2017/151347 A1 | 9/2017 |
| WO | 2017/160507 A1 | 9/2017 |
| WO | 2017/172271 A1 | 10/2017 |
| WO | 2017/172272 A1 | 10/2017 |
| WO | 2017/174735 A1 | 10/2017 |
| WO | 2017/189484 A1 | 11/2017 |
| WO | 2017/189664 A1 | 11/2017 |
| WO | 2017/189676 A1 | 11/2017 |
| WO | 2017/189800 A1 | 11/2017 |
| WO | 2017/210344 A1 | 12/2017 |
| WO | 2018/022558 A1 | 2/2018 |
| WO | 2018/022861 A1 | 2/2018 |
| WO | 2018/064533 A1 | 4/2018 |
| WO | 2018/094063 A1 | 5/2018 |
| WO | 2018/102639 A1 | 6/2018 |
| WO | 2018/111754 A1 | 6/2018 |
| WO | 2018/118865 A1 | 6/2018 |
| WO | 2018/134150 A1 | 7/2018 |
| WO | 2018/140343 A1 | 8/2018 |
| WO | 2018/140347 A1 | 8/2018 |
| WO | 2018/140453 A1 | 8/2018 |
| WO | 2018/148023 A1 | 8/2018 |
| WO | 2018/148026 A1 | 8/2018 |
| WO | 2018/148053 A1 | 8/2018 |
| WO | 2018/191686 A1 | 10/2018 |
| WO | 2018/213548 A1 | 11/2018 |
| WO | 2018/234427 A1 | 12/2018 |
| WO | 2019/009967 A1 | 1/2019 |
| WO | 2019/052965 A1 | 3/2019 |
| WO | 2019/057863 A1 | 3/2019 |
| WO | 2019/079377 A1 | 4/2019 |
| WO | 2019/089453 A1 | 5/2019 |
| WO | 2019/108581 A1 | 6/2019 |
| WO | 2019/108742 A1 | 6/2019 |
| WO | 2019/108765 A1 | 6/2019 |
| WO | 2019/108787 A1 | 6/2019 |
| WO | 2019/113467 A1 | 6/2019 |
| WO | 2019/118807 A1 | 6/2019 |
| WO | 2019/134959 A1 | 7/2019 |
| WO | 2019/139881 A1 | 7/2019 |
| WO | 2019/140094 A1 | 7/2019 |
| WO | 2019/156769 A1 | 8/2019 |
| WO | 2019/195425 A1 | 10/2019 |
| WO | 2019/209541 A1 | 10/2019 |
| WO | 2019/213190 A1 | 11/2019 |
| WO | 2020/006331 A1 | 1/2020 |
| WO | 2020/006332 A1 | 1/2020 |
| WO | 2020/006334 A1 | 1/2020 |
| WO | 2020/006361 A1 | 1/2020 |
| WO | 2020/064736 A1 | 4/2020 |
| WO | 2020/096689 A1 | 5/2020 |
| WO | 2020/102080 A2 | 5/2020 |
| WO | 2020/102133 A1 | 5/2020 |
| WO | 2020/118015 A1 | 6/2020 |
| WO | 2020/118037 A2 | 6/2020 |
| WO | 2020/154157 A1 | 7/2020 |
| WO | 2020/167900 A1 | 8/2020 |
| WO | 2020/188351 A1 | 9/2020 |
| WO | 2020/212551 A1 | 10/2020 |
| WO | 2020/214439 A1 | 10/2020 |
| WO | 2020/216694 A1 | 10/2020 |
| WO | 2020/219513 A1 | 10/2020 |
| WO | 2020/242940 A1 | 12/2020 |

OTHER PUBLICATIONS

Honarbakhsh et al, 'Characterization of drivers maintaining atrial fibrillation: Correlation with markers of rapidity and organization on spectral analysis', Heart Rhythm 15(9: 2018), pp. 1296-1303.

International Search Report and Written Opinion received for PCT Patent Application No. PCT/US2021/052582, mailed on Jan. 11, 2022, 11 pages.

International Search Report and Written Opinion received for PCT Patent Application No. PCT/US2021/052585, mailed on Jan. 28, 2022, 12 pages.

Pappone et al, 'Clinical Outcome of Electrophysiologically Guided Ablation for Nonparoxysmal Atrial Fibrillation Using a Novel Real-Time 3-Dimensional Mapping Technique—Results From a Prospective Randomized Trial', Circ Arrhythm Electrophysiol., 2018; 11:e005904.

Passariello. G. et al., "Real-Time Detection and Quantification of Ischemic ECG Changes," Proceedings of the Annual Conference of the Engineering in Medicine and Biology Society. Philadelphia, vol. 12, 1990, pp. 809-810.

Ravelli et al, 'Wave similarity mapping shows the spatiotemporal distribution of fibrillatory wave complexity in the human right atrium during paroxysmal and chronic atrial fibrillation', J. Cardiovasc. Electrophysiol., 16(10: 2005), pp. 1071-1076.

(56) References Cited

OTHER PUBLICATIONS

Ravelli, F and Masè, M, 'A time-domain approach for the identification of atrial fibrillation drivers', 2011 Annual Internation Conference of the IEEE Engineering in Medicine and Biology Society, 2011, DOI: 10.1109/IEMBS.2011.6091410.
Seitz et al, 'AF Ablation Guided by Spatiotemporal Electrogram Dispersion Without Pulmonary Vein Isolation—A Wholly Patient-Tailored Approach', JACC 69(3: 2017), pp. 303-321.
Willems et al, 'Targeting Nonpulmonary Vein Sources in Persistent Atrial Fibrillation Identified by Noncontact Charge Density Mapping—Uncover AF Trial', Circ Arrhythm Electrophysiol., 2019;12:e007233.

* cited by examiner

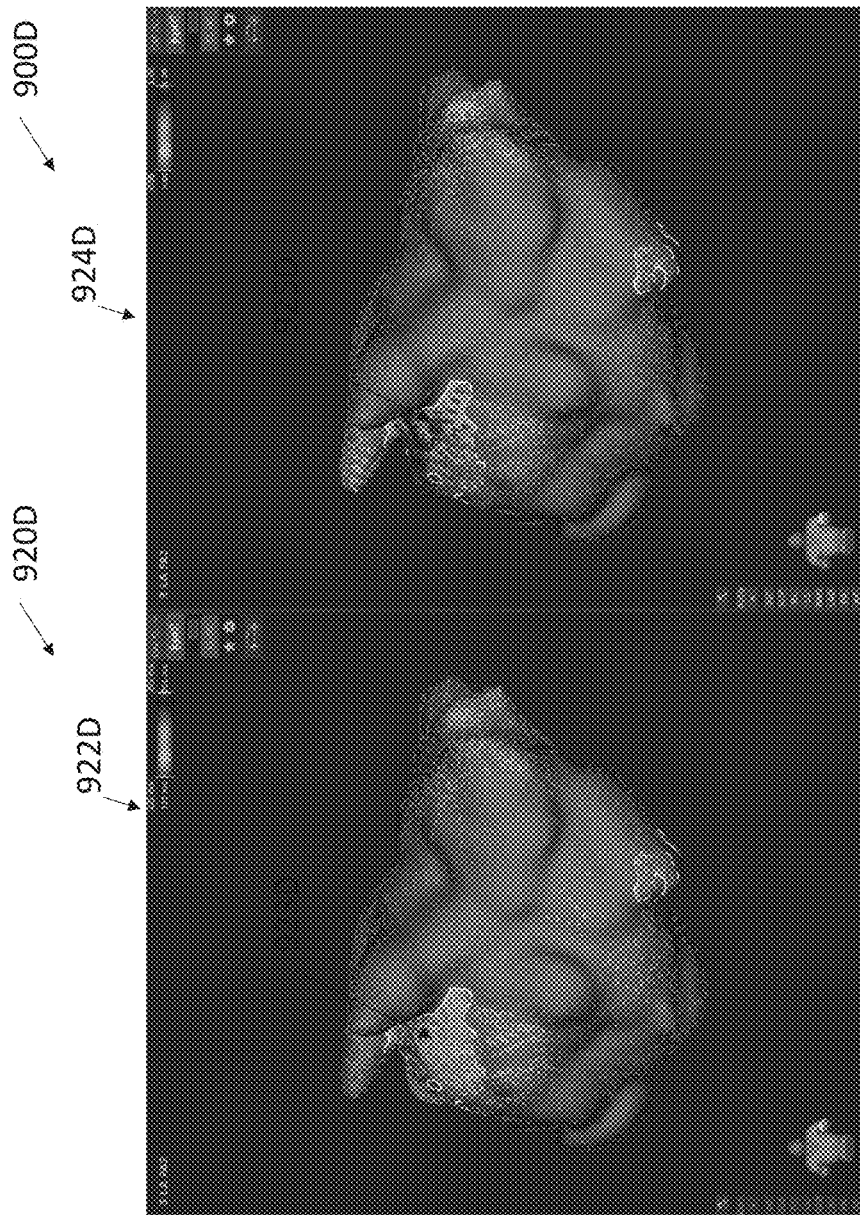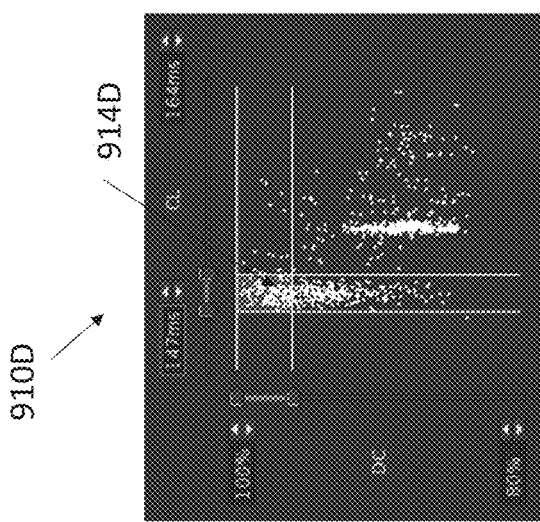
FIG. 9D

INTERACTIVE 2D SCATTER PLOT OF EGM CHARACTERISTIC METRICS

CROSS REFERENCE TO RELATED APPLICATION

This application claims priority to Provisional Application No. 63/085,659, filed Sep. 30, 2020, which is herein incorporated by reference in its entirety.

TECHNICAL FIELD

The present disclosure relates to electrophysiology systems and methods for processing cardiac electrical signals and cardiac mapping.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping, a catheter with one or more electrodes can be inserted into the patient's heart chamber.

Conventional three-dimensional (3D) mapping techniques include contact mapping, non-contact mapping, and a combination of contact and non-contact mapping. In both contact and non-contact mapping, one or more catheters are advanced into the heart. With some catheters, once in the chamber, the catheter may be deployed to assume a 3D shape. In contact mapping, physiological signals resulting from the electrical activity of the heart are acquired with one or more electrodes located at the catheter distal tip after determining that the tip is in stable and steady contact with the endocardium surface of a particular heart chamber. In non-contact-based mapping systems, using the signals detected by the non-contact electrodes and information on chamber anatomy and relative electrode location, the system provides physiological information regarding the endocardium of the heart chamber. Location and electrical activity are usually measured sequentially on a point-by-point basis at about 50 to 200 points on the internal surface of the heart to construct an electro-anatomical depiction of the heart. The generated map may then serve as the basis for deciding on a therapeutic course of action, for example, tissue ablation, to alter the propagation of the heart's electrical activity and to restore normal heart rhythm.

In many conventional mapping systems, the clinician visually inspects or examines the captured electrograms (EGMs), which increases examination time and cost. During an automatic electro-anatomical mapping process, however, approximately 6,000 to 20,000 intracardiac electrograms (EGMs) may be captured, which does not lend itself to being manually inspected in full by a clinician (e.g., a physician) for a diagnostic assessment, EGM categorization, and/or the like. Typically mapping systems extract scalar values from each EGM to construct voltage, activation, or other map types to depict overall patterns of activity within the heart. While maps reduce the need to inspect the captured EGMs, they also condense the often complex and useful information in the EGMs. Further, maps may be misleading due to electrical artifacts or inappropriate selection of features such as activation times. Additionally, due to the complex nature of conventional techniques, cardiac maps often are not suitable for accurate and efficient interpretation.

SUMMARY

As recited in examples, Example 1 is a method of processing cardiac information. The method comprises the steps of: receiving an activation waveform comprising a set of activation waveform data of a plurality of signal sections collected at a plurality of locations; receiving a set of window parameters comprising a range of window size. For each of the plurality of signal sections, the method comprises the steps of: determining a set of confidence values, each confidence value corresponding to a window size, by iterating through a plurality of window sizes in the range of window size. Additionally, for each of the plurality of signal sections, the method comprises the steps of: for each window size of the plurality of window sizes, selecting a position of a central window, the central window having the each window size; calculating a set of correlations, each of the set of correlations being a correlation of the activation waveform in the central window and the activation waveform in a shifted window, the shifted window being a sample window shifted from the central window and having the each window size; and determining one of the set of confidence values based on the set of correlations. For each of the plurality of signal sections, the method further comprises the steps of: comparing the set of confidence values to select a designated confidence value and a selected window size corresponding to the designated confidence value; and determining one of a plurality of local cycle lengths for the each of the plurality of signal sections based on the selected window size. The method further comprises generating a representation of the plurality of local cycle lengths.

Example 2 is the method of Example 1, wherein the representation is at least one of a histogram, a scatter plot, and a graphical representation of the plurality of local cycle lengths overlaid on a cardiac map.

Example 3 is the method of Example 1 or 2, further comprising: receiving an input of a parameter of the representation of the plurality of local cycle lengths; and adjusting the representation of the plurality of local cycle lengths based on the input.

Example 4 is the method of any one of Examples 1-3, wherein the plurality of locations are selected based on an input.

Example 5 is the method of Example 2, wherein the input indicates a probe location in the heart chamber, and wherein the plurality of locations are within a predetermined radius from the probe location.

Example 6 is the method of any one of Examples 1-5, wherein the set of correlations comprise a set of backward correlations and a set of forward correlations, wherein each of the set of backward correlations is a correlation of the central window and a backward shifted window, wherein the backward shifted window is the central window shifted backward, wherein each of the set of forward correlations is a correlation of the central window and a forward shifted window, wherein the forward shifted window is the central window shifted forward.

Example 7 is the method of any one of Examples 1-6, further comprising: for each signal section of the plurality signal sections, determining one of a plurality local duty cycles based on the activation waveform of a selected central window having the selected window size, wherein the selected central window is corresponding to the designated confidence value.

Example 8 is the method of Example 7, further comprising: generating a representation of the plurality of duty cycles, wherein the representation is at least one of a histogram, a scatter plot and a graphical representation of the plurality of local duty cycles overlaid on a cardiac map.

Example 9 is the method of Example 8, further comprising: receiving an input of a parameter of the representation of the plurality local duty cycles; and adjusting the representation of the plurality local duty cycles based on the input.

Example 10 is the method of any one of Examples 1-9, further comprising: for each signal section of the plurality of signal sections, determining one of a plurality of section confidence values based on the set of confidence values.

Example 11 is the method of Example 10, further comprising: generating a representation of the plurality of section confidence values, wherein the representation is at least one of a histogram, a scatter plot and a graphical representation of the plurality of local duty cycles overlaid on a cardiac map.

Example 12 is a system for processing cardiac information. The system comprises a processing unit configured to: receive an activation waveform comprising a set of activation waveform data of a plurality of signal sections collected at a plurality of locations; receive a set of window parameters comprising a range of window size. For each of the plurality of signal sections, the processing unit is further configured to: determine a set of confidence values, each confidence value corresponding to a window size, by iterating through a plurality of window sizes in the range of window size. Additionally, for each of the plurality of signal sections, the processing unit is further configured to: for each window size of the plurality of window sizes, select a position of a central window, the central window having the each window size; calculate a set of correlations, each of the set of correlations being a correlation of the activation waveform in the central window and the activation waveform in a shifted window, the shifted window being a sample window shifted from the central window and having the each window size; and determine one of the set of confidence values based on the set of correlations. For each of the plurality of signal sections, the processing unit is further configured to: compare the set of confidence values to select a designated confidence value and a selected window size corresponding to the designated confidence value; and determine one of a plurality of local cycle lengths for the each of the plurality of signal sections based on the selected window size. The processing unit is further configured to generate a representation of the plurality of local cycle lengths.

Example 13 is the system of Example 12, wherein the representation is at least one of a histogram, a scatter plot, and a graphical representation of the plurality of local cycle lengths overlaid on a cardiac map.

Example 14 is the system of Example 12 or 13, the processing unit is further configured to: receive an input of a parameter of the representation of the plurality of local cycle lengths; and adjust the representation of the plurality of local cycle lengths based on the input.

Example 15 is the system of Example 14, wherein the input indicates a probe location in the heart chamber, and wherein the plurality of locations are within a predetermined radius from the probe location.

Example 16 is a method of processing cardiac information. The method comprises the steps of: receiving an activation waveform comprising a set of activation waveform data of a plurality of signal sections collected at a plurality of locations; receiving a set of window parameters comprising a range of window size. For each of the plurality of signal sections, the method comprises the steps of: determining a set of confidence values, each confidence value corresponding to a window size, by iterating through a plurality of window sizes in the range of window size. Additionally, for each of the plurality of signal sections, the method comprises the steps of: for each window size of the plurality of window sizes, selecting a position of a central window, the central window having the each window size; calculating a set of correlations, each of the set of correlations being a correlation of the activation waveform in the central window and the activation waveform in a shifted window, the shifted window being a sample window shifted from the central window and having the each window size; and determining one of the set of confidence values based on the set of correlations. For each of the plurality of signal sections, the method further comprises the steps of: comparing the set of confidence values to select a designated confidence value and a selected window size corresponding to the designated confidence value; and determining one of a plurality of local cycle lengths for the each of the plurality of signal sections based on the selected window size. The method further comprises generating a representation of the plurality of local cycle lengths.

Example 17 is the method of Example 16, wherein the representation is at least one of a histogram, a scatter plot, and a graphical representation of the plurality of local cycle lengths overlaid on a cardiac map.

Example 18 is the method of Example 16, further comprising: receiving an input of a parameter of the representation of the plurality of local cycle lengths; and adjusting the representation of the plurality of local cycle lengths based on the input.

Example 19 is the method of Example 16, wherein the plurality of locations are selected based on an input.

Example 20 is the method of Example 19, wherein the input indicates a probe location in the heart chamber, and wherein the plurality of locations are within a predetermined radius from the probe location.

Example 21 is the method of Example 16, further comprising: for each signal section of the plurality signal sections, determining one of a plurality local duty cycles based on the activation waveform of a selected central window having the selected window size, wherein the selected central window is corresponding to the designated confidence value.

Example 22 is the method of Example 21, further comprising: generating a representation of the plurality of duty cycles, wherein the representation is at least one of a histogram, a scatter plot and a graphical representation of the plurality of local duty cycles overlaid on a cardiac map.

Example 23 is the method of Example 21, further comprising: receiving an input of a parameter of the representation of the plurality local duty cycles; and adjusting the representation of the plurality local duty cycles based on the input.

Example 24 is the method of Example 16, further comprising: for each signal section of the plurality of signal sections, determining one of a plurality of section confidence values based on the set of confidence values.

Example 25 is the method of Example 24, further comprising: for each signal section of the plurality of signal sections, determining one of a plurality of section confidence values based on the designated backward confidence value, the designated forward confidence value, the selected backward window size, and the selected forward window size.

Example 26 is the method of Example 24, wherein each of the set of confidence values is based on an amplitude of the activation waveform in the central window of the selected window size and the set of correlations.

Example 27 is the method of Example 24, further comprising: generating a representation of the plurality of section confidence values, wherein the representation is at least one of a histogram, a scatter plot and a graphical representation of the plurality of local duty cycles overlaid on a cardiac map.

Example 28 is the method of Example 27, further comprising: receiving an input of a parameter of the representation of the plurality section confidence values; and adjusting the representation of the plurality section confidence values based on the input.

Example 29 is the method of Example 16, further comprising: generating a representation of the set of annotation waveform data overlaid on a cardiac map; receiving an input associated with the plurality of local cycle lengths; updating the annotation waveform based on the input; and updating the representation of the set of annotation waveform data overlaid on the cardiac map.

Example 30 is a system for processing cardiac information. The system comprises a processing unit configured to: receive an activation waveform comprising a set of activation waveform data of a plurality of signal sections collected at a plurality of locations; receive a set of window parameters comprising a range of window size. For each of the plurality of signal sections, the processing unit is further configured to: determine a set of confidence values, each confidence value corresponding to a window size, by iterating through a plurality of window sizes in the range of window size. Additionally, for each of the plurality of signal sections, the processing unit is further configured to: for each window size of the plurality of window sizes, select a position of a central window, the central window having the each window size; calculate a set of correlations, each of the set of correlations being a correlation of the activation waveform in the central window and the activation waveform in a shifted window, the shifted window being a sample window shifted from the central window and having the each window size; and determine one of the set of confidence values based on the set of correlations. For each of the plurality of signal sections, the processing unit is further configured to: compare the set of confidence values to select a designated confidence value and a selected window size corresponding to the designated confidence value; and determine one of a plurality of local cycle lengths for the each of the plurality of signal sections based on the selected window size. The processing unit is further configured to generate a representation of the plurality of local cycle lengths.

Example 31 is the system of Example 30, wherein the representation is at least one of a histogram, a scatter plot, and a graphical representation of the plurality of local cycle lengths overlaid on a cardiac map.

Example 32 is the system of Example 30, the processing unit is further configured to: receive an input of a parameter of the representation of the plurality of local cycle lengths; and adjust the representation of the plurality of local cycle lengths based on the input.

Example 33 is the system of Example 32, wherein the input indicates a probe location in the heart chamber, and wherein the plurality of locations are within a predetermined radius from the probe location.

Example 34 is the system of Example 30, further comprising: for each signal section of the plurality signal sections, determining one of a plurality local duty cycles based on the activation waveform of a selected central window having the selected window size, wherein the selected central window is corresponding to the designated confidence value.

Example 35 is the system of Example 34, further comprising: generating a representation of the plurality of duty cycles, wherein the representation is at least one of a histogram, a scatter plot and a graphical representation of the plurality of local duty cycles overlaid on a cardiac map.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 5I depicts an illustrative example of a maximum waveform.

FIG. 9D depicts one illustrative example of a graphical representation having a scatter plot and one or more cardiac maps.

Figure 1:
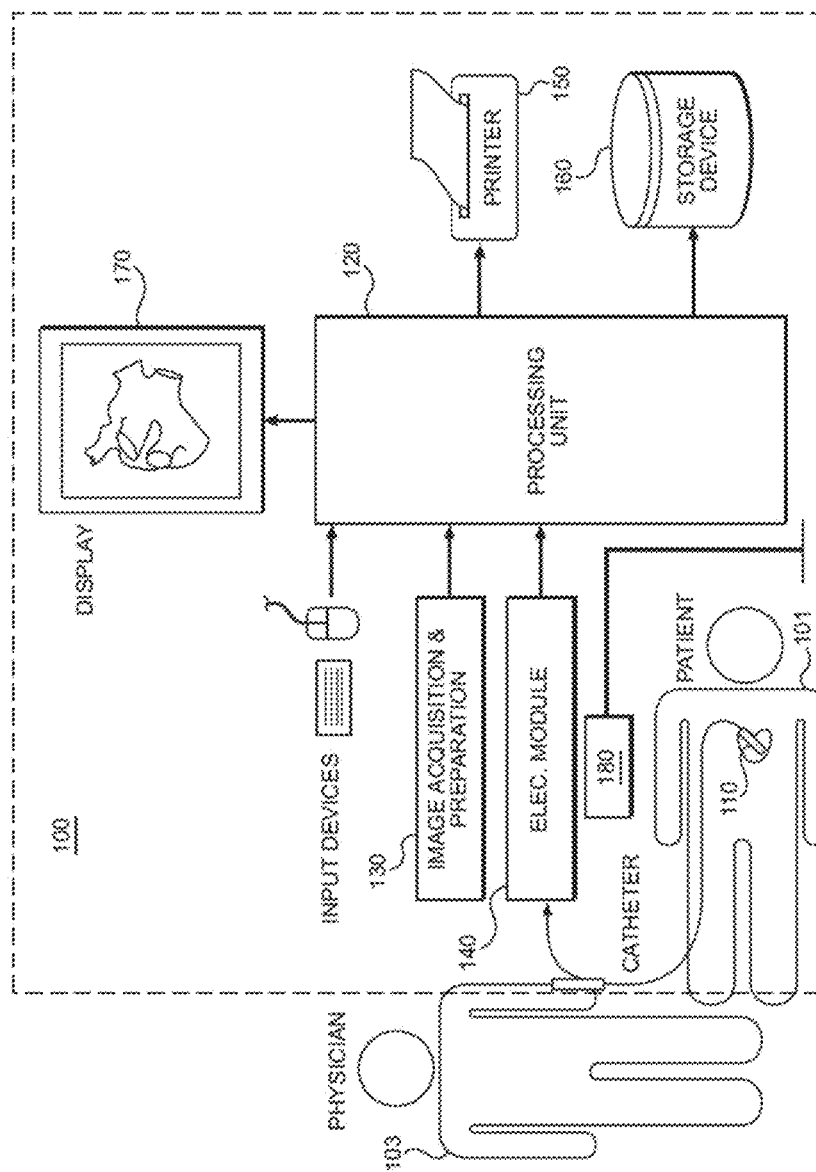
FIG. 1 is a conceptual schematic diagram depicting an illustrative electrophysiology system, in accordance with some embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although illustrative methods may be represented by one or more drawings (e.g., flow diagrams, communication flows, etc.), the drawings should not be interpreted as implying any requirement of, or particular order among or between, various steps disclosed herein. However, certain some embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

During atrial fibrillation (AF), traditional activation mapping using a reference electrode on a coronary sinus (CS) catheter is likely not possible due to the disorganized and dissociated nature of activation on the CS. This limits the utility of the cardiac mapping system during many AF cases, most notably persistent AF. It has demonstrated the presence of clear and consistent organization with discrete cycle length patterns in some areas of the atria during AF. Knowledge on how local cycle length and duty cycle data patterns cluster spatially is important in finding AF drivers. In some cases, for a given cycle length, duty cycle gives important information as to the nature of the different patterns observed, for example, the type of AF driver responsible for each cycle length observed, and how that driver might best identified/eliminated. Embodiments of systems and methods described herein facilitate determining characteristics (e.g., local cycle length, local duty cycle, confidence values, and the like), also referred to as waveform characteristics, of cardiac electrical signals recorded on a mapping catheter without a fixed or associated reference electrode or without referencing the signals measured by a fixed or associated reference electrode. Determination of local cycle length according to the present disclosure provides the clinician with a diagnostic estimation of actual atrial fibrillation cycle length, which can be difficult to ascertain using conventional methods. In embodiments, the local cycle length can be determined without the need for a fixed or associated reference cycle, and/or without referencing the signals measured by a fixed or associated reference electrode. Local duty cycle of cardiac electrical signals can be determined based on the local cycle length. In embodiments, the local duty cycle can determined without the need for a fixed or associated reference cycle length, and/or without referencing the signals measured by a fixed or associated reference electrode.

Embodiments of the present disclosure facilitate finding meaningful deflections while rejecting noises and artifacts. An activation waveform, or referred to as an annotation waveform, is a set of activation waveform values and may include, for example, a set of discrete activation waveform values (e.g., a set of activation waveform values, a set of activation time annotations, etc.), a function defining an activation waveform curve, and/or the like. In some embodiments, each data point of an activation waveform represents the per-sample "probability" of tissue activation. In some embodiments, the waveform characteristics may be displayed, used to present in an activation propagation map, used to facilitate diagnoses, used to facilitate classification of electrical signals, and/or the like. To perform aspects of embodiments of the methods described herein, the cardiac electrical signals may be obtained from a mapping catheter (e.g., associated with a mapping system), which may be used in conjunction with other equipment typically used in an electrophysiology lab, e.g., a recording system, a coronary sinus (CS) catheter or other reference catheter, an ablation catheter, a memory device (e.g., a local memory, a cloud server, etc.), a communication component, a medical device (e.g., an implantable medical device, an external medical device, a telemetry device, etc.), and/or the like.

As the term is used herein, a sensed cardiac electrical signal may refer to one or more sensed signals. Each cardiac electrical signal may comprise intracardiac electrograms (EGMs) sensed within a patient's heart and may include any number of features that may be ascertained by aspects of an electrophysiology system. Examples of cardiac electrical signal features include, but are not limited to, activation times, activations, activation waveforms, filtered activation waveforms, minimum voltage values, maximum voltages values, maximum negative time-derivatives of voltages, instantaneous potentials, voltage amplitudes, dominant frequencies, peak-to-peak voltages, and/or the like. A cardiac electrical signal feature may refer to one or more features extracted from one or more cardiac electrical signals, derived from one or more features that are extracted from one or more cardiac electrical signals, and/or the like. Additionally, a representation, on a cardiac and/or a surface map, of a cardiac electrical signal feature may represent one or more cardiac electrical signal features, an interpolation of a number of cardiac electrical signal features, and/or the like.

Each cardiac signal also may be associated with a set of respective position coordinates that corresponds to the location at which the cardiac electrical signal was sensed. Each of the respective position coordinates for the sensed cardiac signals may include three-dimensional Cartesian coordinates, polar coordinates, and/or the like. In some cases, other coordinate systems can be used. In some embodiments, an arbitrary origin is used and the respective position coordinates refer to positions in space relative to the arbitrary origin. Since, in some embodiments, the cardiac signals may be sensed on the cardiac surfaces, the respective position coordinates may be on the endocardial surface, epicardial surface, in the mid-myocardium of the patient's heart, and/or in the vicinity of one of one of these.

FIG. 1 shows a schematic diagram of an exemplary embodiment of an electrophysiology system 100. As indicated above, embodiments of the subject matter disclosed herein may be implemented in an electrophysiology system (e.g., a mappings system, a cardiac mapping system), while other embodiments may be implemented in an ablation system, a recording system, a computer analysis system, and/or the like. The electrophysiology system 100 includes a moveable catheter 110 having multiple spatially distributed electrodes. During a signal-acquisition stage, the catheter 110 is displaced to multiple locations within the heart chamber into which the catheter 110 is inserted. In some embodiments the distal end of the catheter 110 is fitted with multiple electrodes spread somewhat uniformly over the catheter. For example, the electrodes may be mounted on the catheter 110 following a 3D olive shape, a basket shape, and/or the like. The electrodes are mounted on a device capable of deploying the electrodes into the desired shape while inside the heart, and retracting the electrodes when the catheter is removed from the heart. To allow deployment into a 3D shape in the heart, electrodes may be mounted on a balloon, shape memory material such as Nitinol, actuable hinged structure, and/or the like. According to embodiments, the catheter 110 may be a mapping catheter, an ablation catheter, a diagnostic catheter, a CS catheter, and/or the like. For example, aspects of embodiments of the catheter 110, the electrical signals obtained using the catheter 110, and subsequent processing of the electrical signals, as described herein, may also be applicable in implementations having a recording system, ablation system, and/or any other system having a catheter with electrodes that may be configured to obtain cardiac electrical signals.

At each of the locations to which the catheter 110 is moved, the catheter's multiple electrodes acquire signals resulting from the electrical activity in the heart. Consequently, reconstructing and presenting to a user (such as a doctor and/or technician) physiological data pertaining to the heart's electrical activity may be based on information acquired at multiple locations, thereby providing a more accurate and faithful reconstruction of physiological behavior of the endocardium surface. The acquisition of signals at multiple catheter locations in the heart chamber enables the catheter to effectively act as a "mega-catheter" whose effective number of electrodes and electrode span is proportional to the product of the number of locations in which signal acquisition is performed and the number of electrodes the catheter has.

To enhance the quality of the reconstructed physiological information at the endocardium surface, in some embodiments the catheter 110 is moved to more than three locations (for example, more than 5, 10, or even 50 locations) within the heart chamber. Further, the spatial range over which the catheter is moved may be larger than one third (⅓) of the diameter of the heart cavity (for example, larger than 35%, 40%, 50% or even 60% of the diameter of the heart cavity). Additionally, in some embodiments the reconstructed physiological information is computed based on signals measured over several heart beats, either at a single catheter location within the heart chamber or over several locations. In circumstances where the reconstructed physiological information is based on multiple measurements over several heart beats, the measurements may be synchronized with one another so that the measurement are performed at approximately the same phase of the heart cycle. The signal measurements over multiple beats may be synchronized based on features detected from physiological data such as surface electrocardiograms (ECGs) and/or intracardiac electrograms (EGMs).

The electrophysiology system 100 further includes a processing unit 120 which performs several of the operations pertaining to the mapping procedure, including the reconstruction procedure to determine the physiological information at the endocardium surface (e.g., as described above) and/or within a heart chamber. The processing unit 120 also may perform a catheter registration procedure. The processing unit 120 also may generate a 3D grid used to aggregate the information captured by the catheter 110 and to facilitate display of portions of that information.

The location of the catheter 110 inserted into the heart chamber can be determined using a conventional sensing and tracking system 180 that provides the 3D spatial coordinates of the catheter and/or its multiple electrodes with respect to the catheter's coordinate system as established by the sensing and tracking system. These 3D spatial locations may be used in building the 3D grid. Embodiments of the system 100 may use a hybrid location technology that combines impedance location with magnetic location technology. This combination may enable the system 100 to accurately track catheters that are connected to the system 100. Magnetic location technology uses magnetic fields generated by a localization generator positioned under the patient table to track catheters with magnetic sensors. Impedance location technology may be used to track catheters that may not be equipped with a magnetic location sensor, which may be used with surface ECG patches.

In some embodiments, to perform a mapping procedure and reconstruct physiological information on the endocardium surface, the processing unit 120 may align the coordinate system of the catheter 110 with the endocardium surface's coordinate system. The processing unit 120 (or some other processing component of the system 100) may determine a coordinate system transformation function that transforms the 3D spatial coordinates of the catheter's locations into coordinates expressed in terms of the endocardium surface's coordinate system, and/or vice-versa. In some cases, such a transformation may not be necessary, as some embodiments of the 3D grid may be used to capture contact and non-contact EGMs, and select mapping values based on statistical distributions associated with nodes of the 3D grid. The processing unit 120 also may perform post-processing operations on the physiological information to extract and display useful features of the information to the operator of the system 100 and/or other persons (e.g., a physician).

According to embodiments, the signals acquired by the multiple electrodes of catheter 110 are passed to the processing unit 120 via an electrical module 140, which may include, for example, a signal conditioning component. The electrical module 140 receives the signals communicated from the catheter 110 and performs signal enhancement operations on the signals before they are forwarded to the processing unit 120. The electrical module 140 may include signal conditioning hardware, software, and/or firmware that may be used to amplify, filter and/or sample intracardiac potential measured by one or more electrodes. The intracardiac signals typically have a maximum amplitude of 60 mV, with a mean of a few millivolts.

In some embodiments, the signals are filtered by a band-pass filter with a frequency range (e.g., 0.5-500 Hz) and sampled with analog to digital converters (e.g., with 15-bit resolution at 1 kHz). To avoid interference with electrical equipment in the room, the signals may be filtered to remove the frequency corresponding to the power supply (e.g., 60 Hz). Other types of signal processing operations such as spectral equalization, automatic gain control, etc. may also take place. In some implementations, the intracardiac signals may be unipolar signals measured relative to a reference (which may be a virtual reference). In such implementations, the reference can be, for example, a coronary sinus catheter or Wilson's Central Terminal (WCT), from which the signal processing operations may compute differences to generate multipolar signals (e.g., bipolar signals, tripolar signals, etc.). In some other implementations, the signals may be processed (e.g., filtered, sampled, etc.) before and/or after generating the multipolar signals. The resultant processed signals are forwarded by the electrical module 140 to the processing unit 120 for further processing.

As further shown in FIG. 1, the electrophysiology system 100 also may include peripheral devices such as a printer 150 and/or display device 170, both of which may be interconnected to the processing unit 120. Additionally, the electrophysiology system 100 includes storage device 160 that may be used to store data acquired by the various interconnected modules, including the volumetric images, raw data measured by electrodes and/or the resultant endocardium representation computed therefrom, the partially computed transformations used to expedite the mapping procedures, the reconstructed physiological information corresponding to the endocardium surface, and/or the like.

In some embodiments, the processing unit 120 may be configured to automatically improve the accuracy of its algorithms by using one or more artificial intelligence techniques (e.g., machine learning models, deep learning models), classifiers, and/or the like. In some embodiments, for example, the processing unit may use one or more supervised and/or unsupervised techniques such as, for example, support vector machines (SVMs), k-nearest neighbor techniques, neural networks, convolutional neural networks, recurrent neural networks, and/or the like. In some embodiments, classifiers may be trained and/or adapted using feedback information from a user, other metrics, and/or the like.

The illustrative electrophysiology system 100 shown in FIG. 1 is not intended to suggest any limitation as to the scope of use or functionality of embodiments of the present disclosure. Neither should the illustrative electrophysiology system 100 be interpreted as having any dependency or requirement related to any single component or combination of components illustrated therein. Additionally, various components depicted in FIG. 1 may be, in some embodiments, integrated with various ones of the other components depicted therein (and/or components not illustrated), all of which are considered to be within the ambit of the subject matter disclosed herein. For example, the electrical module 140 may be integrated with the processing unit 120. Additionally, or alternatively, aspects of embodiments of the electrophysiology system 100 may be implemented in a computer analysis system configured to receive cardiac electrical signals and/or other information from a memory device (e.g., a cloud server, a mapping system memory, etc.), and perform aspects of embodiments of the methods described herein for processing cardiac information (e.g., determining annotation waveforms, etc.). That is, for example, a computer analysis system may include a processing unit 120, but not a mapping catheter.

Figure 2:
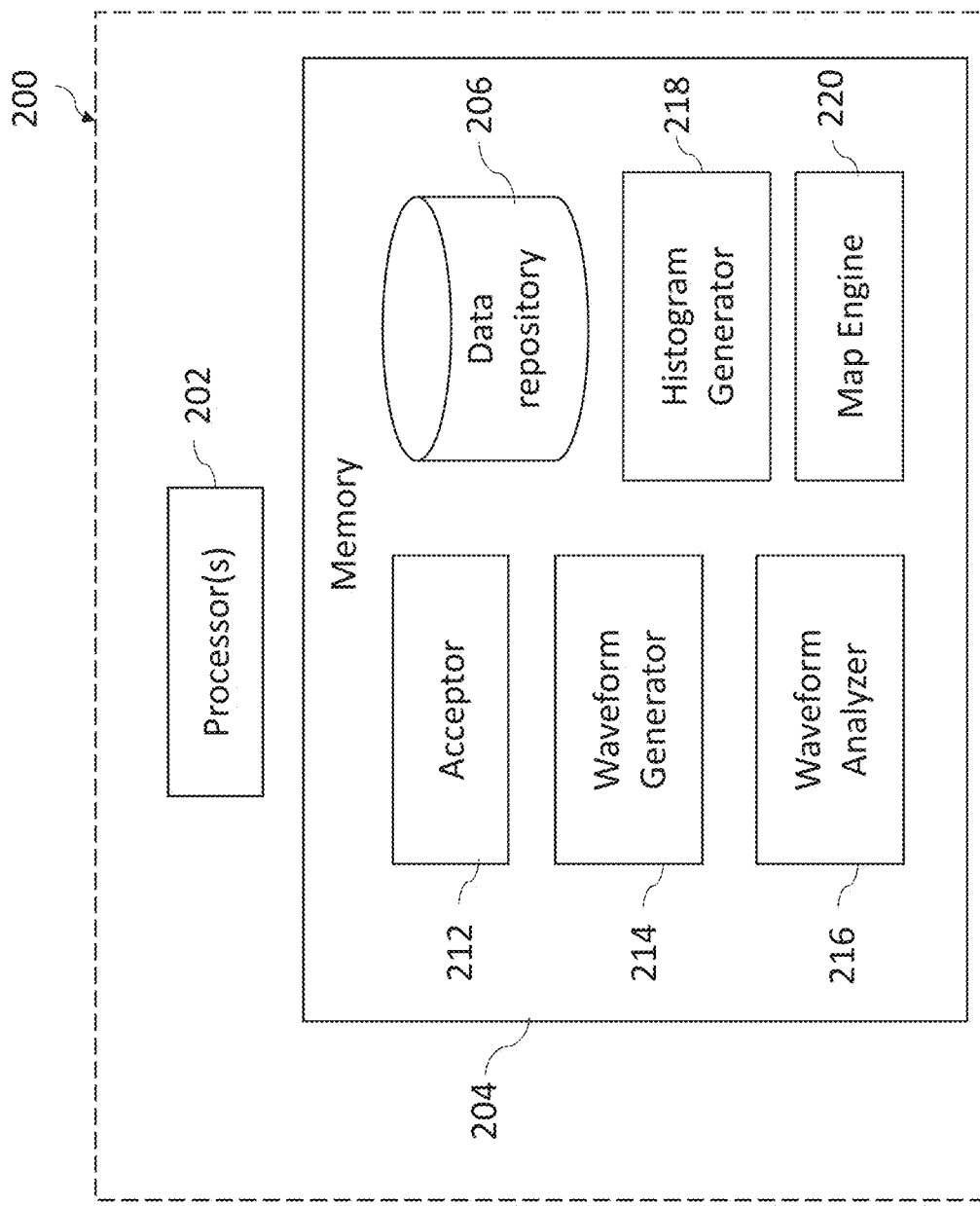
FIG. 2 is a block diagram depicting an illustrative processing unit for use with an electrophysiology system, in accordance with embodiments of the subject matter disclosed herein.

FIG. 2 is a block diagram of an illustrative processing unit 200, in accordance with embodiments of the present disclosure. The processing unit 200 may be, be similar to, include, or be included in the processing unit 120 depicted in FIG. 1. As shown in FIG. 2, the processing unit 200 may be implemented on a computing device that includes one or more processors 202 and one or more memories 204. Although the processing unit 200 is referred to herein in the singular, the processing unit 200 may be implemented in multiple instances (e.g., as a server cluster), distributed across multiple computing devices, instantiated within multiple virtual machines, and/or the like. One or more components for facilitating cardiac mapping may be stored in the memory 204. In some embodiments, the processor 202 may be configured to instantiate the one or more components to generate an activation waveform, a set of waveform analysis results, electrogram characteristics, a histogram, and a cardiac map, any one or more of which may be stored in the data repository 206.

As depicted in FIG. 2, the processing unit 200 may include an acceptor 212 configured to receive electrical signals from a mapping catheter (e.g., the catheter 110 depicted in FIG. 1). The measured electrical signals may include a number of intracardiac electrograms (EGMs) sensed within a patient's heart. The acceptor 212 may also receive an indication of a measurement location corresponding to each of the electrical signals. In some embodiments, the acceptor 212 may be configured to determine whether to accept the electrical signals that have been received. The acceptor 212 may utilize any number of different components and/or techniques to determine which electrical signals or beats to accept, such as filtering, beat matching, morphology analysis, positional information (e.g., catheter motion), respiration gating, and/or the like. The received electrical signals and/or the processed electrical signals may be stored in the data repository 206.

The accepted electrical signals are received by an activation waveform generator 214 that is configured to extract at least one annotation feature from each of the electrical signals, in cases in which the electrical signal includes an annotation feature to extract. In some embodiments, the at least one annotation feature includes at least one value corresponding to at least one annotation metric. The at least one feature may include at least one event, where the at least one event includes the at least one value corresponding to the at least one metric and/or at least one corresponding time (a corresponding time does not necessarily exist for each annotation feature). In some embodiments, the at least one metric may include, for example, an activation time, minimum voltage value, maximum voltage value, maximum negative time-derivative of voltage, an instantaneous potential, a voltage amplitude, a dominant frequency, a peak-to-peak voltage, an activation duration, and/or the like. In some embodiments, the activation waveform generator 214 may be configured to detect activations and to generate an activation waveform. In some cases, the waveform generator 214 can use any one of activation waveform embodiments, for example, including those described in U.S. Patent Publication 2018/0296113, entitled "ANNOTATION WAVEFORM," the disclosure of which is hereby expressly incorporated herein by reference.

As illustrated in FIG. 2, the processing unit 200 includes a waveform analyzer 216 to analyze the activation waveform generated by the activation waveform generator 214 and the received cardiac electrical signals. The waveform analyzer 216 is configured determine one or more characteristics of the cardiac electrical signals, or referred to as electrogram characteristics, for example, the cycle length, the local cycle length, the duty cycle, the local duty cycle, and confidence values associated thereof.

As shown in FIG. 2, the processing unit 200 includes a histogram generator 218 that is configured to generate an analysis histogram having a number of bins within which analysis results (e.g., local cycle lengths, local duty cycles) from the waveform analyzer 216 are included. The processing unit 200, using the histogram generator 218, may be configured to aggregate a set of analysis results by including each of the analysis results in a histogram. For example, the histogram generator 218 may be configured to aggregate a set of local cycle length, local duty cycles, and confidence levels in a histogram. Additionally, the processing unit 200 includes a map engine 220 that is configured to facilitate presentation of a map corresponding to a cardiac surface based on the electrical signals. In some embodiments, the map may include a voltage map, an activation map, a fractionation map, velocity map, confidence map, and/or the like. In some embodiments, the map may include overlaid representations of analysis result(s) (e.g., local cycle length, local duty cycle, etc.) at a corresponding location in the heart chamber.

The illustrative processing unit 200 shown in FIG. 2 is not intended to suggest any limitation as to the scope of use or functionality of embodiments of the present disclosure. Neither should the illustrative processing unit 200 be interpreted as having any dependency or requirement related to any single component or combination of components illustrated therein. Additionally, any one or more of the components depicted in FIG. 2 may be, in some embodiments, integrated with various ones of the other components depicted therein (and/or components not illustrated), all of which are considered to be within the ambit of the subject matter disclosed herein. For example, the acceptor 212 may be integrated with the histogram generator 218 and/or the mapping engine 220. In some embodiments, the processing unit 200 may not include an acceptor 212, while in other embodiments, the acceptor 212 may be configured to receive electrical signals from a memory device, a communication component, and/or the like.

Additionally, the processing unit 200 may (alone and/or in combination with other components of the system 100 depicted in FIG. 1, and/or other components not illustrated) perform any number of different functions and/or processes associated with cardiac mapping (e.g., triggering, blanking, field mapping, etc.) such as, for example, those described in U.S. Patent Publication 2018/0296113, entitled "ANNOTATION WAVEFORM;" U.S. Pat. No. 8,428,700, entitled "ELECTROANATOMICAL MAPPING;" U.S. Pat. No. 8,948,837, entitled "ELECTROANATOMICAL MAPPING;" U.S. Pat. No. 8,615,287, entitled "CATHETER TRACKING AND ENDOCARDIUM REPRESENTATION GENERATION;" U.S. Patent Publication 2015/0065836, entitled "ESTIMATING THE PREVALENCE OF ACTIVATION PATTERNS IN DATA SEGMENTS DURING ELECTROPHYSIOLOGY MAPPING;" U.S. Pat. 6,070,094, entitled "SYSTEMS AND METHODS FOR GUIDING MOVABLE ELECTRODE ELEMENTS WITHIN MULTIPLE-ELECTRODE STRUCTURE;" U.S. Pat. No. 6,233,491, entitled "CARDIAC MAPPING AND ABLATION SYSTEMS;" U.S. Pat. No. 6,735,465, entitled "SYSTEMS AND PROCESSES FOR REFINING A REGISTERED MAP OF A BODY CAVITY;" the disclosures of which are hereby expressly incorporated herein by reference.

According to embodiments, various components of the electrophysiology system 100, illustrated in FIG. 1, and/or the processing unit 200, illustrated in FIG. 2, may be implemented on one or more computing devices. A computing device may include any type of computing device suitable for implementing embodiments of the disclosure. Examples of computing devices include specialized computing devices or general-purpose computing devices such "workstations," "servers," "laptops," "desktops," "tablet computers," "hand-held devices," "general-purpose graphics processing units (GPGPUs)," and the like, all of which are contemplated within the scope of FIGS. 1 and 2 with reference to various components of the system 100 and/or processing unit 200.

In some embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in some embodiments, the computing device may include a number of processors, a number of memory components, a number of I/O ports, a number of I/O components, and/or a number of power supplies. Additionally, any number of these components, or combinations thereof, may be distributed and/or duplicated across a number of computing devices.

In some embodiments, memory (e.g., the storage device 160 depicted in FIG. 1, the memory 204 and/or the data repository 206 depicted in FIG. 2) includes computer-readable media in the form of volatile and/or nonvolatile memory, transitory and/or non-transitory storage media and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In some embodiments, the memory 204 and/or the storage device 160 stores computer-executable instructions for causing a processor (e.g., the processing unit 120 depicted in FIG. 1 and/or the processor 202 depicted in FIG. 2) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Examples of such program components include the acceptor 212, the waveform generator 214, the waveform analyzer 216, the histogram generator 218, and the mapping engine 220. Program components may be programmed using any number of different programming environments, including various languages, development kits, frameworks, and/or the like. Some or all of the functionality contemplated herein may also, or alternatively, be implemented in hardware and/or firmware.

The data repository 206 may be implemented using any one of the configurations described below. A data repository may include random access memories, flat files, XML files, and/or one or more database management systems (DBMS) executing on one or more database servers or a data center. A database management system may be a relational (RDBMS), hierarchical (HDBMS), multidimensional (MDBMS), object oriented (ODBMS or OODBMS) or object relational (ORDBMS) database management system, and the like. The data repository may be, for example, a single relational database. In some cases, the data repository may include a plurality of databases that can exchange and aggregate data by data integration process or software application. In an exemplary embodiment, at least part of the data repository 206 may be hosted in a cloud data center. In some cases, a data repository may be hosted on a single computer, a server, a storage device, a cloud server, or the like. In some other cases, a data repository may be hosted on a series of networked computers, servers, or devices. In some cases, a data repository may be hosted on tiers of data storage devices including local, regional, and central.

Figure 3:
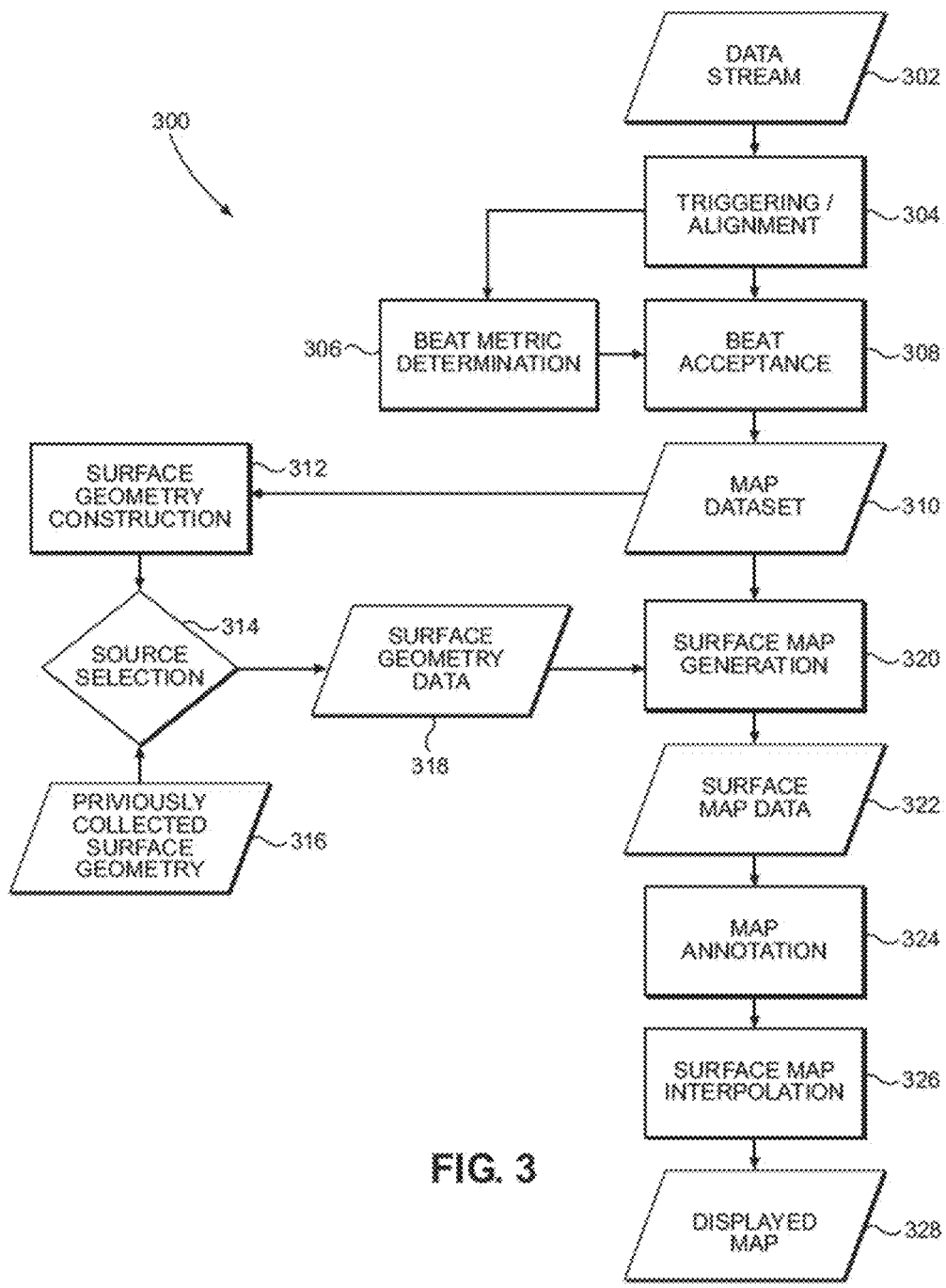
FIG. 3 is a flow diagram depicting an illustrative process for generating a cardiac map, in accordance with embodiments of the subject matter disclosed herein.

FIG. 3 is a flow diagram of an illustrative process/method 300 for automated electro-anatomical mapping, in accordance with embodiments of the present disclosure. Aspects of embodiments of the method 300 may be performed, for example, by a processing unit (e.g., the processing unit 120 depicted in FIG. 1, and/or the processing unit 200 depicted in FIG. 2). A data stream 302 containing multiple signals is first input into the system (e.g., the cardiac electrophysiology system 100 depicted in FIG. 1). During the automated electro-anatomical mapping process, the data stream 302 provides a collection of physiological and non-physiological signals that serve as inputs to the mapping process. The signals may be collected directly by the mapping system, and/or obtained from another system using an analog or digital interface. The data stream 302 may include signals such as unipolar and/or bipolar intracardiac electrograms (EGMs), surface electrocardiograms (ECGs), electrode location information originating from one or more of a variety of methodologies (magnetic, impedance, ultrasound, real time MRI, etc.), tissue proximity information, catheter force and/or contact information obtained from one or more of a variety of methodologies (force spring sensing, piezo-electric sensing, optical sensing etc.), catheter tip and/or tissue temperature, acoustic information, catheter electrical coupling information, catheter deployment shape information, electrode properties, respiration phase, blood pressure, other physiological information, and/or the like.

For the generation of specific types of maps, one or more signals may be used as one or more references, during a triggering/alignment process 304, to trigger and align the data stream 302 relative to the cardiac, other biological cycle and/or an asynchronous system clock resulting in beat datasets. Additionally, for each incoming beat dataset, a number of beat metrics are computed during a beat metric determination process 306. Beat metrics may be computed using information from a single signal, spanning multiple signals within the same beat and/or from signals spanning multiple beats. The beat metrics provide multiple types of information on the quality of the specific beat dataset and/or likelihood that the beat data is good for inclusion in the map dataset. A beat acceptance process 308 aggregates the criteria and determines which beat datasets will make up the map dataset 310. The map dataset 310 may be stored in association with a 3D grid that is dynamically generated during data acquisition.

Surface geometry data 318 may be generated concurrently during the same data acquisition process using identical and/or different triggering and/or beat acceptance metrics employing a surface geometry construction process 312. This process constructs surface geometry using data such as electrode locations and catheter shape contained in the data stream. Additionally, or alternatively, previously or concurrently collected surface geometry 316 may be used as an input to surface geometry data 318. Such geometry may have been collected previously in the same procedure using a different map dataset, and/or using a different modality such as CT, MRI, ultrasound, rotational angiography, and/or the like, and registered to the catheter locating system. The system performs a source selection process 314, in which it selects the source of the surface geometry data and provides surface geometry data 318 to a surface map generation process 320. The surface map generation process 320 is employed to generate surface map data 322 from the map dataset 310 and surface geometry data 318.

The surface geometry construction algorithm generates the anatomical surface on which the electroanatomical map is displayed. Surface geometry can be constructed, for example, using aspects of a system as described U.S. Pat. No. 8,103,338, entitled "Impedance Based Anatomy Generation"; and/or U.S. Pat. No. 8,948,837, entitled "Electro-anatomical Mapping", the contents of each of which is incorporated by reference herein in its entirety. Additionally, or alternatively, an anatomical shell can be constructed by the processing unit by fitting a surface on electrode locations that are determined either by the user or automatically to be on the surface of the chamber. In addition, a surface can be fit on the outermost electrode and/or catheter locations within the chamber.

As described, the map dataset 310 from which the surface is constructed can employ identical or different beat acceptance criteria from those used for electrical and other types of maps. The map dataset 310 for surface geometry construction can be collected concurrently with electrical data or separately. Surface geometry can be represented as a mesh containing a collection of vertices (points) and the connectivity between them (e.g. triangles). Alternatively, surface geometry can be represented by different functions such as higher order meshes, non-uniform rational basis splines (NURBS), and/or curvilinear shapes.

The generation process 320 generates surface map data 322. The surface map data 322 may provide information on cardiac electrical excitation, cardiac motion, tissue proximity information, tissue impedance information, force information, and/or any other collected information desirable to the clinician. The combination of map dataset 310 and surface geometry data 318 allows for surface map generation. The surface map is a collection of values or waveforms (e.g., EGMs) on the surface of the chamber of interest, whereas the map dataset can contain data that is not on the cardiac surface. One approach for processing the map dataset 310 and surface geometry data 318 to obtain a surface map dataset 322 is described in U.S. Pat. No. 7,515,954, entitled "NON-CONTACT CARDIAC MAPPING, INCLUDING MOVING CATHETER AND MULTI-BEAT INTEGRATION" and filed Jun. 13, 2006, the contents of which is incorporated by reference herein in its entirety.

Alternatively, or in combination with the method above, an algorithm that applies acceptance criteria to individual electrodes can be employed. For example, electrode locations exceeding a set distance (e.g., 3 mm) from surface geometry can be rejected. Another algorithm can incorporate tissue proximity information using impedance for inclusion in the surface map data. In this case only electrode location whose proximity value is less than 3 mm might be included. Additional metrics of the underlying data can also be used for this purpose. For example, EGM properties similar to beat metrics can be assessed on a per electrode basis. In this case metrics such as far field overlap and/or EGM consistency can be used. It should be understood that variations on the method to project points from the map dataset 310 to the surface and/or to select appropriate points can exist.

Once obtained, the surface map data 322 may be further processed to annotate desired features from the underlying data, a process defined as surface map annotation 324. Once data is collected into surface map data 322, attributes relating to the collected data may be automatically presented to the user. These attributes can be automatically determined and applied to the data by the computer system and are referred to herein as annotations. Exemplary annotations include activation time, the presence of double activation or fractionation, voltage amplitude, spectral content, and/or the like. Due to the abundance of data available in automated mapping (e.g., mapping completed by the computer system with minimal human input related to the incoming data), it is not practical for the operator to review and annotate data manually. However, human input can be a valuable addition to the data, and so when user input is provided it is necessary for the computer system to automatically propagate and apply it to more than one data point at a time.

It may be possible to use the computer system to automatically annotate activation time, voltage, and other characteristics of individual EGMs. Activation time detection may use methods similar to those previously described to detect a trigger and can similarly benefit from the use of blanking and powered triggering operator. Desired annotations may include instantaneous potential, activation time, voltage amplitude, dominant frequency and/or other properties of the signal. Once computed, the annotations may be displayed superimposed on chamber geometry. In some embodiments, a gap-filling surface map interpolation may be employed 326. For example, in some embodiments, a gap-filling interpolation may be employed where a distance between a point on the surface to a measured EGM exceeds a threshold, as this may indicate, for example, that grid-based interpolation, as described herein, may not be as effective in that situation. Displayed maps 328 can be computed and displayed separately, and/or overlaid on top of each other.

The illustrative process 300 shown in FIG. 3 is not intended to suggest any limitation as to the scope of use or functionality of embodiments of the present disclosure. Neither should the illustrative process 300 be interpreted as having any dependency or requirement related to any single component or combination of components illustrated therein. Additionally, any one or more of the components depicted in FIG. 3 may be, for example, integrated with various ones of the other components depicted therein (and/or components not illustrated), all of which are considered to be within the ambit of the present disclosure.

Figure 4A:
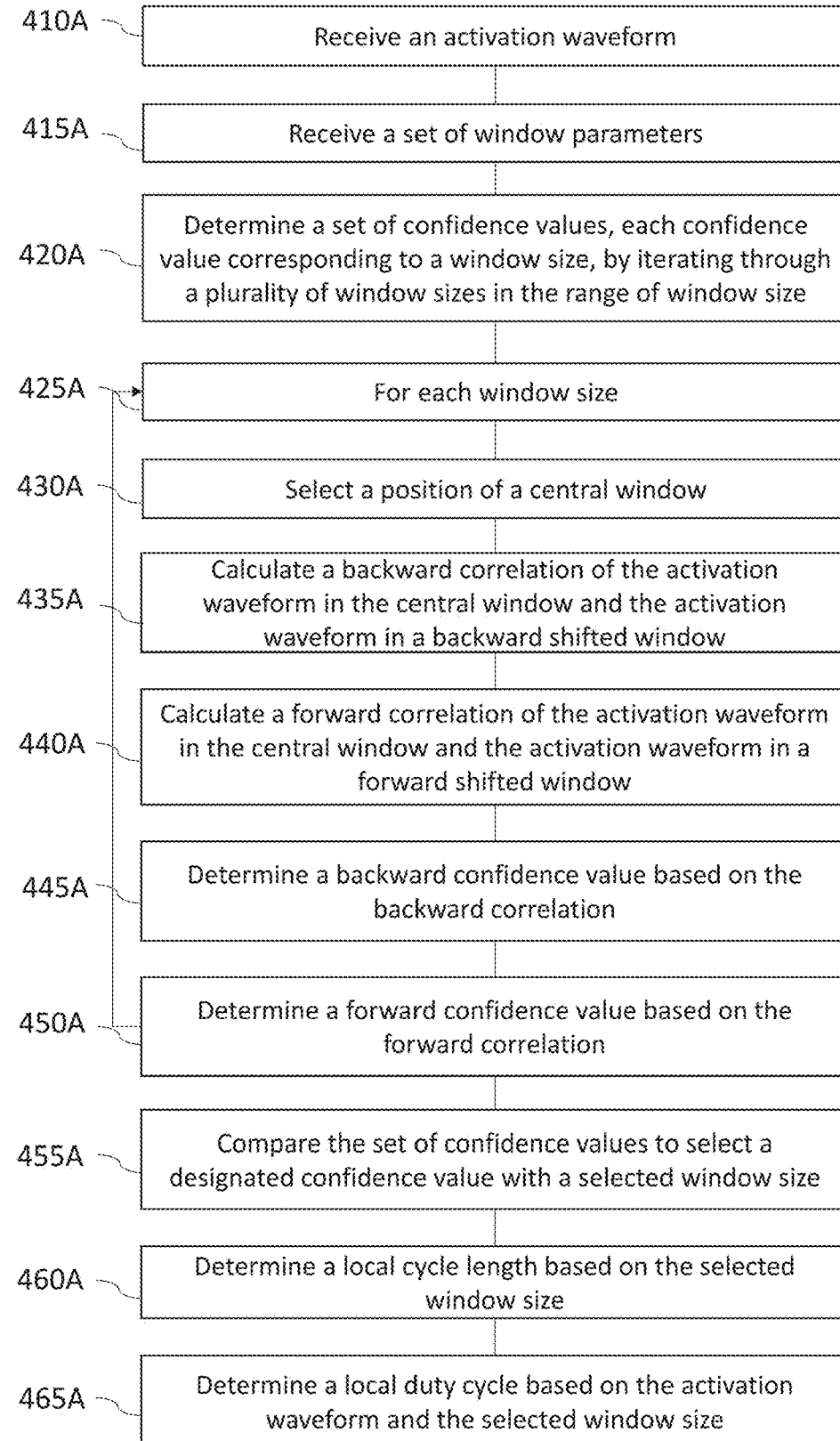
FIGS. 4A-4D are flow diagrams depicting illustrative methods of processing electrophysiological information, in accordance with embodiments of the subject matter disclosed herein.

FIG. 4A is an example flow diagram depicting an illustrative method 400A of processing cardiac electrical signals and generated activation waveform, in accordance with some embodiments of the present disclosure. Aspects of embodiments of the method 400A may be performed, for example, by an electrophysiology system or a processing unit (e.g., the processing unit 120 depicted in FIG. 1, and/or the processing unit 200 depicted in FIG. 2). One or more steps of method 400A are optional and/or can be modified by one or more steps of other embodiments described herein. Additionally, one or more steps of other embodiments described herein may be added to the method 400A. First, the electrophysiology system receives an activation waveform (410A). The activation waveform includes a set of activation waveform data. In some embodiments, the activation waveform is associated with a section of cardiac signals, for example, a signal section associated with a heartbeat, a predetermined sample window, a predetermine time duration, or the like.

The activation waveform can be generated using electrical signals collected from a catheter. A catheter may be any catheter having one or more electrodes configured to obtain electrical signals (e.g., the catheter 110 depicted in FIG. 1, an ablation catheter, etc.). According to embodiments, cardiac electric signal features may be extracted from the cardiac electrical signals (e.g., EGMs). Examples of features of the cardiac electrical signals include, but are not limited to, activation times, minimum voltage values, maximum voltages values, maximum negative time-derivatives of voltages, instantaneous potentials, voltage amplitudes, dominant frequencies, peak-to-peak voltages, and/or the like. Each of the respective points at which a cardiac electrical signal is sensed may have a corresponding set of three-dimensional position coordinates. For example, the position coordinates of the points may be represented in Cartesian coordinates. Other coordinate systems can be used, as well. In some embodiments, an arbitrary origin is used and the respective position coordinates are defined with respect to the arbitrary origin. In some embodiments, the points have non-uniform spacing, while in other embodiments, the points have uniform spacing. In some embodiments, the point corresponding to each sensed cardiac electrical signal may be located on the endocardial surface of the heart and/or below the endocardial surface of the heart.

In some embodiments, identifying deflections that deviate beyond the signal baseline may include determining, for each sample point of an electrical signal, a corresponding activation waveform value. For example, in embodiments, the system may include determining a probability (e.g., a value between 0 and 1, inclusive) that a given sample point represents an activation, based on its relation to the signal baseline. In embodiments, other numerical scales may be used for assigning the probability such as, for example, values between 0 and 100, and/or the like. In embodiments, a likelihood (e.g., a probability) that a signal deflection represents an activation may be determined based on the deviation of that deflection from the signal baseline. For example, a deflection having a maximum amplitude that deviates from the signal baseline by at least a specified amount may be assigned a probability of 1, while a deflection having a maximum amplitude that deviates from the signal baseline by at most a specified amount may be assigned a probability of 0. Probabilities may be assigned, in linear and/or nonlinear, fashions to deflections having amplitudes that are not satisfied by either of the preceding criteria based on, for example, the relative deviation of the deflection amplitude with respect to the above criteria. In this manner, for example, an activation waveform value may be a probability that an identified deflection corresponding to a sample point represents an activation.

Figure 5A:
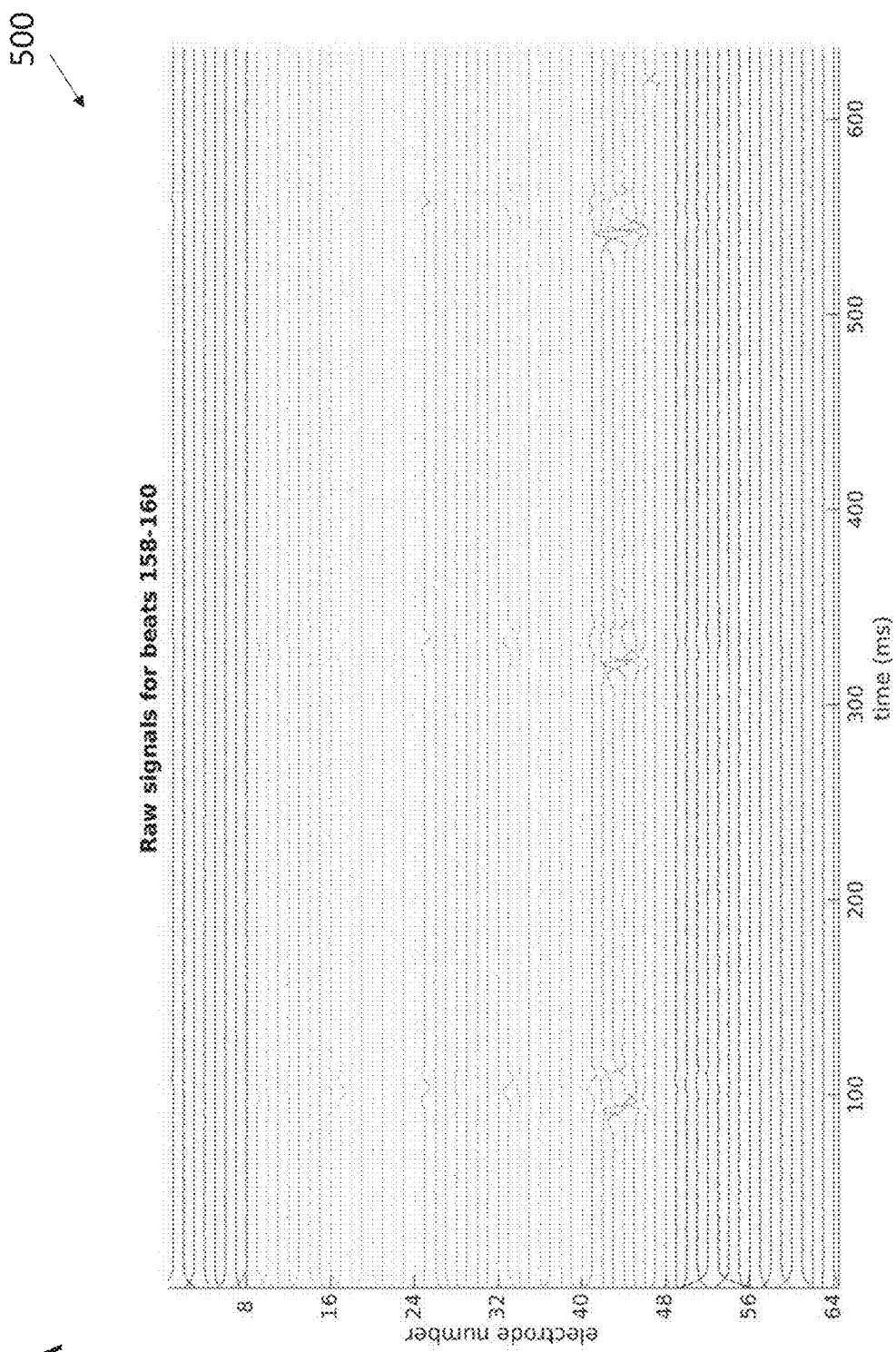
FIG. 5A depicts an exemplary graphical representation illustrating electrical signals received from a mapping catheter.
Figure 5B:
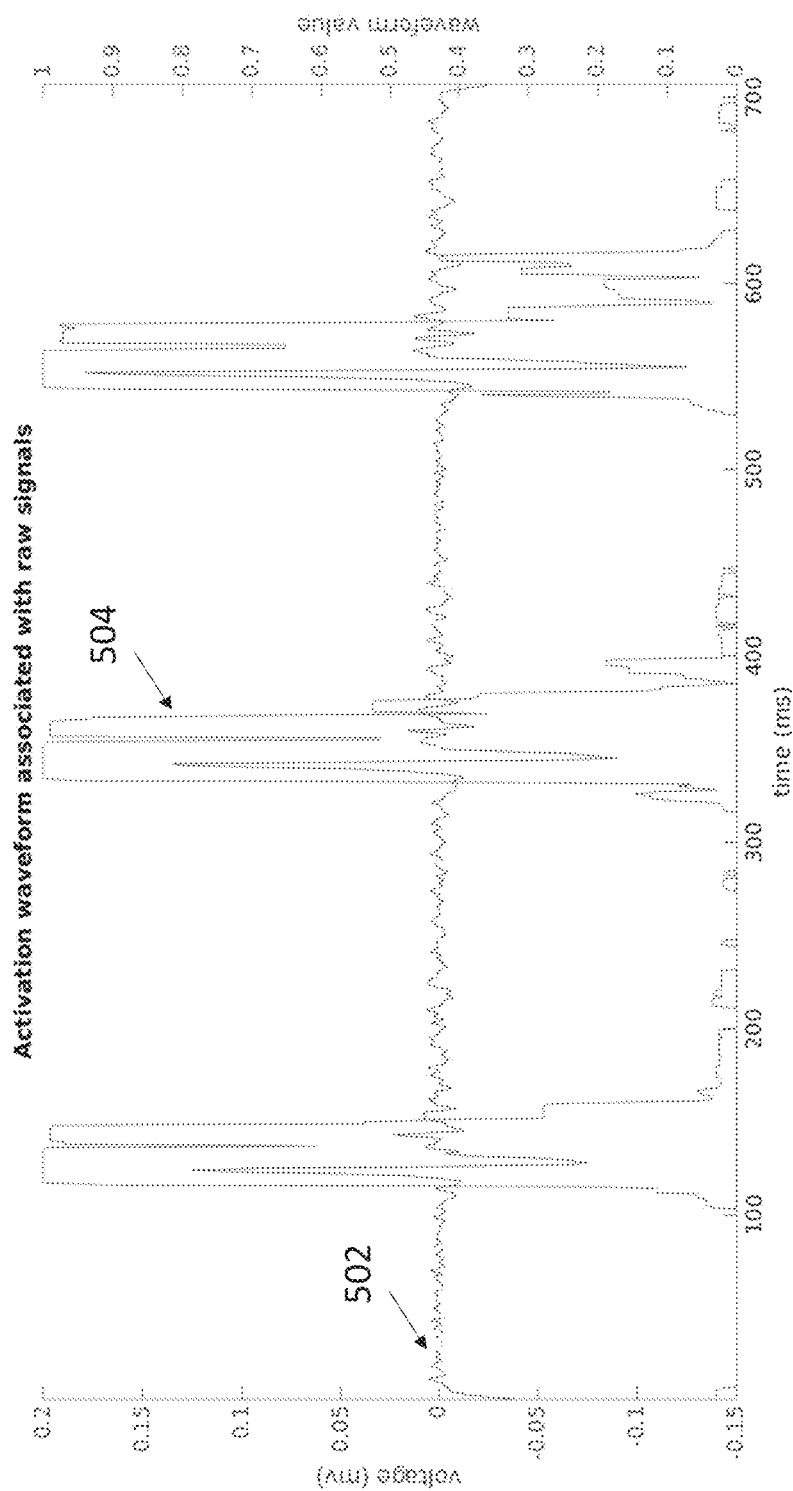
FIG. 5B depicts a waveform of raw cardiac electrical signals and an activation waveform corresponding to the cardiac electrical signals.

FIG. 5A depicts an exemplary graphical representation 500 illustrating electrical signals (in this case, EGMs) received from a mapping catheter, each representing a magnitude of a depolarization sequence of a heart during a predetermined time period. In this example, EGMs of a mapping catheter having 64 electrodes are shown. Each waveform may represent unipolar signals received from an electrode of the mapping catheter. FIG. 5B depicts a waveform of a raw cardiac electrical signal 502 and an activation waveform 504 corresponding to the cardiac electrical signal 502.

Referring back to FIG. 4A, the system receives a set of window parameters (415A), for example, to facilitate the determination of the local cycle length. In one embodiment, the set of window parameters include a range of window size (e.g., minimum window size and maximum window size). In one example, the range of window size can be from 120-300 milliseconds, although it is emphasized that this window size range is exemplary only and is in no way limiting. In one embodiment, the set of window parameters include a window increment. The system determines a set of confidence values (420A), where each confidence value corresponds to a window size and the confidence values are calculated iterating through the window sizes in the range of window size. In one embodiment, the window size of each iteration is increased by the window increment size. In some embodiments, for each window size (425A), a number of steps (e.g., 430A-450A) are conducted. First, a position of a central window is selected (430A). As used herein, a position of a window (i.e., time window or sample window) refers to the center point of the window. In one embodiment, the position of the central window is selected based on a beat location. For example, the center point of the central window is set as the beat location. The beat location can be determined, for example, using aspects of a system as described U.S. Pat. No. 9,002,442, entitled "BEAT ALIGNMENT AND SELECTION FOR CARDIAC MAPPING," the disclosures of which are hereby expressly incorporated herein by reference. In some embodiments, the position of the central window is not selected based on a beat location. In some cases, the position of the central window is selected in the waveform data points, for example, with a regular gap between two adjacent central windows (e.g., every 15 ms).

Figure 5C:
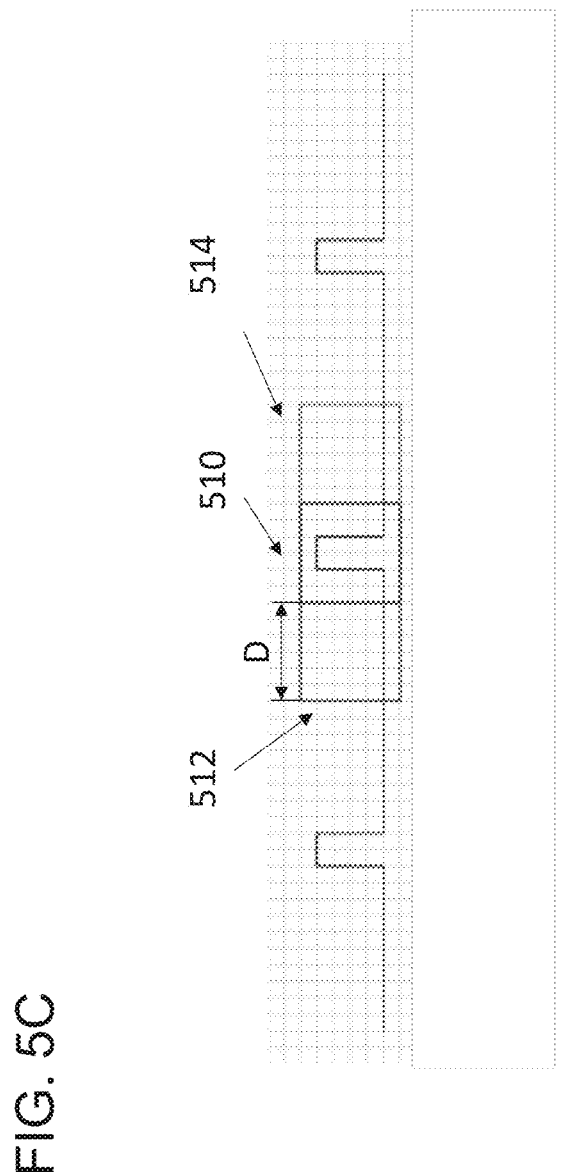
FIG. 5C shows an illustrative example of a central window, a backward shifted window and a forward shifted window.
Figure 5D:
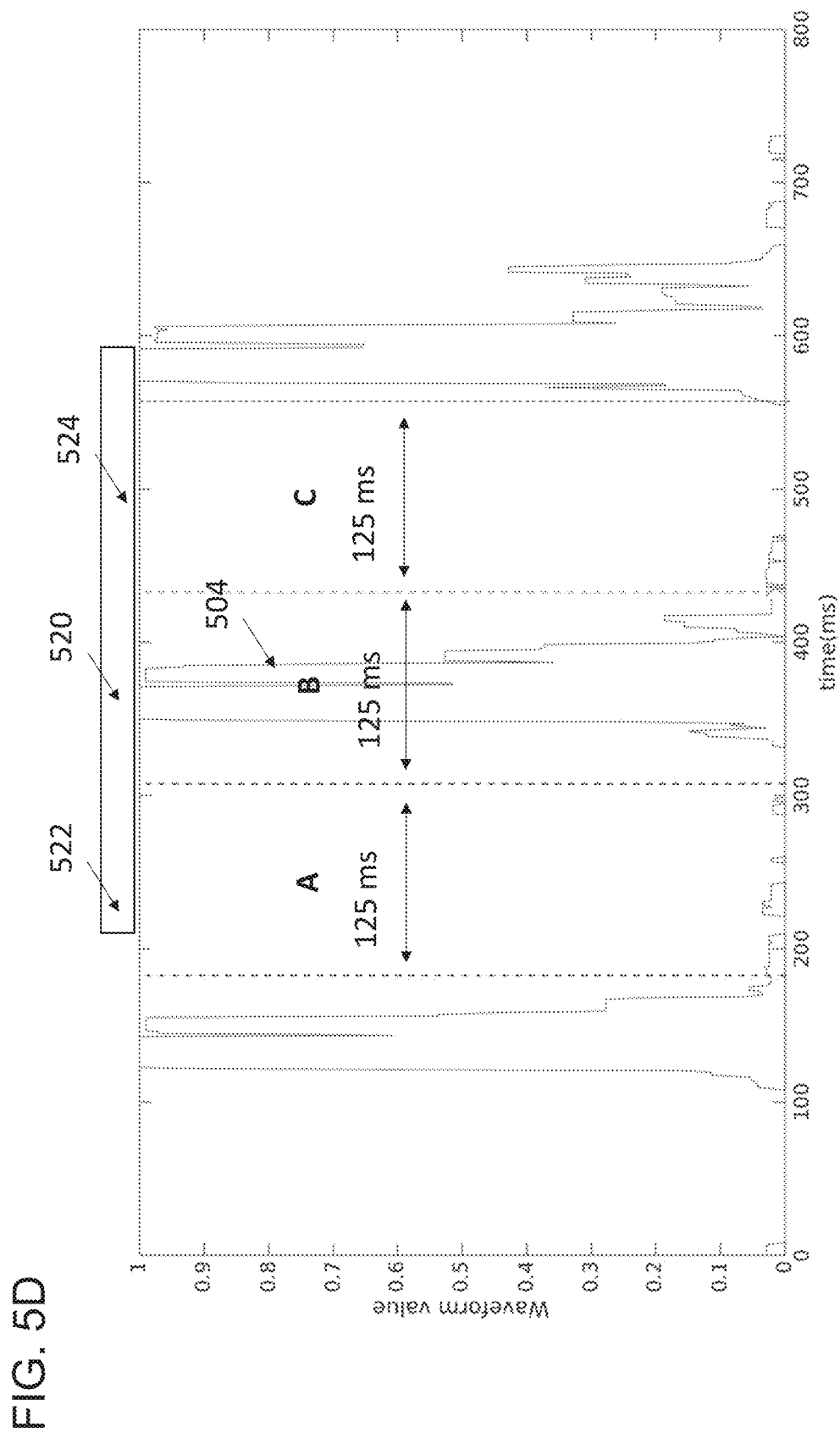
FIG. 5D shows an example activation waveform with a central window, a backward shifted window, and a forward shifted window.

Next, a backward correlation of the activation waveform in the central window and the activation waveform in a backward shifted window is calculated (435A), where the backward shifted window is the central window shifted backward. In some cases, the backward shifted window is the central window shifted backward by the size of the central window. Further, a forward correlation of the activation waveform in the central window and the activation waveform in a forward shifted window is calculated (440A), where the forward shifted window is the central window shifted forward. In some cases, the forward shifted window is the central window shifted forward by the size of the central window. FIG. 5C shows an illustrative example of a central window 510, a backward shifted window 512 and a forward shifted window 514, each with a window size D, where the correlation of the central window and the backward shifted window is low and the correlation of the central window and the forward shifted window is also low. FIG. 5D shows an example activation waveform 504 and a central window 520 (window B), a backward shifted window 522 (window A), and a forward shifted window 524 (window C), each with a window size of 125 ms.

Figure 5E:
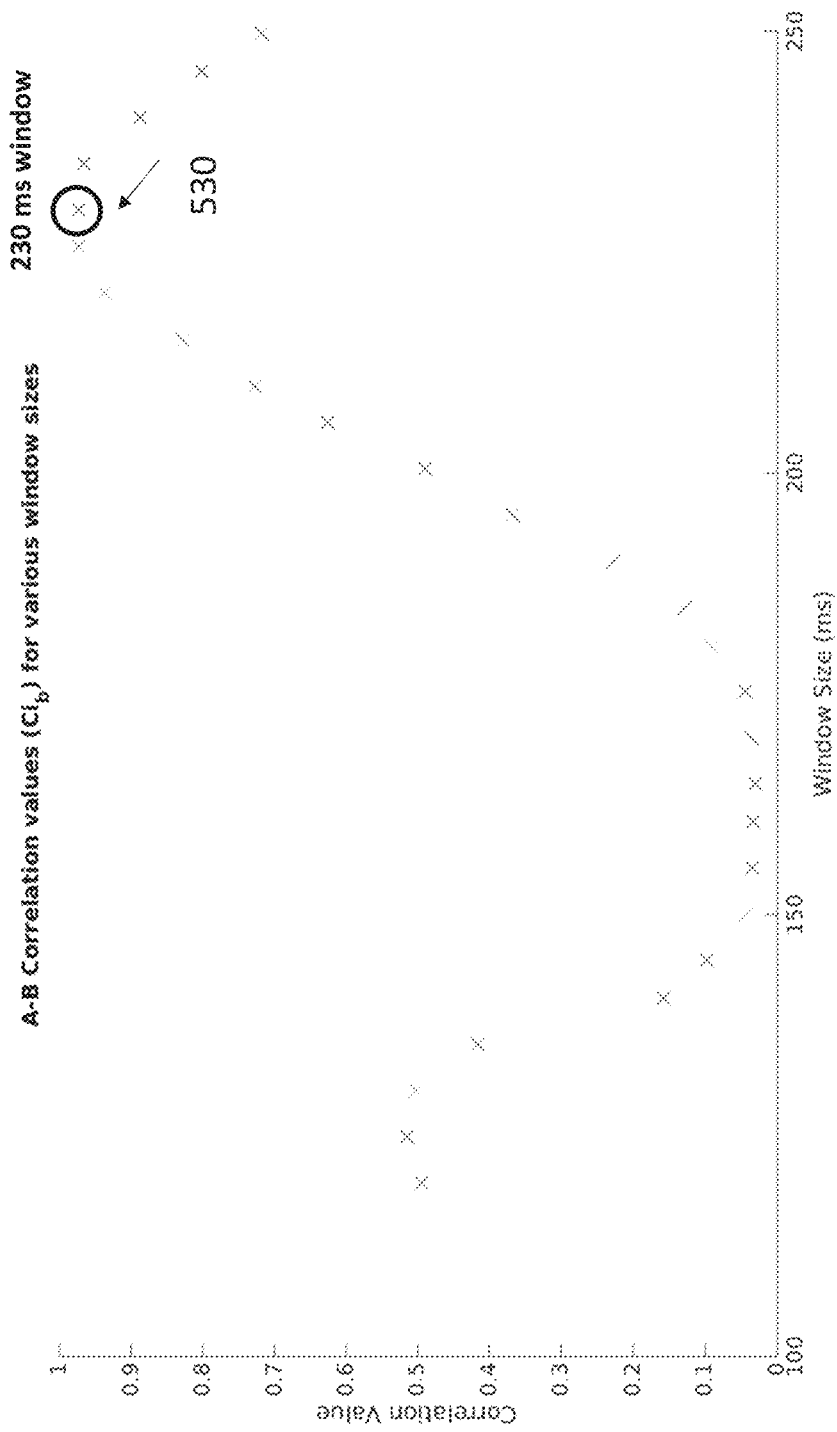
FIG. 5E shows an illustrative example of a set of correlation values of different window sizes.
Figure 5F:
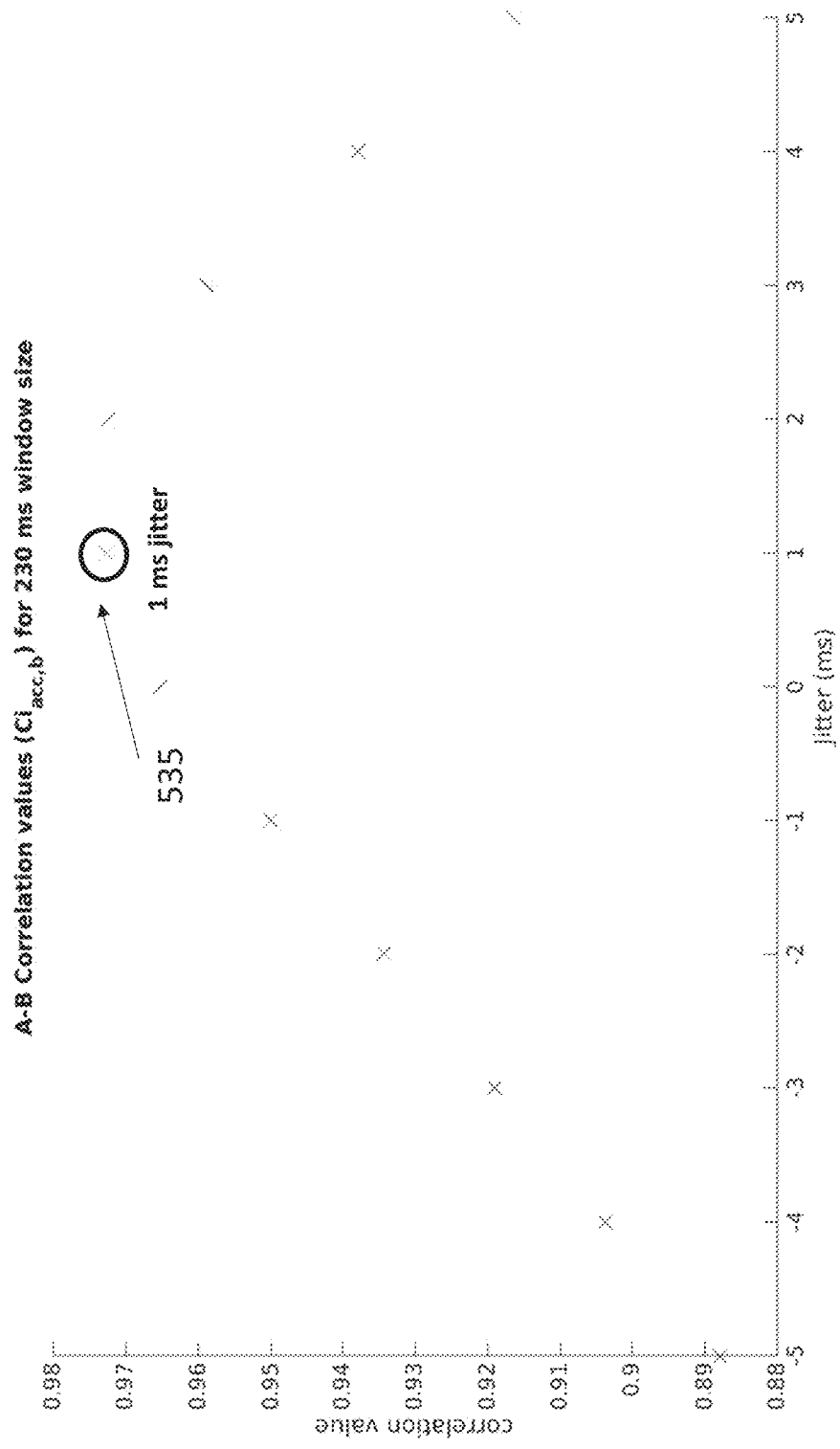
FIG. 5F shows one illustrative example of a set of channel correlations for windows with a jittering range of −5 ms to 5 ms.
Figure 5G:
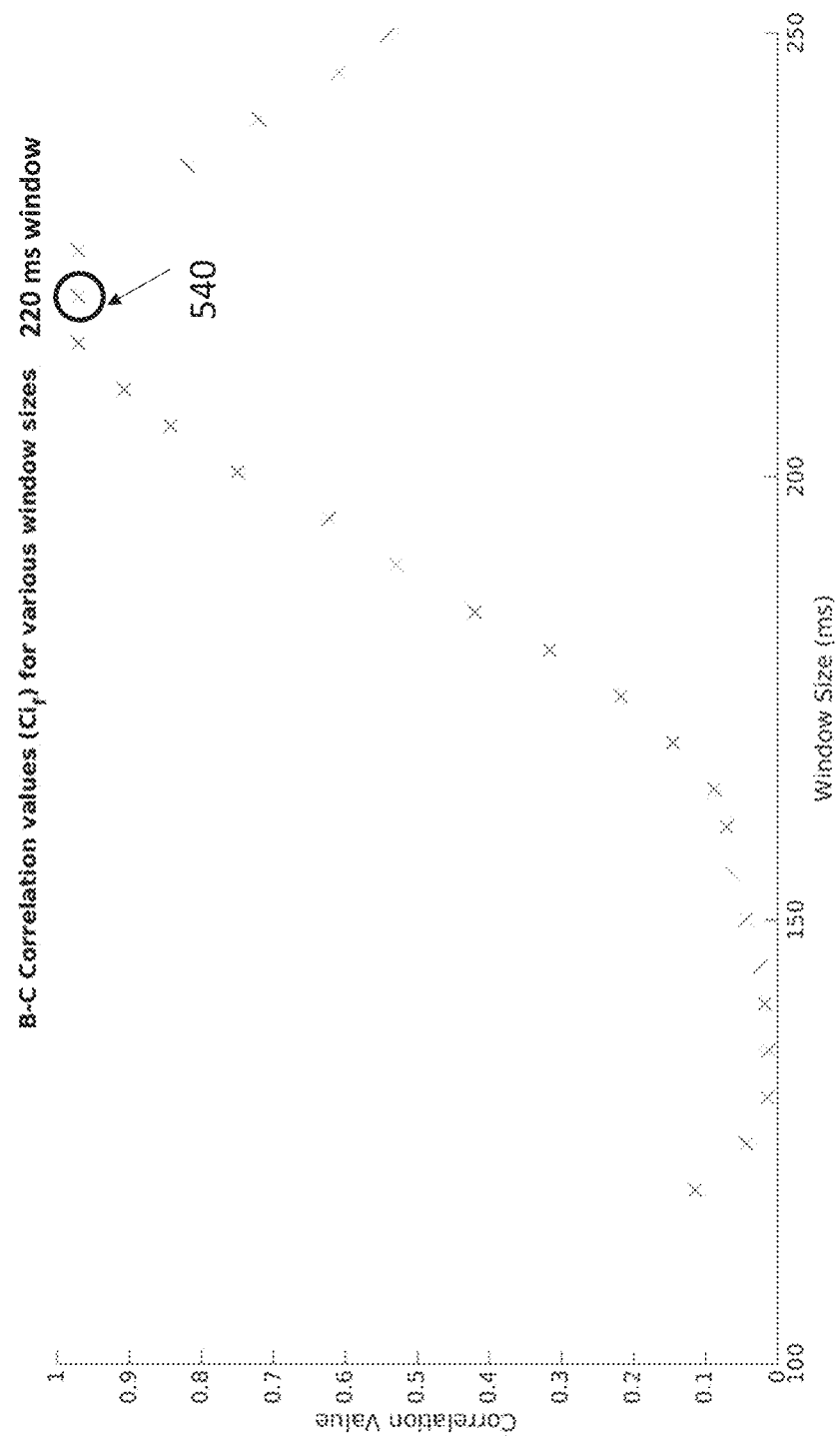
FIG. 5G shows another illustrative example of a set of correlation values of different window sizes.

In one example, a correlation of two sets of data, A(s) and B(s), is calculated using equation (1) below:

$$C = f(A(s), B(s)) \qquad (1),$$

where C is the correlation value, f is a selected correlation function. In one case, the correlation function is sensitive to amplitude similarity, for example, the correlation value C is the highest when A(s) and B(s) has a high level of similarity and A(s) and B(s) have relative high amplitude values. FIG. 5E shows one example of a set of correlation values of different window sizes. In this example, correlations of central windows and backward shifted windows of different sizes are shown. As illustrated, the correlation value has a maximum value (i.e., 530) at window size of 230 ms. FIG. 5G shows another illustrative example of a set of correlation values of different window sizes. In this example, correlations of central windows and forward shifted windows of different sizes are shown. As illustrated, the correlation has a maximum value (i.e., 540) at window size of 220 ms.

Referring back to FIG. 4A, a backward confidence value is determined based on the backward correlation (445A) and a forward confidence value is determined based on the forward correlation (450A), where the backward confidence value and the forward confidence value are added to the set of confidence values. In some cases, the confidence value is determined based on a function of the correlation values and activation weights. Activation weights are related to amplitudes of data points of the activation waveform in a respective window (e.g., backward shifted window, central window, and forward shifted window). In some cases, activation weights are related maximum amplitude of the activation waveform of a respective window. For example, the confidence value is calculated using equation (2):

$$Cf = fc(fw(AW), C) \qquad (2),$$

where Cf is the confidence value, AW is an activation weight, fw is a function to determine weighted factors, C is the correlation value for a respective window, and fc is a function to determine confidence values. In one example, the function fw is a linear function, for example, to normalize the confidence value between 0 and 1 and in proportion to the activation weight. In another example, the function fw is a binary function, such as weighted factor is 0 if the activation weight is lower than a threshold, weighted factor is 1 if the activation weight is higher than the threshold. In yet another example, the function fw is an error function.

In some cases, the system determines a central weight factor associated with an amplitude of the activation waveform in the central window of a specific window size during the iteration 425A. The backward confidence value for the specific window size may be determined based on the central weight factor, and the forward confidence value for the specific window size may also be determined based on the central weight factor. In some cases, the system further determines a backward weight factor associated with an amplitude of the activation waveform in the backward shifted window of the specific window and/or a forward weight factor associated with an amplitude of the activation waveform in the forward shifted window. The backward confidence value for the specific window size may be determined based on the backward correlation, the central weight factor and the backward weight factor, and the forward confidence value for the specific window size may be determined based on the forward correlation, the central weight factor and the forward weight factor.

In one embodiment, the central weight factor is determined by applying a non-linear function to an associated amplitude (e.g., maximum amplitude) of the activation waveform in the central window. In another embodiment, the central weight factor is determined by applying an error function to the associated amplitude of the activation waveform in the central window. In yet another embodiment, the central weight factor is determined by applying a linear function to the associated amplitude of the activation waveform in the central window.

In some embodiments, the electrophysiology system determines the correlation values and confidence values across different window sizes within a range and compare the set of confidence values to select a designated confidence value and a selected window size corresponding to the designated confidence value (455A). In some cases, the designated confidence value is the maximum confidence value in the set. As described above, each confidence value is determined with a corresponding window size. In the example illustrated in FIG. 5E, a designated confidence value can be the data point 530, with a corresponding window size of 230 ms. In the example illustrated in FIG. 5G, a designated confidence value can be the data point 540, with a corresponding window size of 220 ms.

Referring back to FIG. 4A, the electrophysiology system may determine a local cycle length based on the selected window size (460A). In some cases, the local cycle length is the selected window size. In some other cases, the local cycle length is determined based on the selected window size, for example, with an adjustment. In some cases, the system determines a duty cycle based on the activation waveform and the selected window size (465A). In some embodiments, the system determines the duty cycle based on the activation waveform in the central window having the selected window size. In some cases, the duty cycle is the average of amplitudes of sampling points of the activation waveform in the central window.

Figure 4B:
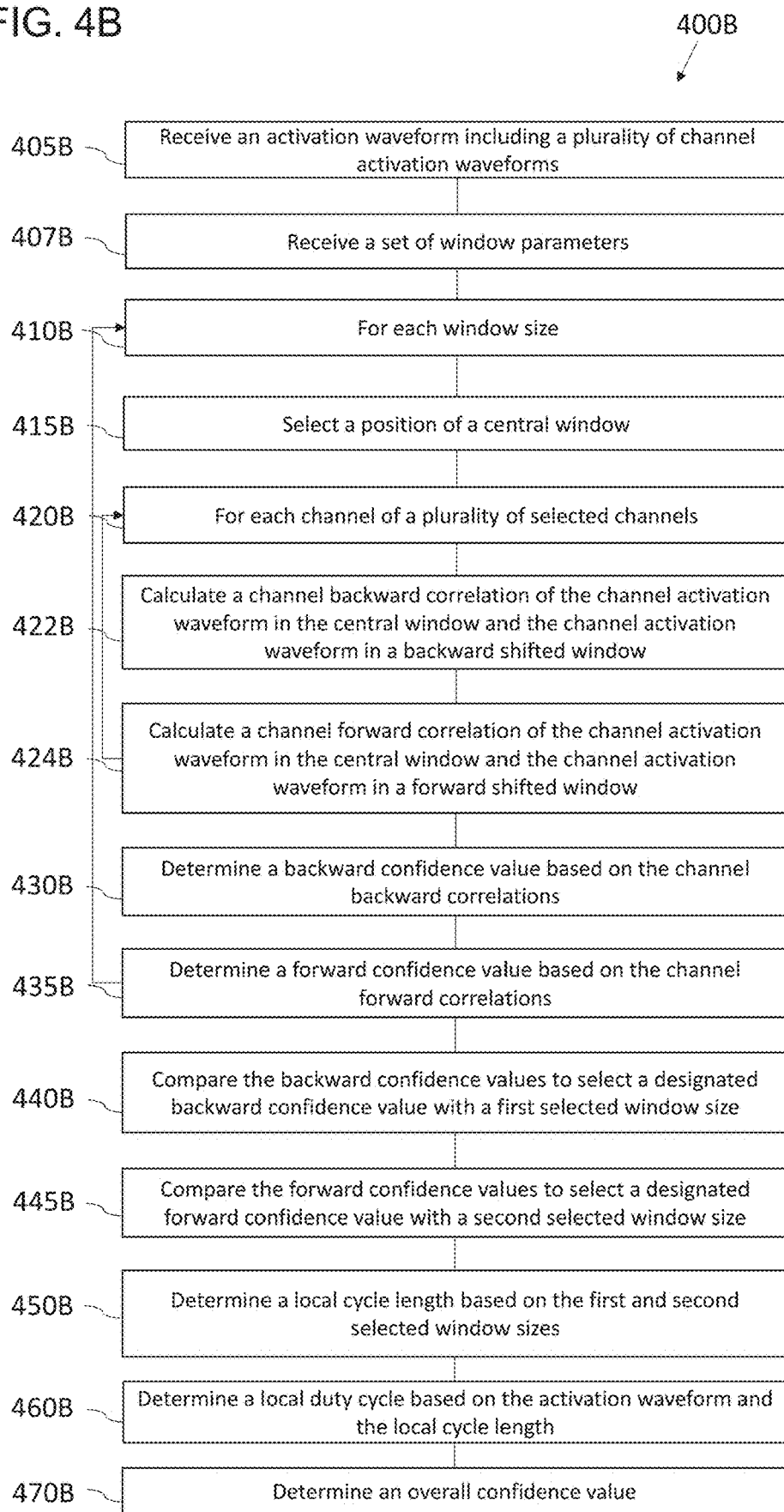

In some embodiments, the activation waveform is associated with data collected from a plurality of channels. For example, FIG. 5A illustrates cardiac electrical signals collected from 64 channels. In such embodiments, the activation waveform comprises a plurality of channel activation waveforms, and each of the plurality of channel activation waveform comprises activation waveform data for one of the plurality of channels. FIG. 4B is another example flow diagram depicting an illustrative method 400B of processing electrophysiological information across the plurality of channels, in accordance with some embodiments of the present disclosure. Aspects of embodiments of the method 400B may be performed, for example, by an electrophysiology system or a processing unit (e.g., the processing unit 120 depicted in FIG. 1, and/or the processing unit 200 depicted in FIG. 2). One or more steps of method 400B are optional and/or can be modified by one or more steps of other embodiments described herein. Additionally, one or more steps of other embodiments described herein may be added to the method 400B. The electrophysiology system receives an activation waveform including a plurality of channel activation waveforms (405B), each of the plurality of channel activation waveform corresponding to a respective one of a plurality of selected channels. In some cases, the selected channels include all channels of a mapping catheter. In some cases, the selected channels include channels meeting certain criteria. In some embodiments, the activation waveform is associated with a section of cardiac electrical signals, for example, a signal section associated with a heartbeat, a predetermined sample size, a predetermine time duration, or the like.

The system receives a set of window parameters (407B), including, for example, the range of window sizes and window size increment. The system is configured to iterate through the window sizes in the range and determine the correlation and confidence values related to the activation waveform data. For each window size (410B), the system selects a position of central window (415B). For each channel of a plurality of selected channels (420B), each channel associated with a channel activation waveform, the electrophysiology system calculates a channel backward correlation of the channel activation waveform in the central window and the channel activation waveform in the backward shifted window (422B); and calculates a channel forward correlation of the channel activation waveform in the central window and the channel activation waveform in the forward shifted window (424B). The system further determines a backward confidence value based on the backward correlations calculated for each selected channel (430B). The system also determines a forward confidence value based on the forward correlations calculated for each selected channel (435B). In one example, the confidence value is determined using equation (3) below:

$$Cf = \Sigma_{Ch=1}^{Nch} fc(AW(Ch), C(Ch)) \tag{3}$$

where Cf is the confidence value, Ch is the channel, NCh is the total number of selected channels, AW(Ch) is an activation weight factor for the channel, C(Ch) is the correlation value of the channel for a respective window, and fc is a function to determine confidence values. In some embodiments, the computed confidence value Cf is normalized, for example, in a range of 0-1.

In some embodiments, the electrophysiology system compares the backward confidence values, each for a window size, to select a designated backward confidence value corresponding with a first selected window size (i.e., backward local cycle length) (440B). In some embodiments, the electrophysiology system further compares the forward confidence values, each for a window size, to select a designated forward confidence value corresponding with a second selected window size (i.e., forward local cycle length)

(445B). In some cases, a designated confidence value is the highest confidence value in the set. Next, the system may determine a local cycle length based on the first selected window size and the second selected window size (450B). In one embodiment, the local cycle length is the average of the first selected window size and the second selected window size. For example, with the first selected window size as 232 ms and the second selected window size as 228 ms, the local cycle length is 230 ms. In some embodiments, the system determines a local duty cycle based on the activation waveform and the local cycle length (460B). In one embodiment, the system selects, for each sampling point in the central window of the local cycle length, the maximum amplitude of the channel activation waveform across the plurality of selected channels. In some embodiments, the system may calculate an average of these selected maximum amplitudes of the central window as the local duty cycle.

In some embodiments, the electrophysiology system further determines a section confidence value (470B) for the activation waveform. In one embodiment, the section confidence value is determined based on the designated backward confidence value and the designated forward confidence value. In one embodiment, the section confidence value is determined based on the smaller of the designated backward confidence value and the designated forward confidence value. In another embodiment, the system calculates backward-forward correlations of the channel activation waveform in the backward shifted window and the channel activation waveform in forward shifted window for each of the selected channels. The system further determines a backward-forward confidence value, for example, using equation (3), for each window size. After that, the system selects a designated backward-forward confidence value from the sets of backward-forward confidence values for the various window sizes. For example, the designated backward-forward confidence value is the highest value in the set of backward-forward confidence values. In one embodiment, the section confidence value is determined based on the designated backward confidence value, the designated forward confidence value and the designated backward-forward confidence value. In one embodiment, the section confidence value is determined based on the smallest value of the designated backward confidence value, the designated forward confidence value and the designated backward-forward confidence value. In some embodiments, the section confidence value is further determined based on the differences of the first selected window size (i.e., backward local cycle length) and the second selected window size (i.e., forward local cycle length).

Figure 4C:
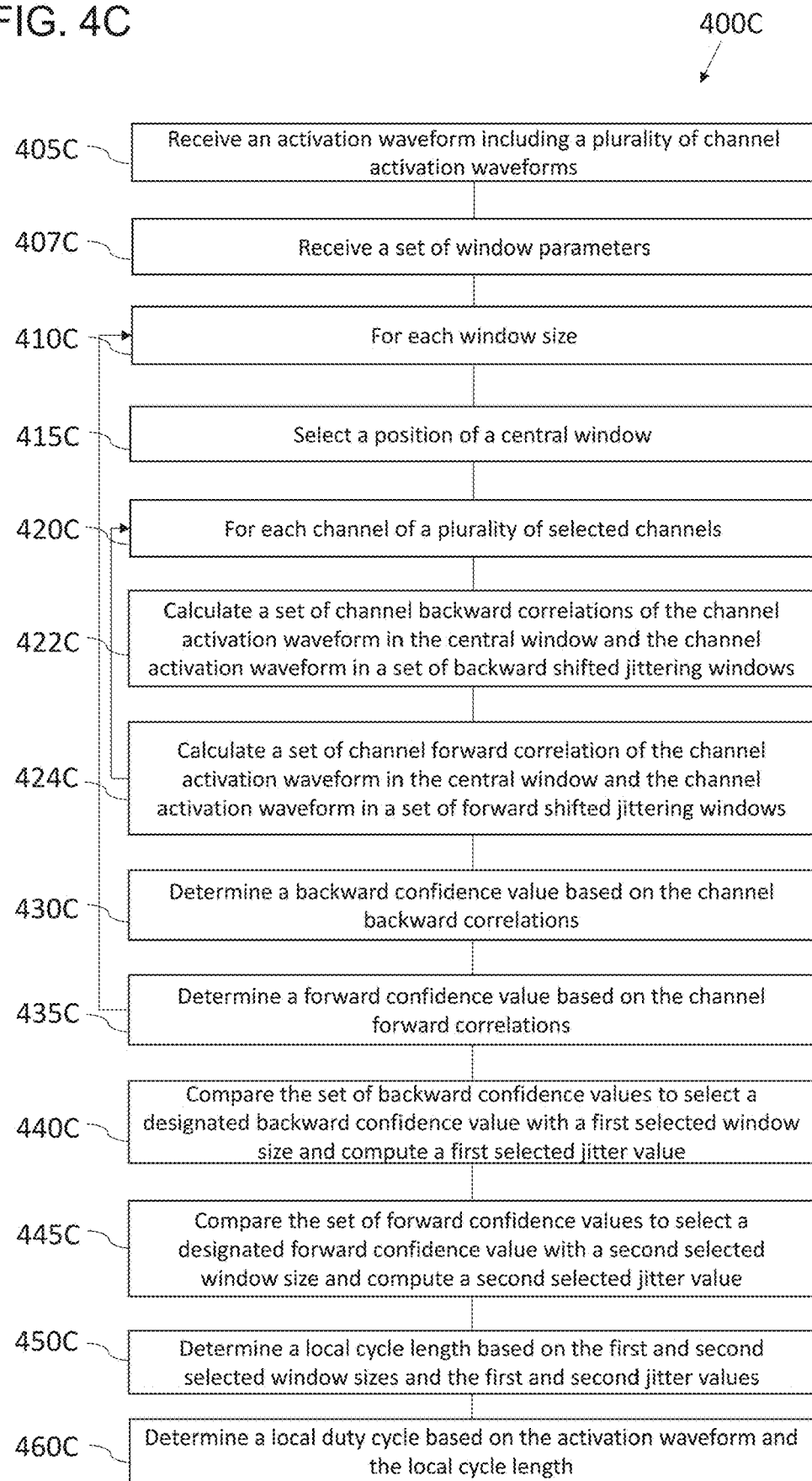

In some embodiments, the electrophysiology system may use a jitter interval to slightly shift windows to reduce the amount of computation with relative large window increment. FIG. 4C is another example flow diagram depicting an illustrative method 400C of processing electrophysiological information, in accordance with some embodiments of the present disclosure. Aspects of embodiments of the method 400C may be performed, for example, by an electrophysiology system or a processing unit (e.g., the processing unit 120 depicted in FIG. 1, the processing unit 200 depicted in FIG. 2, a computational processing unit, and/or a graphical processing unit). One or more steps of method 400C are optional and/or can be modified by one or more steps of other embodiments described herein. Additionally, one or more steps of other embodiments described herein may be added to the method 400C. The electrophysiology system receives activation waveform including a plurality of channel activation waveforms, each channel waveform corresponding to a plurality of selected channels (405C). The system receives a set of window parameters (407C), including, for example, the range of window sizes (e.g., 120 ms to 250 ms), window size increment (e.g., 10 ms), the range of jitters (e.g., −5 ms to 5 ms) and the jitter interval (e.g., 1 ms). In one embodiment, the jitter interval is smaller than the window size increment.

The system is configured to iterate through the window sizes in the range, for each window size (410C), the system selects a position of central window (415C). Next, for each channel of a plurality of selected channels (420C), each channel associated with a channel activation waveform, the electrophysiology system calculates a set of channel backward correlations based on the channel activation waveform in the central window and the channel activation waveform in a set of backward shifted jittered windows (422C); and calculates a set of channel forward correlations based on the channel activation waveform in the central window and the channel activation waveform in a set of forward shifted jittered windows (424C). In some cases, the selected channels include all channels of a mapping catheter. In some cases, the selected channels include channels meeting certain criteria. In some embodiments, the channel activation waveform is associated with a section of cardiac electrical signals of a channel, for example, a signal section associated with a heartbeat, a predetermined sample size, a predetermine time duration, or the like.

Figure 5H:
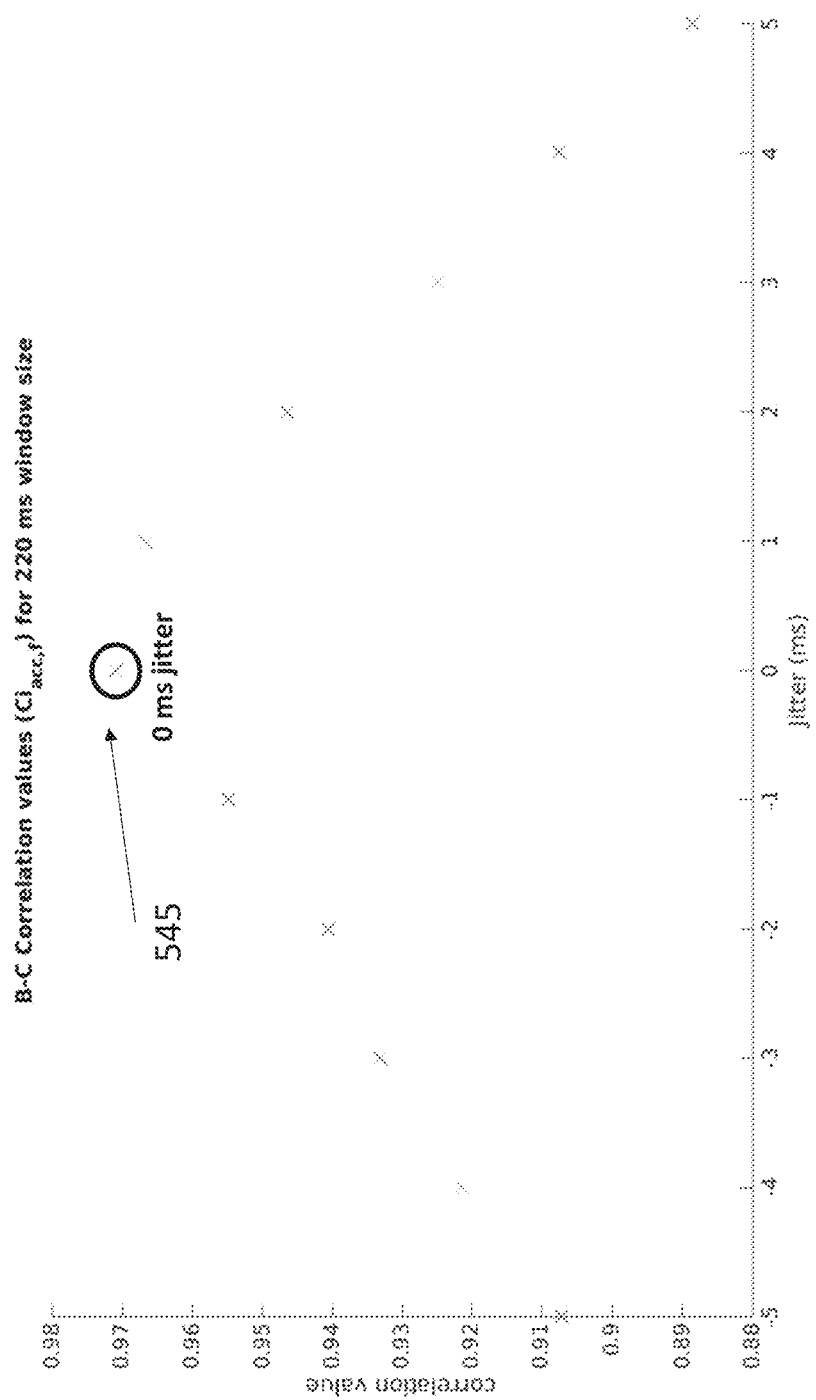
FIG. 5H shows another illustrative example of a set of channel correlations for windows with a jittering range of −5 ms to 5 ms.
Figure 51:
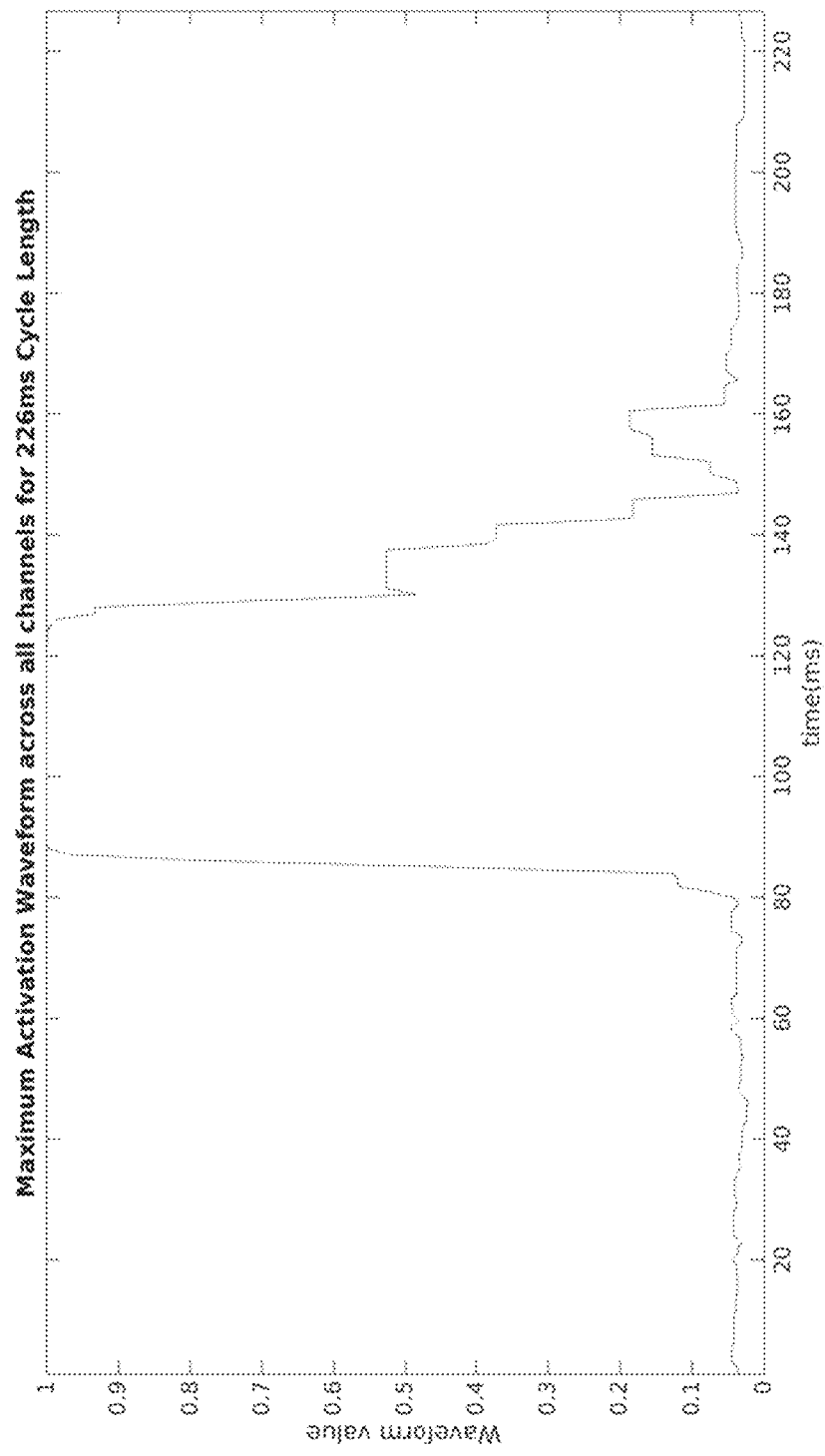

In some cases, each of the set of channel backward correlations is a correlation of the channel activation waveform in the central window and the channel activation waveform in the backward shifted window with a jitter adjustment within the range of jittering (e.g., −5 ms to 5 ms). In one example, assuming a central window at a position of 400 ms having a window size of 200 ms and the backward shifted window at a position of 200 ms, the set of backward shifted jittered windows include the windows at a position of 195 ms, 196 ms, 197 ms, 198 ms, 199 ms, 200 ms, 201 ms, 202 ms, 203 ms, 204 ms, and 205 ms. FIG. 5F shows one illustrative example of a set of channel backward correlations with a jittering range of −5 ms to 5 ms with a jittering interval of 1 ms. In some cases, each of the set of channel forward correlations is a correlation of the channel activation waveform in the central window and the channel activation waveform in the forward shifted window with a jitter adjustment within the range of jittering (e.g., −5 ms to 5 ms). In one example, assuming a central window at a position of 400 ms having a window size of 200 ms and the forward shifted window at a position of 600 ms, the set of forward shifted jittered windows include the windows at a position of 595 ms, 596 ms, 597 ms, 598 ms, 599 ms, 600 ms, 601 ms, 602 ms, 603 ms, 604 ms, and 605 ms. FIG. 5H shows an illustrative example of a set of channel forward correlations with a jittering range of −5 ms to 5 ms with a jittering interval of 1 ms.

In some embodiments, for a window size, the electrophysiology system selects a designated channel backward correlation in the set of channel backward correlations with a channel backward jitter value. In the example illustrated in FIG. 5F, the data point 535 is the designated channel backward correlation (e.g., 0.972) with the channel backward jitter value (e.g., 1 ms). In some embodiments, for a window size, the electrophysiology system selects a designated channel forward correlation in the set of channel forward correlations with a channel forward jitter value. In the example illustrated in FIG. 5H, the data point 545 is the designated channel forward correlation (e.g., 0.97) with the channel forward jitter value (e.g., 0 ms).

For each window size, the system further determines a backward confidence value based on the channel backward correlations (430C). In one embodiment, the channel backward correlations include the set of channel backward correlations of the channel activation waveform in the central window and the channel activation waveform in the set of backward shifted jittered windows for each of the selected channels. In one embodiment, for each selected channel, the channel backward correlations include the designated channel backward correlation. For each window size, the system also determines a forward confidence value based on the channel forward correlations (435C). In one embodiment, the channel forward correlations include the set of channel forward correlations of the channel activation waveform in the central window and the channel activation waveform in the set of forward shifted jittered windows. In one embodiment, for each selected channel, the channel forward correlations include the designated channel forward correlation.

In some embodiments, the electrophysiology system compares the set of backward confidence values, each for a window size, to select a designated backward confidence value corresponding with a first selected window size and compute a first selected jitter value (440C). In one embodiment, the designated backward confidence value is the highest backward confidence value across the window sizes. In one embodiment, the first selected window size is corresponding to the highest backward confidence value across the window sizes. In some cases, after the first selected window size is determined, the system computes a first select jitter value based on the amplitudes of the activation waveform in the backward shifted window and the channel backward jitter value across the window sizes. In some embodiments, the electrophysiology system further compares the set of forward confidence values, each for a window size, to select a designated forward confidence value corresponding with a second selected window size and compute a second selected jitter value (445C). In some cases, a designated forward confidence value is the highest forward confidence value in the set. In one embodiment, the first selected window size is corresponding to the highest forward confidence value across the window sizes. In some cases, after the second selected window size is determined, the system computes a second select jitter value based on the amplitudes of the activation waveform in the forward shifted window and the channel forward jitter values across the window sizes.

Next, the system may determine a local cycle length based on the first selected window size and the second selected window size (450C). In one embodiment, the local cycle length is the average of the first selected window size and the second selected window size. For example, the local cycle length is an average of 231 ms window size and 220 ms window size. In another embodiment, the system determines a local cycle length based on the selected window size adjusted by the jitter value. In some embodiments, the system determines a local duty cycle based on the activation waveform and the local cycle length (460C). In one embodiment, the system selects, for each sampling point of the central window of the local cycle length, the maximum amplitude of the channel activation waveform of the plurality of selected channels. In some embodiments, the system may calculate an average of these selected amplitudes of the window as the local duty cycle. In one embodiment, the system generates a maximum waveform based on the plurality of channel activation waveforms in the selected central window, where each data point of the maximum waveform has a maximum value of the plurality of channel activation waveforms among the plurality of selected channels at a corresponding data point. FIG. 5I depicts an illustrative example of a maximum waveform. In one embodiment, the system determines a duty cycle based on maximum waveform. In one case, the duty cycle is determined to be the average value of data points of the maximum waveform.

Figure 4D:
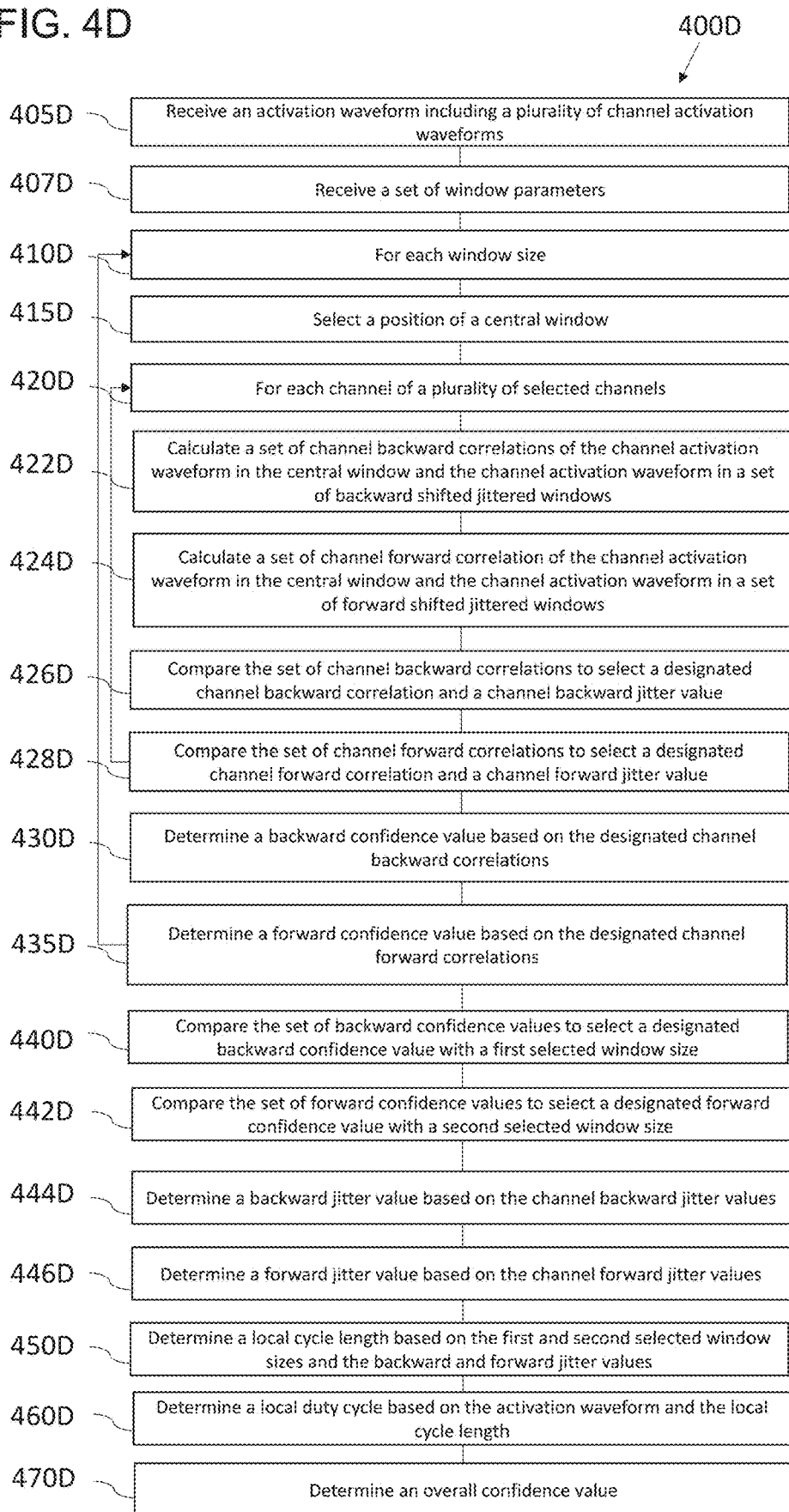

FIG. 4D is yet another example flow diagram depicting an illustrative method 400D of processing electrophysiological information, in accordance with some embodiments of the present disclosure. Aspects of embodiments of the method 400D may be performed, for example, by an electrophysiology system or a processing unit (e.g., the processing unit 120 depicted in FIG. 1, and/or the processing unit 200 depicted in FIG. 2). One or more steps of method 400D are optional and/or can be modified by one or more steps of other embodiments described herein. Additionally, one or more steps of other embodiments described herein may be added to the method 400D. The electrophysiology system receives activation waveform including a plurality of channel activation waveforms, each of the channel activation waveform corresponding to one of a plurality of selected channels (405D).

In some cases, the selected channels include all channels of a mapping catheter. In some cases, the selected channels include channels meeting certain criteria. In some embodiments, the activation waveform is associated with a section of cardiac electrical signals, for example, a signal section associated with a heartbeat, a predetermined sample size, a predetermine time duration, or the like. The system receives a set of window parameters (407D), including, for example, the range of window sizes (e.g., 120 ms to 250 ms), window size increment (e.g., 10 ms), the range of jittering (e.g., −5 ms to 5 ms) and the jitter interval (e.g., 1 ms). In one embodiment, the jitter interval is smaller than the window size increment. The system is configured to iterate through the window sizes in the range (e.g., 120 ms, 130 ms, etc.).

For each window size (410D), the system selects a position of central window (415D). For each channel of a plurality of selected channels (420D), each one associated with a channel activation waveform, the electrophysiology system calculates a set of channel backward correlations of the channel activation waveform in the central window and the channel activation waveform in a set of backward shifted jittered windows (422D); and calculates a set of channel forward correlations of the channel activation waveform in the central window and the channel activation waveform in a set of forward shifted jittered windows (424D). In some cases, each of the set of channel backward correlations is a correlation of the channel activation waveform in the central window and the channel activation waveform in the backward shifted window with a jitter adjustment within the range of jittering (e.g., −5 ms to 5 ms). In one example, a correlation of the set of channel backward correlations for a specific window size N, a specific channel Ch and a specific jitter J can be calculated using equation (4) below:

$$Ci_B(Ch, J) = \frac{\sum_{k=1}^{N} Central(s) * Backward(s)}{\sqrt{\sum_{k=1}^{N} Central(s)^2 \times \sum_{k=1}^{N} Backward(s)^2}}, \quad (4)$$

where $Ci_B(Ch, J)$ is the correlation value, Ch is the specific channel, J is the specific jitter value, N is the size of window, s is a sample point, Central(s) is the amplitude of the activation waveform of the central window at the sample point s, and Backward(s) is the amplitude of the activation waveform of the backward shifted jittered (by J) window at the sample point s.

In some cases, each of the set of channel forward correlations is a correlation of the channel activation waveform in the central window and the channel activation waveform in the forward shifted window with a jitter adjustment within the range of jittering (e.g., −5 ms to 5 ms). In one example, a correlation of the set of channel forward correlations for a specific window size N, a specific channel Ch and a specific jitter J can be calculated using equation (5) below:

$$Ci_F(Ch, J) = \frac{\sum_{s=1}^{N} \text{Central}(s) * \text{Backward}(s)}{\sqrt{\sum_{s=1}^{N} \text{Central}(s)^2 \times \sum_{s=1}^{N} \text{Backward}(s)^2}}, \quad (5)$$

where $Ci_F(Ch, J)$ is the correlation value, Ch is the specific channel, J is the specific jitter value, N is the size of window, s is a sample point, Central(s) is the amplitude of the activation waveform of the central window at the sample point s, and Forward(s) is the amplitude of the activation waveform of the forward shifted jittered (by J) window at the sample point s.

In some embodiments, for each of the channels, the electrophysiology system compares the set of channel backward correlations to select a designated channel backward correlation and a channel backward jitter value corresponding to the designated channel backward correlation (426D). In some cases, the designated channel backward correlation is the highest correlation value in the set of the channel backward correlations. In the example illustrated in FIG. 5F, the correlation at data point 535 is the designated channel backward correlation (e.g., 0.972) with the corresponding channel backward jitter value (e.g., 1 ms). In some embodiments, for each channel, the system may compare the set of channel forward correlations to select a designated channel forward correlation and a channel forward jitter value corresponding to the designated channel forward correlation (428D). In the example illustrated in FIG. 5H, the correlation at data point 545 is the designated channel forward correlation (e.g., 0.97) with the corresponding channel forward jitter value (e.g., 0 ms).

For each window size, the system further determines a backward confidence value based on the designated channel backward correlations (430D). In one embodiment, the designated channel backward correlations include the designated channel backward correlation for each of the selected channels. In some cases, the system determines an activation weight $W_C$ for the central window of all selected channels. In some cases, the system determines an activation weight $W_B$ for the backward shifted window of all selected channels. In some cases, the system determines an activation weight $W_F$ for the forward shifted window of all selected channels. In some embodiments, the activation weight across the selected channels is an indication of signal amplitude in the respective window. In some cases, the activation weight across the selected channels indicates whether an activation occurs within the respective window.

In some cases, the activation weight is determined based on the maximum value of the activation waveform. In some cases, the activation weight is determined based on a non-linear function applying to the maximum value of the activation waveform. In some cases, the activation weight is determined based on a linear function applying to the maximum value of the activation waveform. In some cases, the activation weight is determined based on a binary function applying to the maximum value of the activation waveform. In some cases, the activation weight is determined based on an error function applying to the maximum value of the activation waveform. In one example, a backward confidence value $Cf_B$ for a window size s can be calculated using equation (6) below:

$$Cf_B(s) = \frac{\sum_{Ch=1}^{NCh} W_B(Ch) \times C_B(Ch)}{\sum_{Ch=1}^{NCh} W_B(Ch)} \times \sqrt{W_C \times W_B}, \quad (6)$$

where $Cf_B(s)$ is the backward confidence value, $W_B(Ch)$ is the activation weight of the backward shifted window for a channel Ch, $C_B(Ch)$ is the designated channel backward correlation value at a channel Ch, Ch is a channel, NCh is the number of selected channels, $W_C$ is the activation weight of the central window across all selected channels, and $W_B$ is the activation weight of the backward shifted window across all selected channels. In some cases, an activation weight for a specific window and a specific channel (e.g., $W_C(Ch)$) is determined based on the highest amplitude of the activation waveform in the specific window for the specific channel. In some cases, an activation weight for a specific window and a specific channel (e.g., $W_C(Ch)$) is the highest amplitude of the activation waveform in the specific window for the specific channel.

For each window size, the system may also determine a forward confidence value based on the designated channel forward correlations (435D). In one embodiment, the designated channel forward correlations include the designated channel forward correlation for each channel. In one example, a forward confidence value $Cf_F$ for a window size s can be calculated using equation (7) below:

$$Cf_F(s) = \frac{\sum_{Ch=1}^{NCh} W_F(Ch) \times C_F(Ch)}{\sum_{Ch=1}^{NCh} W_F(Ch)} \times \sqrt{W_C \times W_F}, \quad (7)$$

where $Cf_F(s)$ is the forward confidence value, $W_F(Ch)$ is the activation weight of the forward shifted window for a channel Ch, $C_F(Ch)$ is the designated channel forward correlation value at a channel Ch, Ch is a channel, NCh is the number of selected channels, $W_C$ is the activation weight of the central window across all selected channels, and $W_F$ is the activation weight of the forward shifted window across all selected channels.

In some embodiments, the electrophysiology system compares the set of backward confidence values, each for a window size, to select a designated backward confidence value corresponding with a first selected window size (440D). In some embodiments, the electrophysiology system further compares the set of forward confidence values, each for a window size, to select a designated forward confidence value corresponding with a second selected window size (442D). In one embodiment, the designated confidence value is the highest confidence value in the set. In some embodiments, the system determines a backward jitter value based on the channel backward jitter values (444D), one channel backward jitter value for each channel. In one example, the backward jitter value $J_B$ can be calculated using equation (8) below:

$$J_B = \frac{\sum_{Ch=1}^{NCh} W_B(Ch) \times C_B(Ch)}{\sum_{Ch=1}^{NCh} W_B(Ch)}, \quad (8)$$

where $J_B$ is the backward jitter value, $W_B(Ch)$ is the activation weight of the backward shifted window for a channel Ch, $J_B(Ch)$ is the channel backward jitter value for a channel Ch, Ch is a channel, NCh is the number of selected channels. In some cases, an activation weight for a specific window and a specific channel (e.g., $W_B(Ch)$) is the highest amplitude of the activation waveform in the specific window for the specific channel.

In some embodiments, the system determines a forward jitter value based on the channel forward jitter values (446D), one channel forward jitter value for each channel. In one example, the backward jitter value $J_F$ can be calculated using equation (9) below:

$$J_F = \frac{\sum_{Ch=1}^{NCh} W_F(Ch) \times J_F(Ch)}{\sum_{Ch=1}^{NCh} W_F(Ch)}, \quad (9)$$

where $J_F$ is the backward jitter value, $W_F(Ch)$ is the activation weight of the forward shifted window for a channel Ch, $J_F(Ch)$ is the channel backward jitter value for a channel Ch, Ch is a channel, NCh is the number of selected channels. In some cases, an activation weight for a specific window and a specific channel (e.g., $W_F(Ch)$) is the highest amplitude of the activation waveform in the specific window for the specific channel.

Next, the system may determine a local cycle length based on the first selected and the second selected window sizes and the backward and forward jitter values (450D). In one embodiment, the local cycle length is the average of the first selected window size adjusted by the backward jitter value and the second selected window size adjusted by the forward jitter value. For example, with the first selected window size of 230 ms window size and backward jitter value of 1 ms, and the second selected window size of 220 ms and forward jitter value of 0 ms, the local cycle length is 226 ms. In some embodiments, the system determines a local duty cycle based on the activation waveform and the local cycle length (460D). In one embodiment, the system selects, for each sampling point of the central window of the local cycle length, the maximum amplitude of the channel activation waveform of the plurality of selected channels. In some embodiments, the system may calculate an average of these selected amplitudes of the window as the local duty cycle. In one embodiment, the system generates a maximum waveform based on the plurality of channel activation waveforms in the selected central window, where each data point of the maximum waveform has a maximum value of the plurality of channel activation waveforms among the plurality of selected channels at a corresponding data point. FIG. 5I illustrates one example of a maximum activation waveform across selected channels (e.g., 64 channels) for the local cycle length (e.g., 226 ms).

In one embodiment, the system determines a duty cycle based on maximum waveform. In one case, the duty cycle is determined to be the average value of data points of the maximum waveform. In some embodiments, the electrophysiology system determines a section confidence value (470D). In one embodiment, the section confidence value is determined based on the designated backward confidence value and the designated forward confidence value. In one embodiment, the section confidence value is determined based on the smaller value of the designated backward confidence value and the designated forward confidence value. In another embodiment, the system calculates backward-forward correlations, each correlation as a correlation of the channel activation waveform in the backward shifted window and the channel activation waveform in forward shifted window for each of the selected channels. The backward-forward correlations can be determined using an embodiment similar to any one of the embodiments for determining forward correlations and backward correlations. The system further determines a backward-forward confidence value based on the backward-forward correlations.

In one example, a backward-forward confidence value $Cf_{BF}$ for a window size s can be calculated using equation (10) below:

$$Cf_{BF}(s) = \frac{\sum_{Ch=1}^{NCh} W_{BF}(Ch) \times C_{BF}(Ch)}{\sum_{Ch=1}^{NCh} W_{BF}(Ch)} \times \sqrt{W_B \times W_F}, \quad (10)$$

where $Cf_{BF}(s)$ is the backward-forward confidence value, $W_{BF}(Ch)$ is the activation weight of the backward and forward shifted windows for a channel Ch, $C_{BF}(Ch)$ is the designated channel backward-forward correlation value at a channel Ch, Ch is a channel, NCh is the number of selected channels, $W_B$ is the activation weight of the backward shifted window across all selected channels, and $W_F$ is the activation weight of the forward shifted window across all selected channels. In some cases, an activation weight for specific window(s) and a specific channel (e.g., $W_C(Ch)$) is determined based on the highest amplitude of the activation waveform in the specific window(s) for the specific channel. In some cases, an activation weight for specific window(s) (e.g., backward shifted window and forward shifted window) and a specific channel (e.g., $W_{BF}(Ch)$) is the highest amplitude of the activation waveform in the specific window (s) for the specific channel.

The electrophysiology system may select a designated backward-forward confidence value from the sets of backward-forward confidence values for the various window sizes. For example, the designated backward-forward confidence value is the highest value in the set of backward-forward confidence values. In one embodiment, the section confidence value is determined based on the designated backward confidence value, the designated forward confidence value and the designated backward-forward confidence value. In one embodiment, the section confidence value is determined based on the smallest value of the designated backward confidence value, the designated forward confidence value and the designated backward-forward confidence value. In some embodiments, the section confidence value is further determined at least partially based on the differences of the first selected window size (i.e., backward local cycle length) and the second selected window size (i.e., forward local cycle length).

In some cases, the difference of the first selected window size and the second selected window size is input to a non-linear function to determine a weight factor. In some designs, a weight factor is a value between 0 and 1. In one example, the weight factor is set to a relatively large value (e.g., 1) when the difference of the first selected window size and the second selected window size is relatively small (e.g., 0). In another example, the weight factor is set to a relatively small value (e.g., 0.2) when the difference of the first selected window size and the second selected window size is relatively large (e.g., 30 ms). In some cases, the section confidence value is determined based on the weight factor, designated backward confidence value, the designated forward confidence value and the designated backward-forward confidence value. In some embodiments, the electrophysiology system includes a downweighting technique to remove signals lack of consistency. In some cases, the downweighting, for example, stochastic downweighting, is a form of outlier rejection. In some cases, the system downweighs the confidence of single beats or channels whose signals disagree with a local distribution. In some implementations, the stochastic downweighting is applied to remove false-positive highlights from spurious beats whose duty cycle or cycle length do not match the area around them.

It has demonstrated the presence of clear and consistent organization with discrete cycle length patterns in some areas of the atria during atrial fibrillation (AF). In embodiments of the present disclosure, aggregating the local cycle length measurement into a histogram (e.g., 1D local cycle length histogram) can allow the user to investigate these patterns both visually and/or by having a region of interest on a cardiac map. In some implementations, only sections of activation waveforms associated with heart beats with a confidence above the user-defined threshold are included in the histogram.

Figure 6:
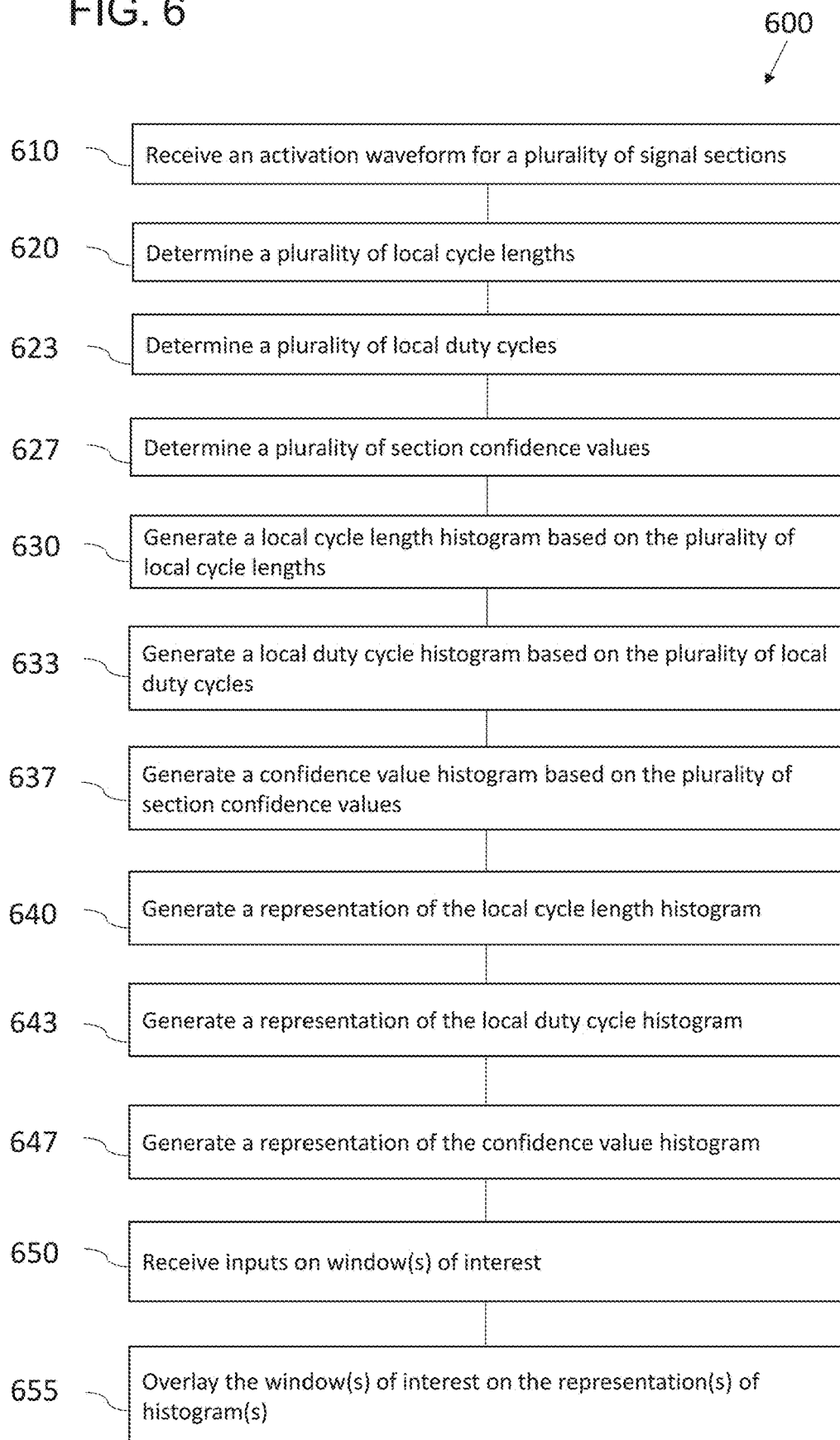
FIG. 6 is a flow diagram depicting an illustrative method of processing electrophysiological information to generate histograms, in accordance with embodiments of the subject matter disclosed herein.

FIG. 6 is a flow diagram depicting an illustrative method 600 of processing electrophysiology information to generate a histogram, in accordance with some embodiments of the present disclosure. Aspects of embodiments of the method 600 may be performed, for example, by an electrophysiology system or a processing unit (e.g., the processing unit 120 depicted in FIG. 1, and/or the processing unit 200 depicted in FIG. 2). One or more steps of method 600 are optional and/or can be modified by one or more steps of other embodiments described herein. Additionally, one or more steps of other embodiments described herein may be added to the method 600. First, the electrophysiology system receives an activation waveform (610), including a set of activation waveform data of a plurality of signal sections collected at a plurality of locations. In some cases, the plurality of locations include a part or all of the heart chamber. In some cases, the plurality of locations are selected based on, for example, a user input (e.g., an input via a user interface such as a graphical user interface), a system input (e.g., system configuration), a software input (e.g., an input via an application programming interface, web service, etc.), or the like. In some cases, the plurality of locations are selected within a predetermined radius of a probe (e.g., roving probe) location. In some designs, the roving probe can be moved around in the heart chamber and the roving probe location is changed accordingly. In some cases, the roving probe location are indicated by an input, for example, a user input, a system input, a software input, or the like. The system determines a plurality of local cycle lengths (620) corresponding to the plurality of signal sections using any one of the embodiments described herein. In some embodiments, the system may also determine a plurality of local duty cycles (623) corresponding to the plurality of signal sections using any one of the embodiments described herein. In some embodiments, the system further determines a plurality of section confidence values, each corresponding to one of the plurality of local cycle lengths (627), using any one of the embodiments described herein.

In some embodiments, each of the plurality of section confidence values is a confidence value for a signal section.

Next, the system may generate a local cycle length histogram based on the plurality of local cycle lengths (630). In some embodiments, the local cycle length histogram is a one-dimensional histogram. In some implementations, the bin of the local cycle length histogram is in milliseconds. In some cases, the local cycle length histogram is based on local cycle lengths that have confidence values greater than a predetermined threshold. In some embodiments, the system may generate a local duty cycle histogram based on the plurality of local duty cycles (633). In some embodiments, the local duty cycle histogram is a one-dimensional histogram. In some implementations, the bin of the local duty cycle histogram is between 0 and 1. In some cases, the local duty cycle histogram is based on local duty cycles that have confidence values greater than a predetermined threshold. In some embodiments, the system may generate a confidence value histogram based on the plurality of section confidence values (637). In some embodiments, the confidence value histogram is a one-dimensional histogram. In some implementations, the bin of the confidence value histogram is between 0 and 1.

Figure 7A:
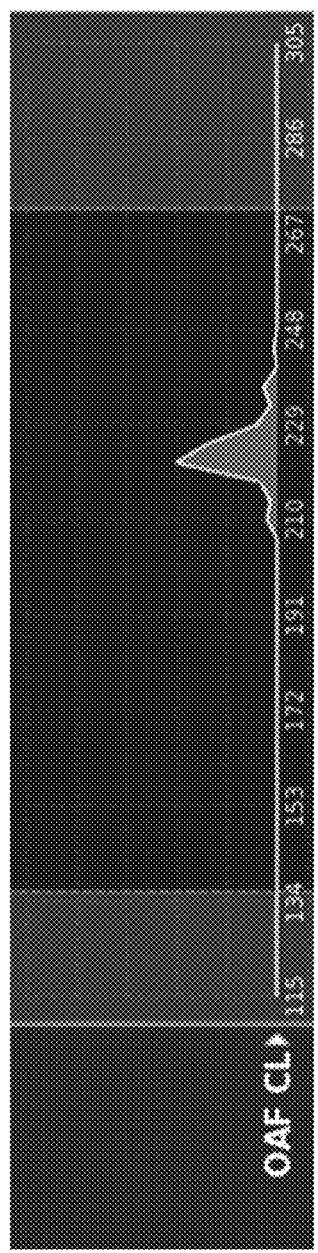
FIG. 7A is an illustrative example of a local cycle length histogram.
Figure 7B:
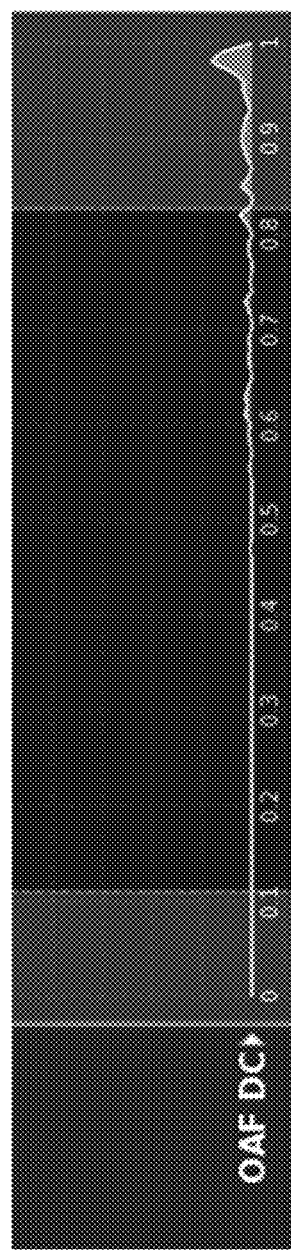
FIG. 7B is an illustrative example of a local duty cycle histogram.
Figure 7C:
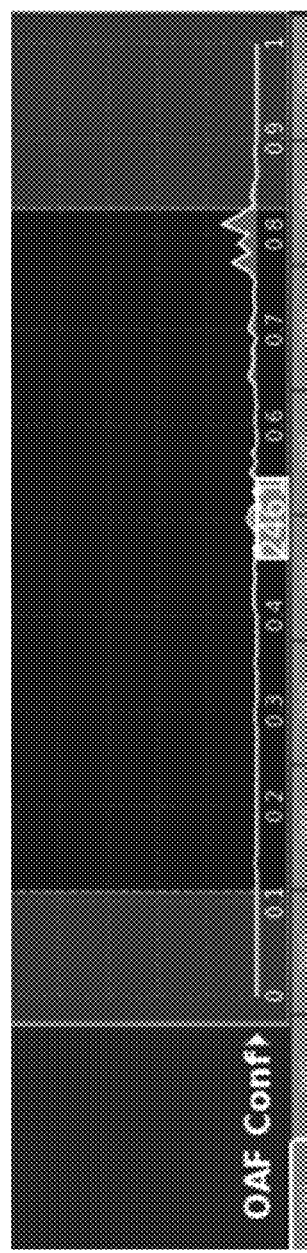
FIG. 7C is an illustrative example of a confidence value histogram.

Further, the system may generate a representation of the local cycle length histogram (640). FIG. 7A is an illustrative example of a local cycle length histogram. The system may also generate a representation of the local duty cycle histogram (643). FIG. 7B is an illustrative example of a local duty cycle histogram. In some cases, the system generates a representation of the confidence value histogram (647). FIG. 7C is an illustrative example of a confidence value histogram. In some embodiments, the system may receive inputs on region(s) of interest (650), for example, a region of interest for the local cycle lengths, a region of interest for the local duty cycles, and/or a region of interest of the confidence values. In some cases, the inputs on region(s) of interest may be received from users, for examples, via graphical user interface(s). In some cases, the inputs of region(s) of interest may be received from configuration settings and/or profile settings. In some cases, the inputs of region(s) of interest may be received from a software interface, for example, an application programming interface, a web service, or the like.

Figure 7D:
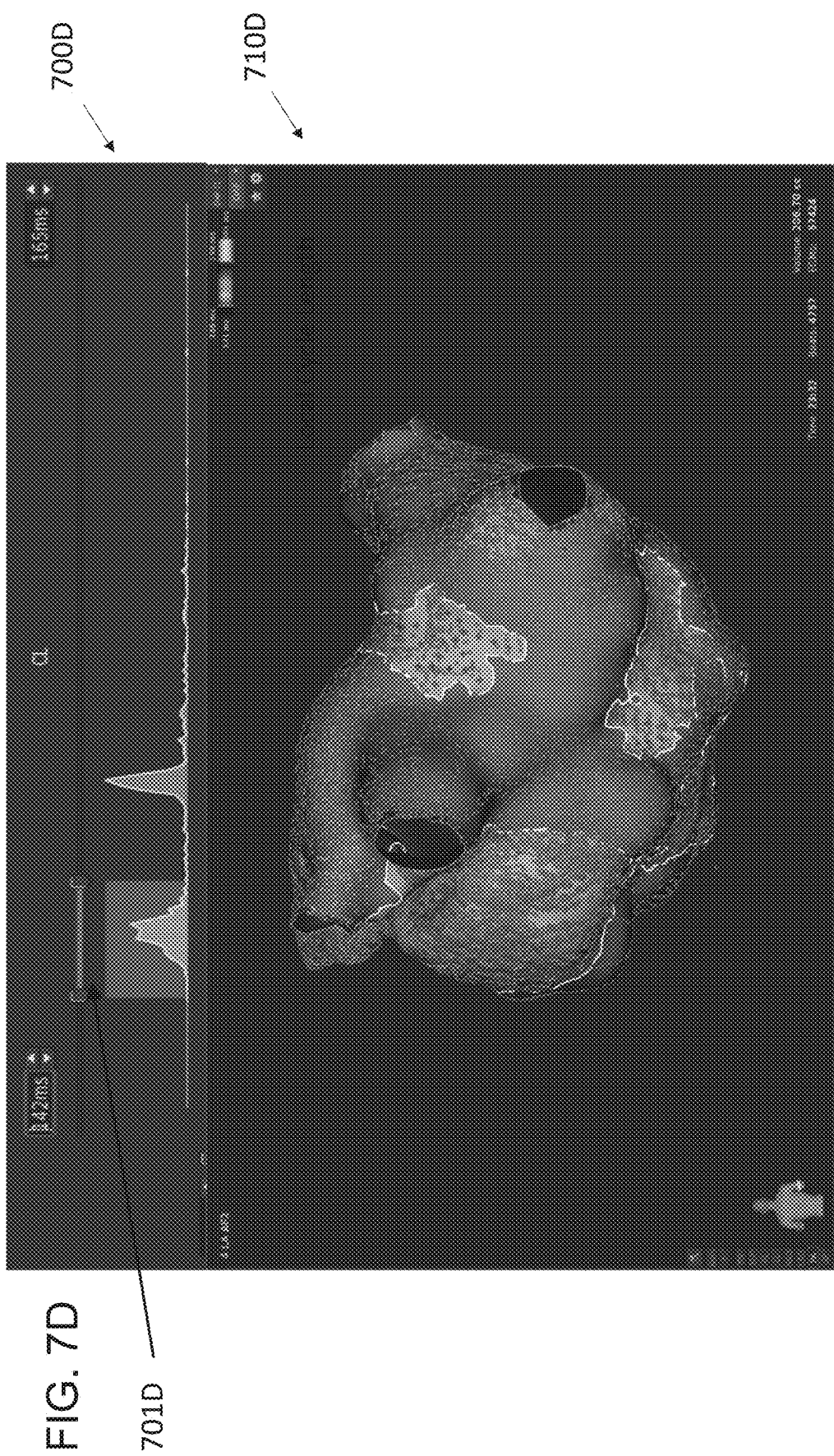
FIG. 7D depicts an illustrative example of a representation of a local cycle length histogram with a cardiac map.

In some embodiments, the system may show and/or overlay the region(s) of interest on the representation(s) of the histogram(s) (655), including the representation of the local cycle length histogram, the representation of the local duty cycle histogram, and/or the representation of the confidence value histogram. In some cases, the representation of the histogram is shown with a cardiac map. FIG. 7D depicts an illustrative example of a representation of a local cycle length histogram 700D with a cardiac map 710D. The local cycle length histogram representation 700D includes a region of interest 701D. As illustrated, the cardiac map 710D has indications of local cycle length values on the map. In one example, the cardiac map 710D illustrates each value/amplitude of local duty cycle by a color or a gray scale at the location of detection. When the electrophysiology system receives an input of the region of interest 701D, the system may update the cardiac map 710D to highlight the electrograms having the local cycle lengths within the region of interest 701D. The spatial dispersion of the highlighted region in the cardiac map can help clinical diagnosis.

Figure 8A:
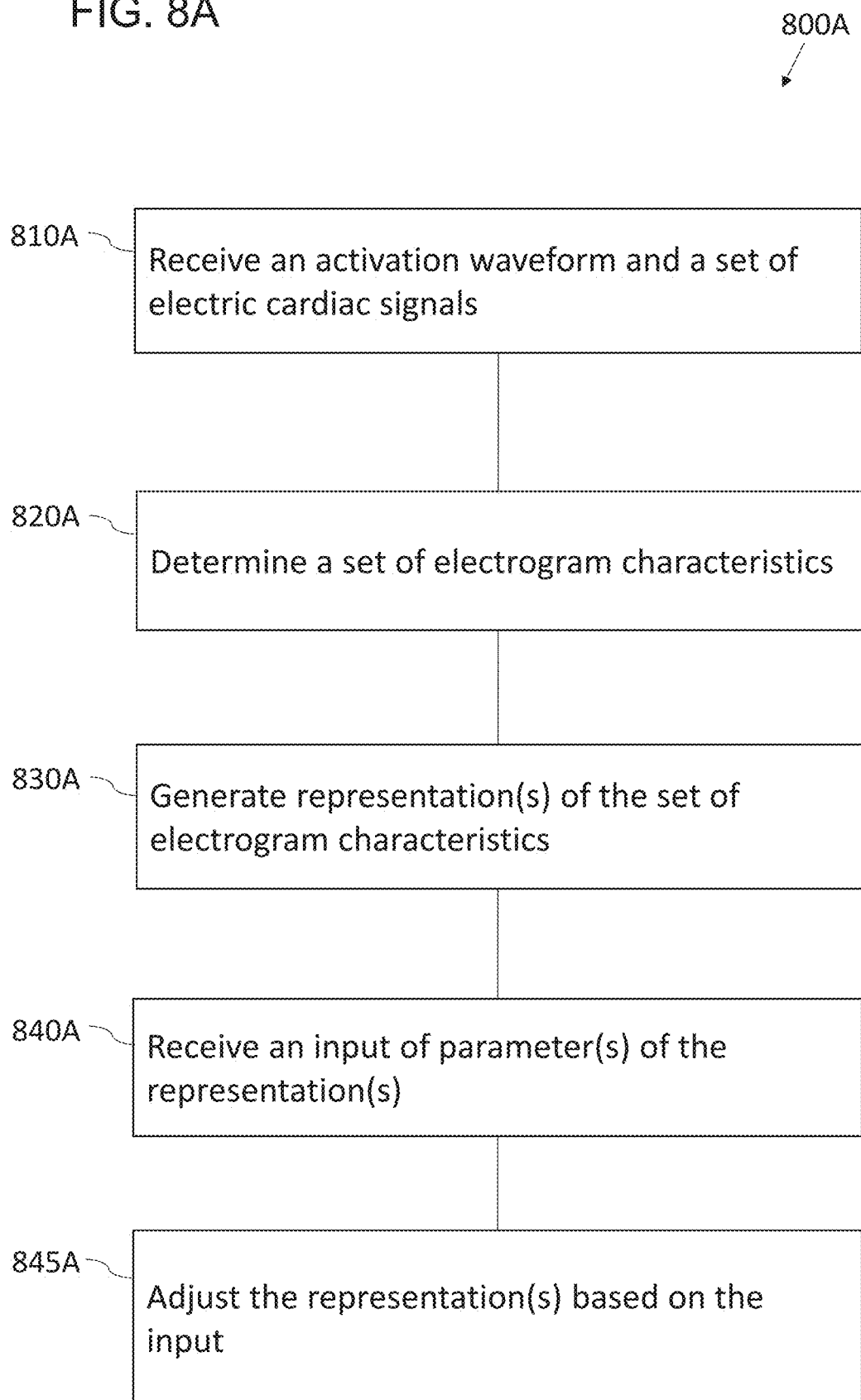
FIG. 8A is a flow diagram depicting an illustrative method of processing electrophysiology information to generate a representation of electrogram characteristics, in accordance with some embodiments of the present disclosure.

Knowledge on how local cycle length and duty cycle data cluster spatially in the anatomical context can be helpful in finding AF drivers within cardiac chambers. Multiple graphical representations, including interactive graphical representations, of electrogram characteristics (e.g., local cycle length, local duty cycle) can be generated. FIG. 8A is a flow diagram depicting an illustrative method 800A of processing electrophysiology information to generate a representation of electrogram characteristics, in accordance with some embodiments of the present disclosure. Aspects of embodiments of the method 800A may be performed, for example, by an electrophysiology system or a processing unit (e.g., the processing unit 120 depicted in FIG. 1, and/or the processing unit 200 depicted in FIG. 2). One or more steps of method 800A are optional and/or can be modified by one or more steps of other embodiments described herein. Additionally, one or more steps of other embodiments described herein may be added to the method 800A. First, the electrophysiology system receives an activation waveform and a set of cardiac electrical signals (810A), for example, including a set of activation waveform data of a plurality of signal sections collected at a plurality of locations. In some cases, the plurality of locations include a part or all of the heart chamber. In some cases, the plurality of locations are selected based on, for example, a user input (e.g., an input via a user interface such as a graphical user interface), a system input (e.g., system configuration), a software input (e.g., an input via an application programming interface, web service, etc.), or the like. In some cases, the plurality of locations are selected within a predetermined radius of a probe (e.g., roving probe) location. In some designs, the roving probe can be moved around in the heart chamber and the roving probe location is changed accordingly. In some cases, the roving probe location are indicated by an input, for example, a user input, a system input, a software input, or the like.

The system determines a set of electrogram characteristics (820A). In some cases, the set of electrogram characteristics includes a plurality of local cycle lengths corresponding to the plurality of signal sections. The plurality of local duty cycles can be determined using any one of the embodiments described herein. In some cases, the set of electrogram characteristics includes a plurality of local duty cycles corresponding to the plurality of signal sections. The plurality of local duty cycles can be determined using any one of the embodiments described herein. In some cases, the set of electrogram characteristics includes a plurality of section confidence values, each corresponding to one of the plurality of local cycle lengths. The plurality of section confidence values can be determined using any one of the embodiments described herein. In some embodiments, each of the plurality of section confidence values is a confidence value for a signal section.

Figure 9A:
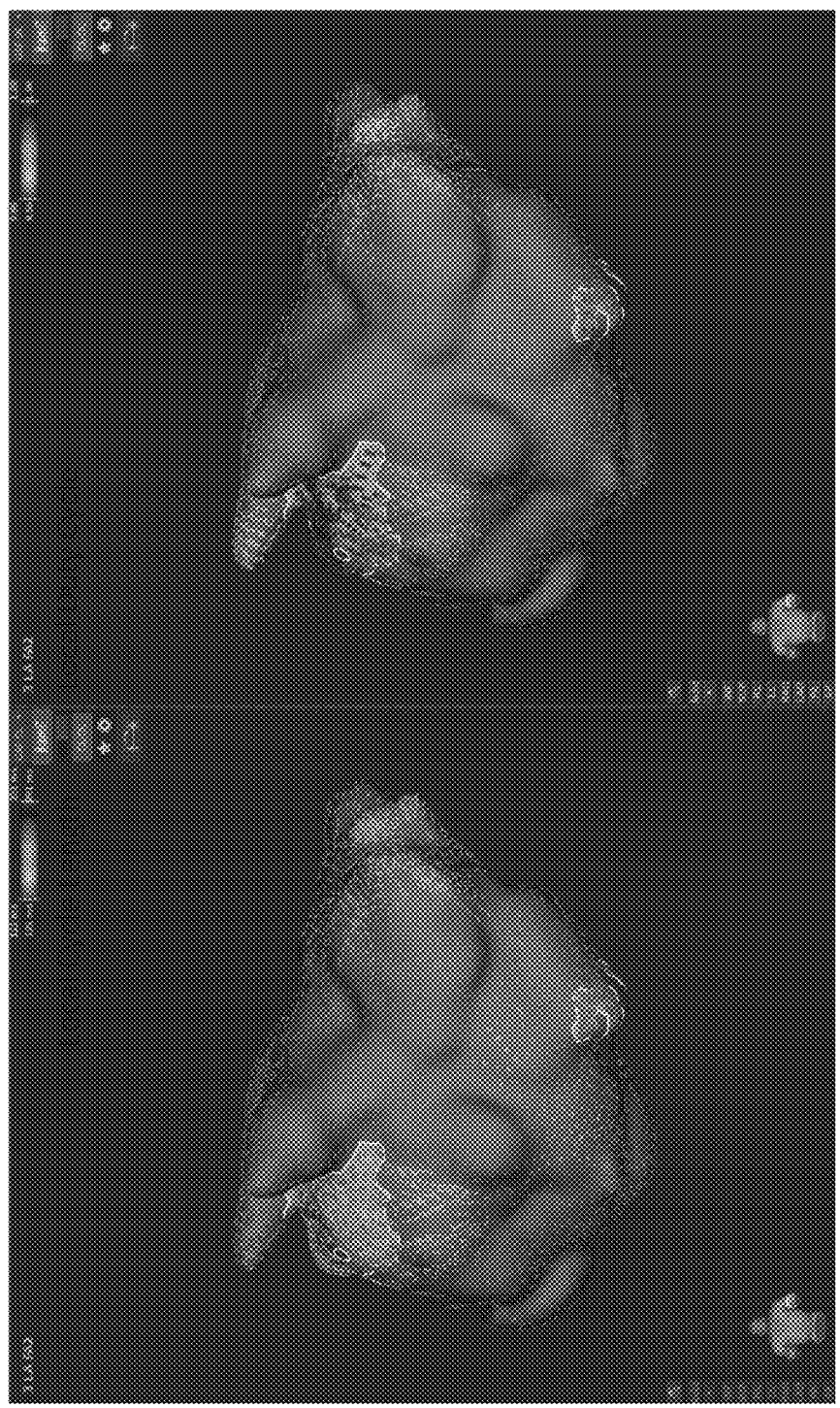
FIG. 9A depicts an illustrative example of cardiac maps with electrogram characteristics indications.

Next, the system generates representation(s) of the set of electrogram characteristics (e.g., local cycle length, local duty cycle, confidence value, etc.) (830A). In some embodiments, the representation is a graphical representation. In some embodiments, the representation is an interactive graphical representation, for example, taking inputs from users and adjusting or changing the representation based on the inputs. In one example, the representation is a graphical representation of one or more histograms, with examples illustrated in FIGS. 7A-7D, for example, to illustrate a spatial pattern and consistency of the respective characteristics. In one embodiment, the representation is a cardiac map with one or more electrogram characteristics indicated on the map and the value/amplitude of the characteristics represented in gray scales or in color. One illustrative example of cardiac maps with electrogram characteristics indications is depicted in FIG. 9A, where the 3D cardiac map 901A includes local cycle length indications and the 3D cardiac map 902A includes local duty cycles indications. In one case, the one or more electrogram characteristics (e.g., local cycle length, local duty cycle, etc.) illustrated in the graphical representation are the ones having confidence values above a predetermined threshold.

In another embodiment, the representation is a 3D cardiac map with one or more histograms illustrated on the side. In one case, the system receives an input either by a user or by a software interface on the region of interest of a histogram and updates the 3D cardiac map with respective characteristic. Referring back to FIG. 7D, one illustrative example of a local cycle length histogram 700D with a cardiac map 710D is depicted. When the electrophysiology system receives an input of the region of interest 701D, the system may update the cardiac map 710D to highlight the electrograms having the local cycle lengths within the region of interest 701D.

Figure 9B:
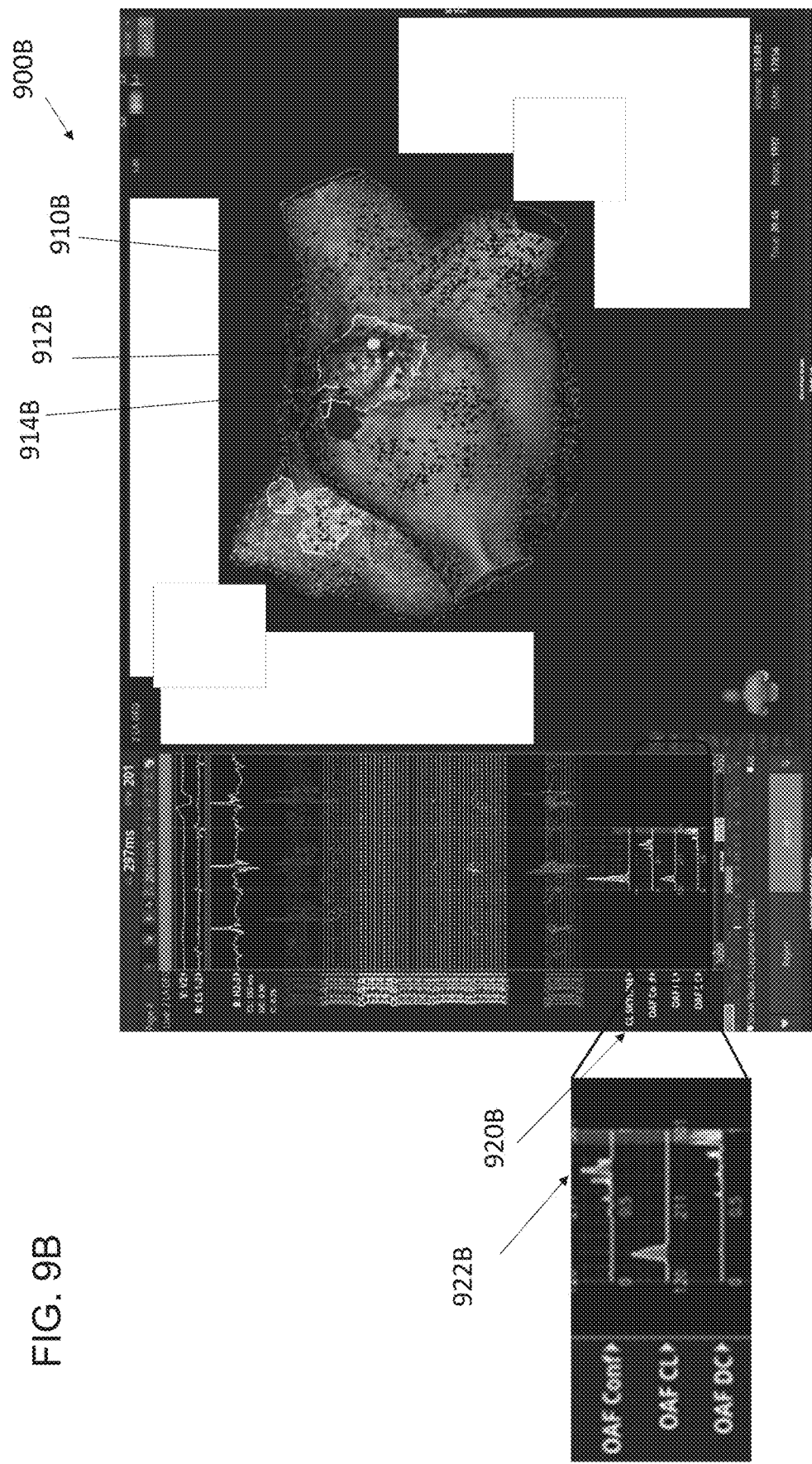
FIG. 9B depicts one illustrative example of a graphical representation having a roving probe.

In some embodiments, the electrophysiology system allows user to move a roving probe on a cardiac map to highlight certain area of the cardiac chamber and the graphical representation(s) of electrogram characteristics are updated corresponding to the change of the highlighted area. FIG. 9B depicts one illustrative example of a graphical representation 900B having a roving probe 912B that can be moved around on a cardiac map 910B. The roving probe 912B is associated with a highlighted area 914B that has a predetermined radius from the roving probe location, also referred to as a flashlight area. The graphical representation of electrogram characteristics 920B are updated corresponding to the change of the highlighted area 914B. In some cases, the highlighted area 914B is a circle of a predetermined radius of the roving probe 912B. In the example illustrated, the graphical representation of electrogram characteristics 920B, with an exploded view 922B, shows a plurality of histograms, including the confidence value histogram, the local cycle length histogram, and the local duty cycle histogram.

Figure 9C:
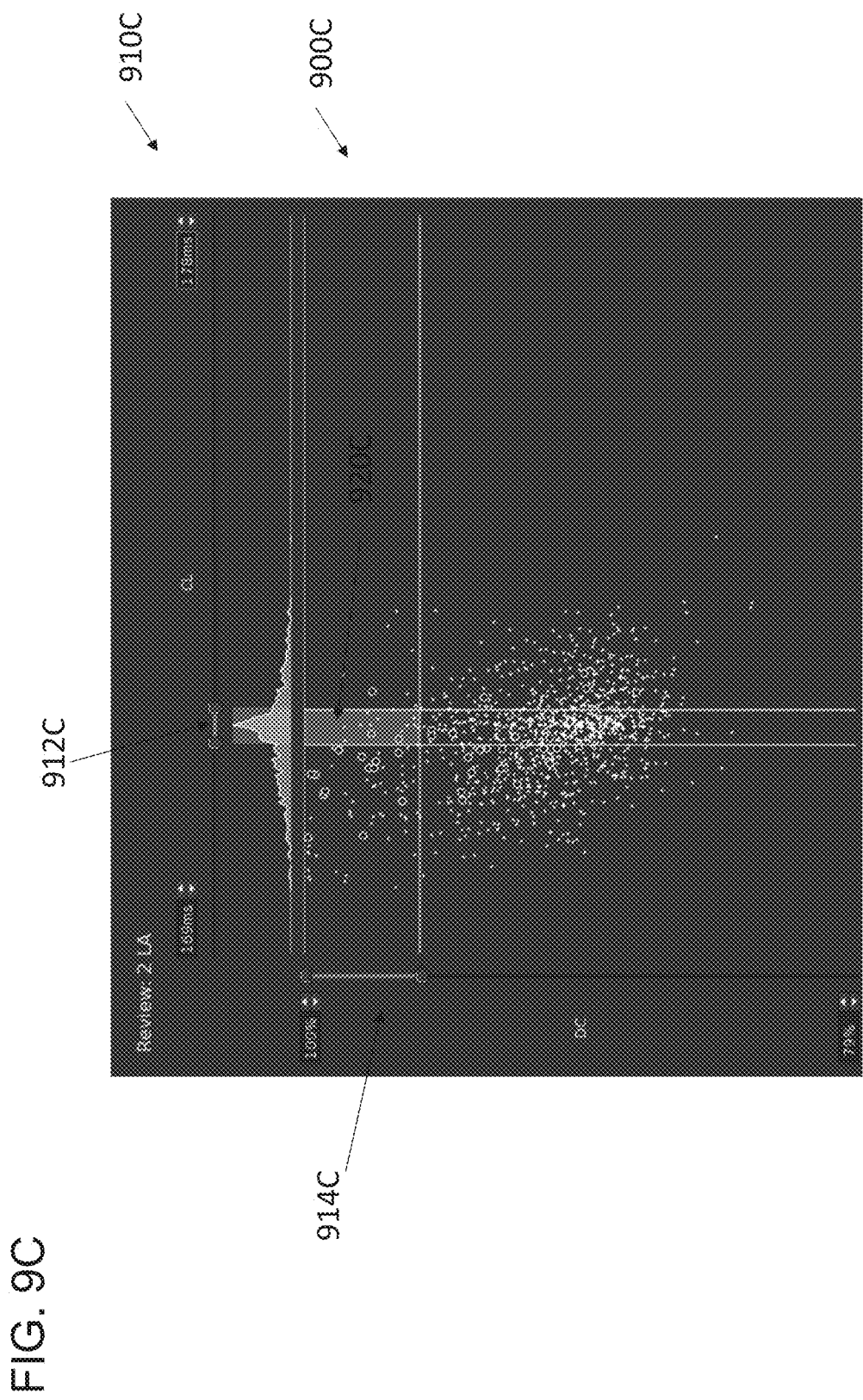
FIG. 9C depicts one illustrative example of a scatter plot.

In some cases, the graphical representation is a scatter plot. In one example, the x-axis of the scatter plot is the local cycle length and the y-axis is the local duty cycle. FIG. 9C depicts one illustrative example of a scatter plot 900C. In some designs, the system allows user to select a region of interest with a range in local cycle length and a range in local duty cycle. In some cases, the scatter map may be presented along with an electrogram characteristics histogram. In FIG. 9C, the local cycle length histogram 910C is illustrated with the scatter plot 900C and the region of interest 920C is selected by the range of the local cycle length 912C and the range of local duty cycle 914C. In one embodiment, the points in the scatter plot are annotated with a different color (e.g., red) or a different gray scale for the ones within a radius of a roving probe.

In some embodiments, the graphical representation is a scatter plot shown with one or more 3D cardiac maps. FIG. 9D depicts one illustrative example of such scatter plot 900D having a scatter plot 910D and one or more cardiac maps 920D. In the example illustrated, the scatter map 910D is the same as the graphical representation 900C shown in FIG. 9C. The one or more 3D cardiac maps 920D includes a cardiac map 922D showing local cycle length indications and a cardiac map 924D showing local duty cycle indications. In one example, the electrophysiology system receives input(s) of the region of interest from a user or a software interface and updates the 3D cardiac maps according the input(s). In the example illustrated in FIG. 9D, when the region of interest 914D is changed, the corresponding highlighted regions of interest 923D and 925D (i.e., the respective electrogram characteristics within the region of interest) are changed. For example, when the range of the local cycle length is changed, the highlighted region 923D in the cardiac map 922D is changed. As another example, when the range of the local duty cycle is changed, the highlighted region 925D in the cardiac map 924D is changed. In one embodiment, the one or more electrogram characteristics (e.g., local cycle length, local duty cycle, etc.) illustrated in the graphical representation are the ones having confidence values above a predetermined threshold. In one embodiment, the graphical representation uses confidence values to create a mask such that the electrogram characteristics having confidence values below a predetermined threshold are identifiable, for example, shown in gray, while the electrogram characteristics having confidence values above the predetermined threshold are shown in color(s).

In some embodiments, the system may receive an input of parameter(s) of the representation(s) (840A), for example, a roving probe location, a radius of a highlighted area, a region of interest for the local cycle lengths, a region of interest for the local duty cycles, and/or a region of interest of the confidence values. In some cases, the input of parameter(s) may be received from users, for examples, via a graphical user interface. In some cases, the input of parameter(s) may be received from configuration settings and/or profile settings. In some cases, the input of parameter(s) may be received from a software interface, for example, an application programming interface, a web service, or the like. In some embodiments, the system may adjust the representation(s) based on the input (845A) by, for example, updating the representation with only signals having local duty cycles in the region of interests.

Figure 8B:
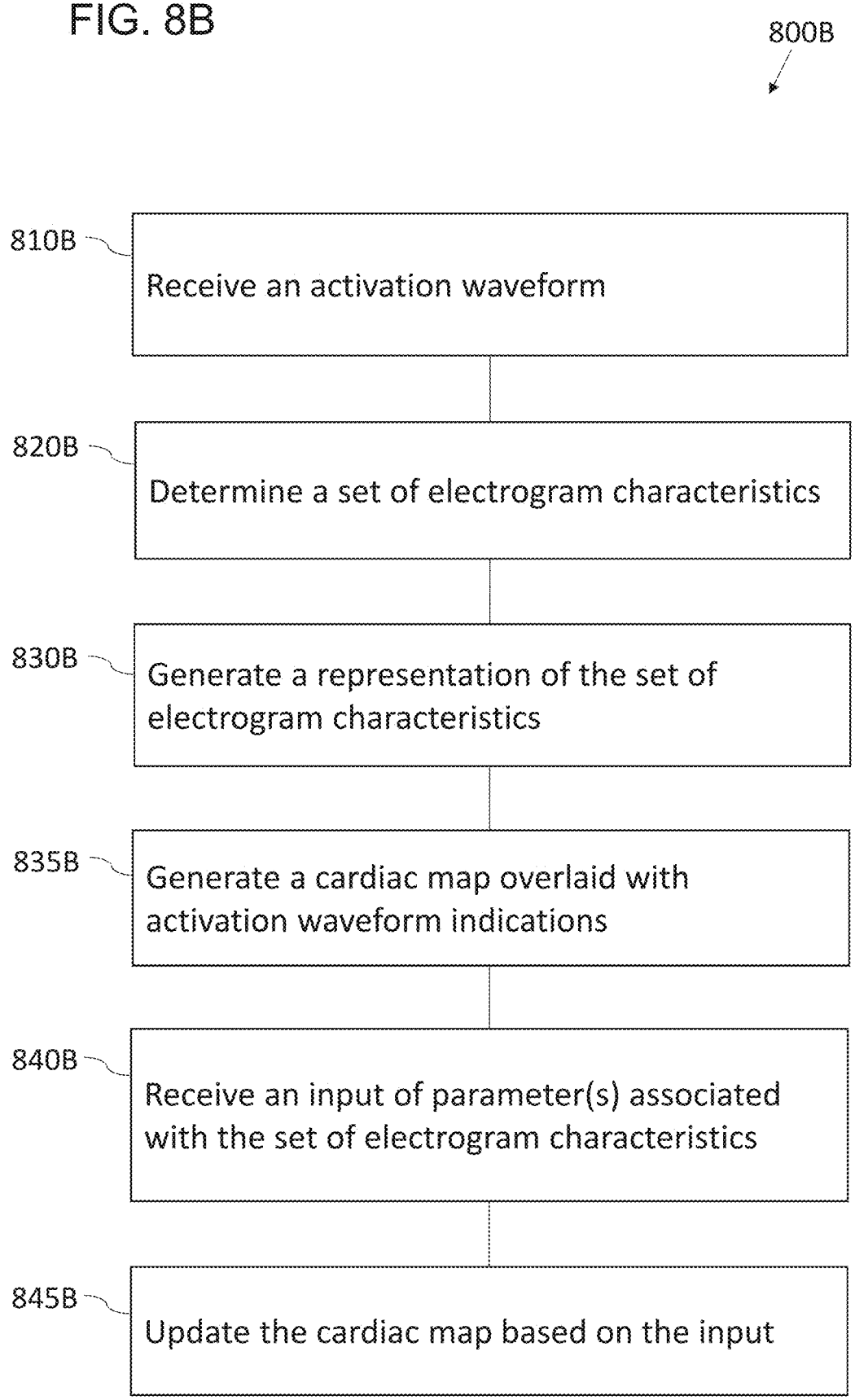
FIG. 8B is a flow diagram depicting an illustrative method of using a representation of electrogram characteristics to refine a cardiac map, in accordance with some embodiments of the present disclosure.

In some embodiments, the electrogram characteristics representation can be used to refine a cardiac map. In one example, the cardiac map is overlaid with activation waveform. FIG. 8B is a flow diagram depicting an illustrative method 800B of using a representation of electrogram characteristics to refine a cardiac map, in accordance with some embodiments of the present disclosure. Aspects of embodiments of the method 800B may be performed, for example, by an electrophysiology system or a processing unit (e.g., the processing unit 120 depicted in FIG. 1, and/or the processing unit 200 depicted in FIG. 2). One or more steps of method 800B are optional and/or can be modified by one or more steps of other embodiments described herein. Additionally, one or more steps of other embodiments described herein may be added to the method 800B. First, the electrophysiology system receives an activation waveform (810B), including a set of activation waveform data of a plurality of signal sections collected at a plurality of locations. In some cases, the plurality of locations include a part or all of the heart chamber. In some cases, the plurality of locations are selected based on, for example, a user input (e.g., an input via a user interface such as a graphical user interface), a system input (e.g., system configuration), a software input (e.g., an input via an application programming interface, web service, etc.), or the like. In some cases, the plurality of locations are selected within a predetermined radius of a probe (e.g., roving probe) location. In some designs, the roving probe can be moved around in the heart chamber and the roving probe location is changed accordingly. In some cases, the roving probe location are indicated by an input, for example, a user input, a system input, a software input, or the like.

The system determines a set of electrogram characteristics (820B), corresponding to the plurality of signal sections. In some cases, the set of electrogram characteristics includes a plurality of local cycle lengths corresponding to the plurality of signal sections. The plurality of local duty cycles can be determined using any one of the embodiments described herein. In some cases, the set of electrogram characteristics includes a plurality of local duty cycles corresponding to the plurality of signal sections. The plurality of local duty cycles can be determined using any one of the embodiments described herein. In some cases, the set of electrogram characteristics includes a plurality of section confidence values, each corresponding to one of the plurality of local cycle lengths. The plurality of section confidence values can be determined using any one of the embodiments described herein.

Figure 9E:
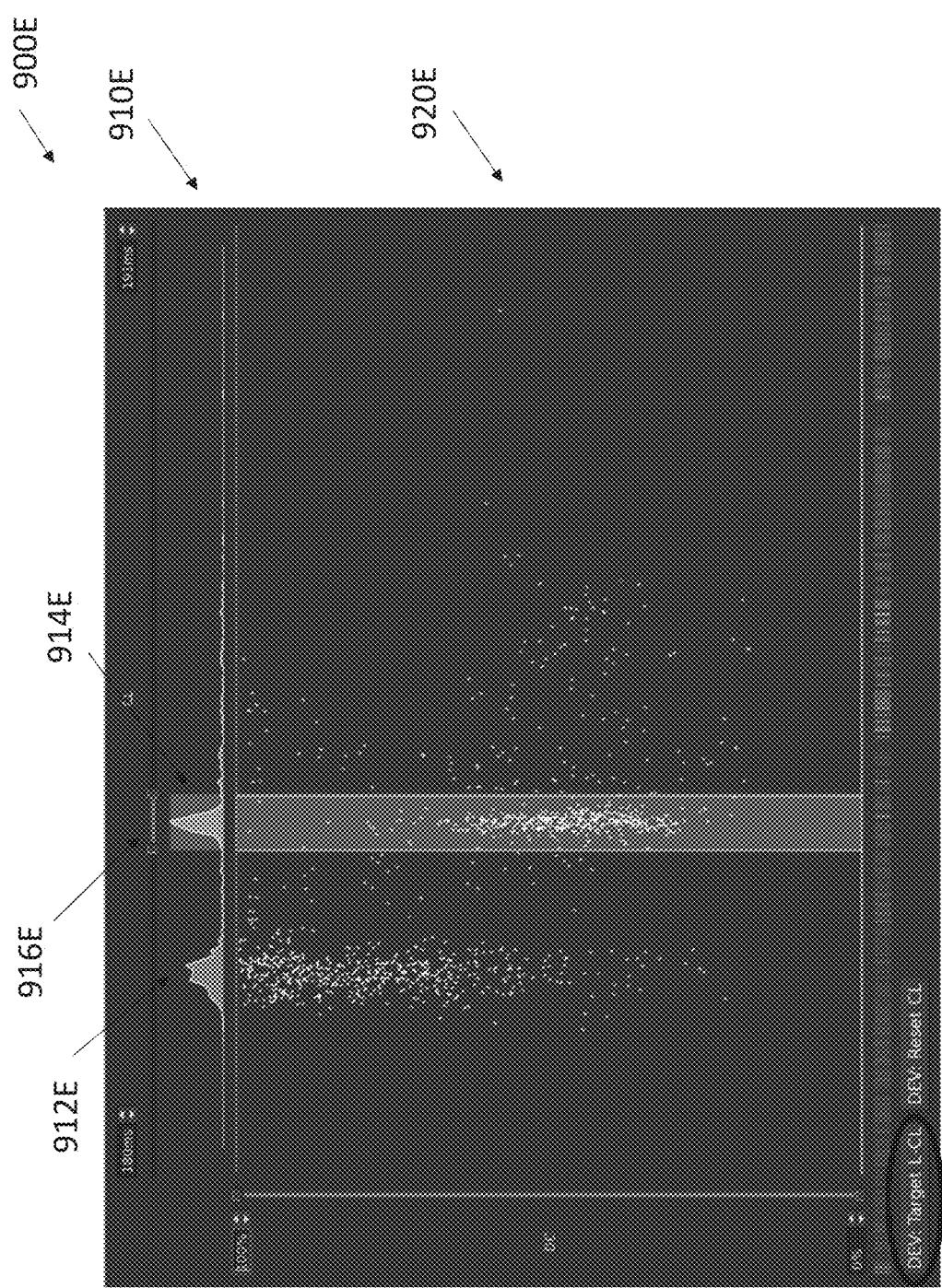
FIG. 9E depicts an illustrative example of a graphical representation of a set of electrogram characteristics.

Next, the system generates a representation of the set of electrogram characteristics (830B). In some embodiments, the representation is a graphical representation. In one example, the representation is a graphical representation of a histogram, for example, to illustrate a spatial pattern and consistency of the respective electrogram characteristics. In another example, the representation is a scatter plot to illustrate the distribution of data points. In one case, the x-axis of the scatter plot is the local cycle lengths and the y-axis of the scatter plat of the local duty cycles. In yet another example, the representation is one or more histogram illustrated with a scatter plot. FIG. 9E depicts an illustrative example of a graphical representation 900E of the set of electrogram characteristics. In the example illustrated, the representation 900E includes a local cycle length histogram 910E and a scatter plot 920E. In one example, the histogram shows two or more peaks of the respective electrogram characteristics, with one of the two or more peaks being of interest, or referred to as target characteristics. In one case, the target characteristics is associated with a reference catheter. As illustrated in FIG. 9E, the histogram 910E has two peaks 912E and 914E, where the peak 914E is associated with target cycle length. In one embodiment, the target characteristics is received, for example, from a different part of the electrophysiology system (e.g., reference catheter cycle length), another electrophysiology system, or from a user.

Figure 9F:
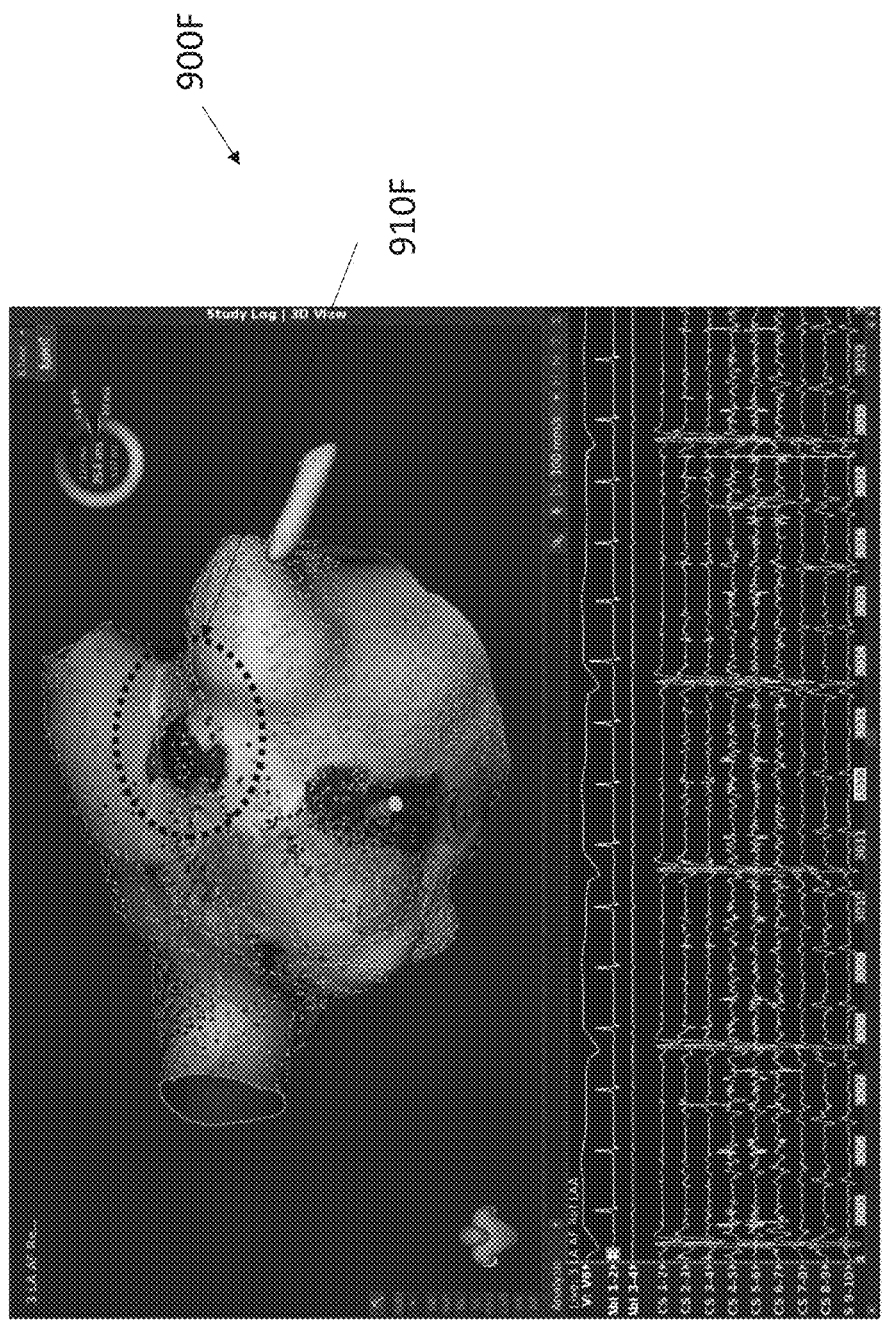
FIG. 9F depicts an illustrative example of a cardiac map overlaid with activation waveform indications.

The electrophysiology system may also generate a cardiac map overlaid with activation waveform data (835B). FIG. 9F depicts one illustrative example of a cardiac map overlaid with activation waveform indications 900F. In some cases, the representation of the electrogram characteristics is displayed side by side with the cardiac map. For example, the representation 900E of FIG. 9E is displayed side by side with the cardiac map overlaid with activation waveform indications 900F of FIG. 9F. The electrophysiology system may receive an input of parameter(s) associated with the set of electrogram characteristics (840B), for example, a region of interest for the local cycle lengths, a region of interest for the local duty cycles, and/or a region of interest of the confidence values. In one embodiment, the system may receive an input of target characteristics and determine a region of interest based on the input. In some cases, the input of parameter(s) may be received from users, for examples, via a graphical user interface. In some cases, the input of parameter(s) may be received from configuration settings and/or profile settings. In some cases, the input of parameter(s) may be received from a software interface, for example, an application programming interface, a web service, or the like.

Figure 9G:
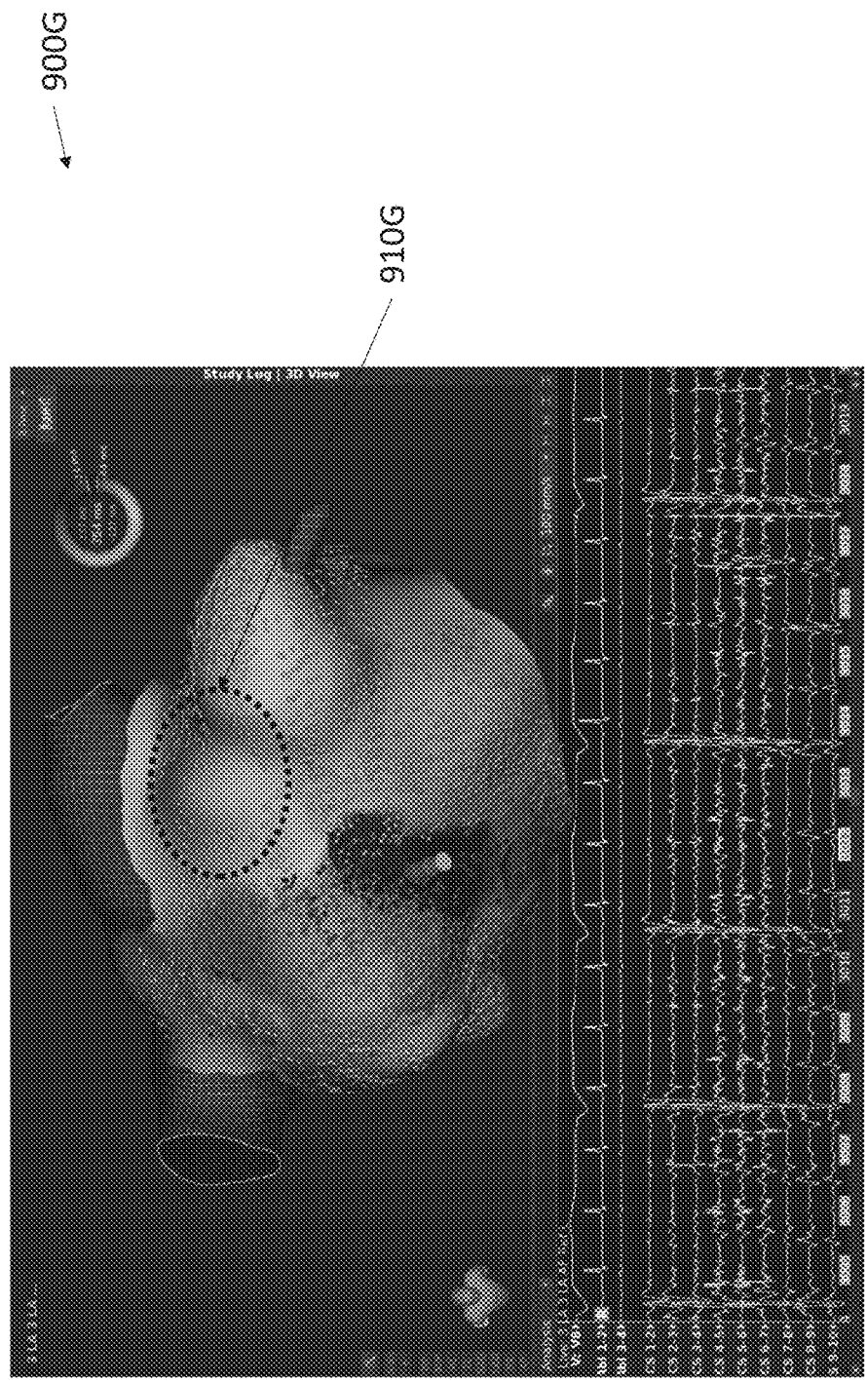
FIG. 9G depicts an illustrative example of a reprocessed cardiac map based on the cardiac map depicted in FIG. 9F.

The electrophysiology system can update the cardiac map based on the input (845B). In one example, the system may update the cardiac map including the set of electrogram data based on the input. For example, the updated cardiac map is generated only using cardiac electrical signals of the selected electrograms within the range of the local cycle lengths. Further, the system may generate a reprocessed cardiac map using the new set of electrogram data. FIG. 9G depicts an illustrative example of reprocessed cardiac map 900G based on the cardiac map depicted in FIG. 9F. Comparing FIG. 9F and FIG. 9G, the selected area 910G illustrates different activation waveform indications from the selected area 910F, where FIG. 9G can be better for identifying spatial patterns of the electrical propagation, shown by activation waveform indications.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of processing cardiac information, comprising:
   receiving an activation waveform comprising a set of activation waveform data of a plurality of signal sections collected at a plurality of locations;
   receiving a set of window parameters comprising a range of window size;
   for each of the plurality of signal sections,
      determining a set of confidence values, each confidence value corresponding to a window size of a plurality of window sizes, by iterating through each window size of the plurality of window sizes in the range of window size; such that,
         for each window size of the plurality of window sizes,
            selecting a position of a central window, the central window having the each window size;
            calculating a set of correlations, each of the set of correlations being a correlation of the activation waveform in the central window and the activation waveform in a shifted window, the shifted window being a sample window shifted from the central window and having the each window size; and
            determining one of the set of confidence values based on the set of correlations; and
         comparing the set of confidence values to select a designated confidence value and a selected window size corresponding to the designated confidence value; and
      determining one of a plurality of local cycle lengths for the each of the plurality of signal sections based on the selected window size; and
   generating a representation of the plurality of local cycle lengths.

2. The method of claim 1, wherein the representation is at least one of a histogram, a scatter plot, and a graphical representation of the plurality of local cycle lengths overlaid on a cardiac map.

3. The method of claim 1, further comprising:
   receiving an input of a parameter of the representation of the plurality of local cycle lengths; and
   adjusting the representation of the plurality of local cycle lengths based on the input.

4. The method of claim 1, wherein the plurality of locations are selected based on an input.

5. The method of claim 4, wherein the input indicates a probe location in the heart chamber, and wherein the plurality of locations are within a predetermined radius from the probe location.

6. The method of claim 1, further comprising:
   for each signal section of the plurality signal sections,
      determining one of a plurality local duty cycles based on the activation waveform of a selected central window having the selected window size, wherein the selected central window is corresponding to the designated confidence value.

7. The method of claim 6, further comprising:
   generating a representation of the plurality of duty cycles, wherein the representation is at least one of a histogram, a scatter plot and a graphical representation of the plurality of local duty cycles overlaid on a cardiac map.

8. The method of claim 6, further comprising:
   receiving an input of a parameter of the representation of the plurality local duty cycles; and
   adjusting the representation of the plurality local duty cycles based on the input.

9. The method of claim 1, further comprising:
   for each signal section of the plurality of signal sections,
      determining one of a plurality of section confidence values based on the set of confidence values.

10. The method of claim 9, further comprising:
    for each signal section of the plurality of signal sections,
       determining one of a plurality of section confidence values based on the designated backward confidence value, the designated forward confidence value, the selected backward window size, and the selected forward window size.

11. The method of claim 9, wherein each of the set of confidence values is based on an amplitude of the activation waveform in the central window of the selected window size and the set of correlations.

12. The method of claim 9, further comprising:
    generating a representation of the plurality of section confidence values,
    wherein the representation is at least one of a histogram, a scatter plot and a graphical representation of the plurality of local duty cycles overlaid on a cardiac map.

13. The method of claim 12, further comprising:
    receiving an input of a parameter of the representation of the plurality section confidence values; and
    adjusting the representation of the plurality section confidence values based on the input.

14. The method of claim 1, further comprising:
    generating a representation of the set of annotation waveform data overlaid on a cardiac map;
    receiving an input associated with the plurality of local cycle lengths;
    updating the annotation waveform based on the input; and
    updating the representation of the set of annotation waveform data overlaid on the cardiac map.

15. A system for processing cardiac information, the system comprising:
    a processing unit configured to:
       receive an activation waveform comprising a set of activation waveform data of a plurality of signal sections collected at a plurality of locations;
       receive a set of window parameters comprising a range of window size;
       for each of the plurality of signal sections,
          determine a set of confidence values, each confidence value corresponding to a window size of a plurality of window sizes, by iterating through each window size of the plurality of window sizes in the range of window size; such that, for each window size of the plurality of window sizes,
- select a position of a central window, the central window having the each window size;
- calculate a set of correlations, each of the set of correlations being a correlation of the activation waveform in the central window and the activation waveform in a shifted window, the shifted window being a sample window shifted from the central window and having the each window size; and
- determine one of the set of confidence values based on the set of correlations; and compare the set of confidence values to select a designated confidence value and a selected window size corresponding to the designated confidence value; and determine one of a plurality of local cycle lengths for the each of the plurality of signal sections based on the selected window size; and generate a representation of the plurality of local cycle lengths.

16. The system of claim 15, wherein the representation is at least one of a histogram, a scatter plot, and a graphical representation of the plurality of local cycle lengths overlaid on a cardiac map.

17. The system of claim 15, the processing unit is further configured to:
- receive an input of a parameter of the representation of the plurality of local cycle lengths; and
- adjust the representation of the plurality of local cycle lengths based on the input.

18. The system of claim 17, wherein the input indicates a probe location in a heart chamber, and wherein the plurality of locations are within a predetermined radius from the probe location.

19. The system of claim 15, further comprising:
for each signal section of the plurality signal sections,
- determining one of a plurality local duty cycles based on the activation waveform of a selected central window having the selected window size, wherein the selected central window is corresponding to the designated confidence value.

20. The system of claim 19, further comprising:
generating a representation of the plurality of duty cycles, wherein the representation is at least one of a histogram, a scatter plot and a graphical representation of the plurality of local duty cycles overlaid on a cardiac map.

* * * * *